United States Patent
Bold et al.

(10) Patent No.: US 7,855,215 B2
(45) Date of Patent: Dec. 21, 2010

(54) CYCLIC DIARYL UREAS SUITABLE AS TYROSINE KINASE INHIBITORS

(75) Inventors: Guido Bold, Gipf-Oberfrick (CH); Giorgio Caravatti, Bottmingen (CH); Andreas Floersheimer, Dornach (CH); Pascal Furet, Thann (FR); Paul W Manley, Arlesheim (CH); Carole Pissot Soldermann, Rosenau (FR); Andrea Vaupel, Riehen (CH)

(73) Assignee: Novartis AG, Basel (CH)

( * ) Notice: Subject to any disclaimer, the term of this patent is extended or adjusted under 35 U.S.C. 154(b) by 653 days.

(21) Appl. No.: 11/575,601

(22) PCT Filed: Sep. 27, 2005

(86) PCT No.: PCT/EP2005/010408
§ 371 (c)(1),
(2), (4) Date: Mar. 20, 2007

(87) PCT Pub. No.: WO2006/034833
PCT Pub. Date: Apr. 6, 2006

(65) Prior Publication Data
US 2008/0039440 A1 Feb. 14, 2008

(30) Foreign Application Priority Data
Sep. 28, 2004 (GB) .................. 0421525.7

(51) Int. Cl.
*A61K 31/505* (2006.01)
*A61K 31/506* (2006.01)
*C07D 239/02* (2006.01)
*C07D 401/12* (2006.01)
*C07D 413/12* (2006.01)

(52) U.S. Cl. ............ 514/265; 514/275; 544/316; 544/319; 544/333

(58) Field of Classification Search ............... 544/316, 544/319, 333; 514/265, 275
See application file for complete search history.

(56) References Cited

U.S. PATENT DOCUMENTS
2004/0053908 A1 3/2004 Funahashi et al.

FOREIGN PATENT DOCUMENTS
EP 1475368 11/2004
WO WO 03/099771 12/2003
WO WO 2004/020434 3/2004
WO WO 2004/043379 5/2004

OTHER PUBLICATIONS
Wolff, Manfred E. "Burger's Medicinal Chemistry and Drug Discovery, 5ed, vol. 1" John Wiley & Sons, 1995, pp. 975-977.*
Banker, G.S. et al, "Modern Pharmaceutics, 3ed." Marcel Dekker, New York, 1996, pp. 451 and 596.*
* cited by examiner Primary Examiner—Kahsay T Habte

(57) ABSTRACT

The invention relates to novel compounds of Formula I:

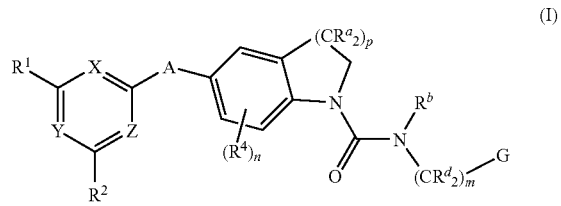

wherein
p is 1, 2 or 3;
n is 0, 1, 2 or 3;
m is 0, 1, 2 or 3;
A is $CR^c$, S, $NR^c$ or O, where $R^c$ is H or lower alkyl;
X, Y and Z are each independently selected from N or C—$R^3$, wherein at least two of X, Y and Z are N; and
each $R^a$ is independently selected from hydrogen and lower-alkyl;
each $R^b$ is hydrogen or lower-alkyl;
G is a group Ar or represents CN or unsubstituted or substituted lower alkyl;
Ar is a saturated or unsaturated cyclic group, which is substituted or unsubstituted and maybe a five or six membered monocyclic or a 8, 9, 10, 11 or 12 membered bicyclic or tricyclic ring and may contain 0, 1, 2 or 3 heteroatoms selected from O, N and S;
and wherein the radicals have $R^1$, $R^2$, $R^3$ and $R^4$ have the meanings as defined herein,
to salts, esters, N-oxides or prodrugs thereof;
and their use in the treatment of protein kinase dependent diseases, their use in the manufacture of pharmaceutical compositions for use in the treatment of said diseases, methods of use of diary urea derivatives in the treatment of said diseases, pharmaceutical preparations comprising these novel diaryl urea derivatives, processes for the manufacture of the novel diaryl urea derivatives, the use or methods of use of the novel diaryl urea derivatives as mentioned above, and/or these novel diaryl urea derivatives for use in the treatment of the animal or human body.

19 Claims, No Drawings

CYCLIC DIARYL UREAS SUITABLE AS TYROSINE KINASE INHIBITORS

SUMMARY OF THE INVENTION

The invention relates to novel compounds, methods and uses. More particularly it relates to compounds, which may be described as diaryl urea derivatives, for use in the treatment of protein kinase dependent diseases, or for their use in the manufacture of pharmaceutical compositions for use in the treatment of said diseases, methods of use of diaryl urea derivatives in the treatment of said diseases, pharmaceutical preparations comprising diary urea derivatives useful in the treatment of said diseases, diaryl urea derivatives for use in the treatment of said diseases, pharmaceutical preparations comprising these novel diary urea derivatives, processes for the manufacture of the novel diaryl urea derivatives, the use or methods of use of the novel diaryl urea derivatives as mentioned above, and/or these novel diaryl urea derivatives for use in the treatment of the animal or human body. The invention relates to other subject matter as disclosed below.

BACKGROUND OF THE INVENTION

Protein kinases (PKs) are enzymes which catalyze the phosphorylation of specific serine, threonine or tyrosine residues in cellular proteins. These post-translational modifications of substrate proteins can act as molecular switches to regulate cell proliferation, activation and/or differentiation. Aberrant or excessive PK activity has been observed in many disease states including benign and malignant proliferative disorders. It is frequently possible to regulate cellular activity in vitro and in many cases to treat diseases in vivo, such as proliferative disorders, by employing PK inhibitors.

In view of the large number of protein kinase inhibitors and the multitude of proliferative and other PK-related diseases, there is an ever-existing need to provide novel classes of compounds that are useful as PK inhibitors and thus in the treatment of these Protein Tyrosine Kinase (PTK) related diseases. What is required are new classes of pharmaceutically advantageous PK inhibiting compounds.

The Philadelphia Chromosome is a hallmark for chronic myelogenous leukaemia (CML) and carries a hybrid gene that contains N-terminal exons of the bcr gene and the major C-terminal part (exons 2-11) of the c-abl gene. This gene encodes a 210 kD protein, p210 Bcr-Abl, the Abl sequence of which contains the Abl-tyrosine kinase domain which is tightly regulated in the wild type c-Abl, but constitutively activated in the Bcr-Abl fusion protein. This deregulated tyrosine kinase interacts with multiple cellular signalling pathways leading to transformation and deregulated proliferation of the cells (Lugo et al., Science 247, 1079 [1990]).

Mutant forms of the Bcr-Abl protein have also been identified. A detailed review of Bcr-Abl mutant forms has been published (Cowan-Jones et al, Mini Reviews in Medicinal Chemistry, 2004, 4 285-299).

GENERAL DESCRIPTION OF THE INVENTION

It has now been found that various compounds, which may be described as belonging to the diaryl urea derivative class, can inhibit a number of protein tyrosine kinases. The compounds of Formula I, II, III, IV, V, VI, VII, VIII or IX (or exemplary formula thereof), described below in more detail, especially show inhibition of protein kinases e.g. protein tyrosine kinases. As examples of kinases inhibited by the compounds of the disclosure may be mentioned c-Abl and Bcr-Abl, in particular, inhibition of Bcr-Abl may be mentioned. The compounds of the present invention also inhibit mutant forms of the Bcr-Abl kinases. Other kinases which are inhibited are the receptor tyrosine kinases VEGF-R, in particular the VEGF receptor KDR (VEGF-R2), PDGFR, c-Kit and Ret. The disclosed compounds are appropriate for the inhibition of one or more of these and/or other receptor protein tyrosine kinases and/or the non-receptor tyrosine kinases, such as Raf, and/or for the inhibition of mutants of these enzymes. In view of these activities, the compounds can be used for the treatment of diseases related to, especially, aberrant or excessive activity of such types of kinases, especially those mentioned.

One class of target kinases of the compounds of the present invention are Bcr-Abl mutants. The mutants Glu255→Lysine, Glu255→Valine or the Thr315→Isoleucine may be especially mentioned, most especially the Thr315→Isoleucine mutant.

Other Bcr-Abl mutants include Met244→Val, Phe317→Leu, Leu248→Val, Met343→Thr, Gly250→Ala, Met351→Thr, Gly250→Glu, Glu355→Gly, Gln252→His, Phe358→Ala, Gln252→Arg, Phe359→Val, Tyr253→His, Val379→Ile, Tyr253→Phe, Phe382→Leu, Glu255→Lys, Leu387→Met, Glu255→Val, His396→Pro, Phe311→Ile, His396→Arg, Phe311→Leu, Ser417→Tyr, Thr315→Ile, Glu459→Lys and Phe486→Ser.

DETAILED DESCRIPTION OF THE INVENTION

The present invention relates to compounds of Formula I or salts, esters, N-oxides or prodrugs thereof:

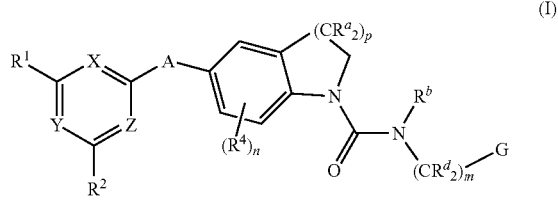

(I)

wherein
p is 1, 2 or 3;
m is 0, 1, 2 or 3;
n is 0, 1, 2 or 3;
A is $CR^e$, S, $NR^c$ or O, where $R^c$ is H or lower alkyl;
X, Y and Z are each independently selected from N or C—$R^3$, wherein at least two of X, Y and Z are N; and
each $R^a$ and $R^d$ are independently selected from hydrogen and lower-alkyl;
each $R^b$ is hydrogen or lower-alkyl;
$R^1$, $R^2$ and $R^3$ are each independently selected from an organic or inorganic moiety,
wherein the inorganic moiety is especially selected from halo, especially chloro, hydroxyl, etherified and esterified hydroxyl, cyano, azo (N=N=N) and nitro; and
where the organic moiety is substituted or unsubstituted and may be attached via a linker, -$L^1$-, the organic moiety being especially selected from hydrogen; lower alkyl, especially linear or branched $C_1$-$C_6$ alkyl, lower alkenyl or lower alkynyl, optionally substituted with one or more substituents and/or interrupted by one or more heteroatoms; lower alkoxy, especially methoxy or ethoxy; lower-alkanoyl; aroyl; heteroaroyl; carboxy; carboxamido which unsubstituted or substituted by linear or branched $C_1$-$C_6$ alkyl; amino; a cyclic group, for example cycloalkyl, e.g. cyclohexyl, phenyl, pyrrole, imidazole, pyrazole, isoxazole, oxazole, thiazole, pyridazine, pyrimidine, pyrazine, pyridyl, indole, isoindole, indazole, purine, indolizidine, quinoline, isoquinoline, quinazoline, pteridine, quinolizidine, piperidyl, piperazinyl, pyrollidine, morpholinyl and thiomorpholinyl; or mono- or di-substituted amino, the amino optionally being substituted by a hydrocarbyl moiety, the hydrocarbyl moiety being, for example, selected from lower alkyl, especially linear or branched $C_1$-$C_6$ alkyl, cycloalkyl, especially cyclohexyl, carboxy, lower alkanoyl, especially acetyl, lower alkoxy carbonyl, lower alkyl sulfonyl, aroyl, such as benzoyl or nicotinoyl, a carbocyclic group, for example phenyl, a heterocyclic group and heterocyclyl carbonyl; where the hydrocarbyl moiety is substituted or unsubstituted;

and -$L^1$- having 1, 2, 3 or 4 in-chain atoms (e.g. selected from C, N, O and S) and optionally being selected from $C_1$, $C_2$, $C_3$ or $C_4$ alkyl; such an alkyl group optionally being interrupted and/or terminated by an —O— or —NH— linkage; O; N; or S; and wherein -$L^1$- can also be carbonyl;

wherein there is at least one of $R^1$, $R^2$ or $R^3$ which is not hydrogen; and when Z is C—$R^3$, either $R^1$ is not H or $R^2$ is not Cl, or both;

wherein, when X represent $CR^3$, $R^3$ and $R^1$ together with the carbon atoms to which they are attached form a five- or six-membered unsaturated ring containing at least one nitrogen atom;

$R^4$ is selected from an organic or inorganic moiety, for example, $R^4$ is selected from halogen, lower alkyl, halo-lower alkyl, carboxy, lower alkoxycarbonyl, hydroxy, etherified or esterified hydroxy, lower alkoxy, phenyl, substituted phenyl, for example phenyl-loweralkoxy, lower alkanoyloxy, lower alkanoyl, amino, mono- or di-substituted amino, amidino, ureido, mercapto, N-hydroxy-amidino, guanidino, amidino-lower alkyl, sulfo, sulfamoyl, carbamoyl, cyano, cyano-lower alkyl and nitro.

$R^4$ is commonly selected from hydroxy, lower alkyl or halo (notably F or Cl). n is preferably zero or 1.

In one sub-group of compounds, at least one $R^a$ group is hydrogen. In a second subgroup at least two $R^a$ groups are hydrogen. In a further class of compounds, one of the $R^a$ groups attached to each carbon is hydrogen, thus forming $(CHR^a)_p$. In a further sub-group of compounds of Formula I, all $R^a$ groups are hydrogen, thus forming $(CH_2)_p$. In another sub-group of compounds of Formula I, in at least one unit $(CR^a)$ both radicals $R^a$ are independently selected from lower alkyl.

In a preferred embodiment of the invention $R^b$ is hydrogen.

Preferably, where lower alkyl is a $C_3$ alkyl, it is either $^iPr$ or cyclopropyl and where alkyl amino is $C_4$ alkyl, it is $^tBu$. This is also true where lower alkyl is a substituent to another group, e.g. alkyl amino. Thus a preferred sub-set of lower alkyl amino is $^iPr$, cyclopropyl or $^tBu$ amino. This applies in particular to $R^1$, $R^2$ and $R^3$.

In one class of compounds, at least one of $R^1$, $R^2$ and $R^3$ is selected from hydrogen, halo, amino and a mono- or di-substituted amino, the amino optionally being substituted by a hydrocarbyl moiety, the hydrocarbyl moiety being, for example, selected from lower alkyl, especially linear or branched $C_1$-$C_6$ alkyl, especially cyclohexyl, carboxy, lower alkanoyl, especially acetyl, a carbocyclic group, for example cycloalkyl or phenyl, a heterocyclic group; where the hydrocarbyl moiety is substituted or unsubstituted. Most common is a mono substituted amino group.

Particularly preferred $R^1$, $R^2$ and $R^3$ groups are:

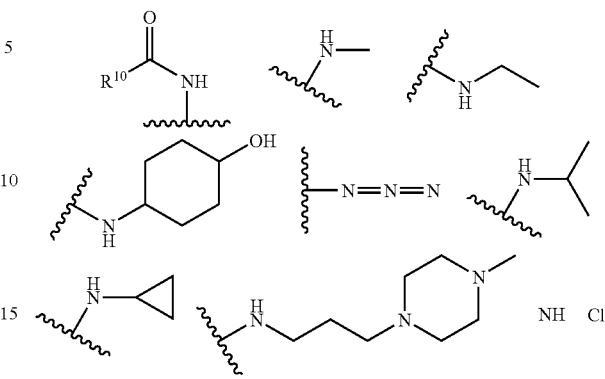

$R^1$ especially comprises lower acylamino, e.g. alkanoylamino, or aroylamino, e.g. nicitinoylamino. Other particular groups are carbamic esters (Z—O—C(O)—NH—, where Z is an ester-forming group). Exemplary esters are lower alkyl, e.g. methyl. Included as ester derivatives are carbamates, for example carbamic acid alkyl esters, e.g. methyl ester (MeOC (O)—NH—).

In an exemplary class of compounds, p is 1.

In a further exemplary class of compounds, A is oxygen.

Preferably, the or each linker $L^1$ is selected from —$CH_2$—, O, carbonyl or a covalent bond.

In a preferred class of compounds one of X, Y and Z is —$CR^3$ and the other two are —N=.

$R^3$ is most commonly hydrogen.

The G Moiety

G is preferably a group Ar as defined below. In a broader sense, G can also represent CN or unsubstituted or substituted lower alkyl.

Ar is a saturated or unsaturated cyclic group, which is substituted or unsubstituted and may be a five or six membered monocyclic or a 8, 9, 10, 11 or 12 membered bicyclic or tricyclic ring and may contain 0, 1, 2 or 3 heteroatoms selected from O, N and S. Ar may comprise an aromatic ring.

The cyclic group is in most cases selected from phenyl, $C_3$-$C_6$-cycloalkyl, tetrahydronaphthyl, pyrrole, imidazole, pyrazole, isoxazole, oxazole, thiazole, pyridazine, pyrimidine, pyrazine and pyridyl. Also of choice are adamantyl, [2.2.1]bicycloheptanyl, furane, indole, isoindole, indazole, purine, indolizidine, quinoline, isoquinoline, quinazoline, pteridine, quinolizidine, benzodiazolyl, benzimidazolyl, benzoxazolyl, benzo[c]1-thia-2,5-diazolyl, thienyl, 2-oxo-tetrahydrothienyl, piperidyl, piperazinyl, tetrahydrofuranyl, pyrollidine, 1,3-dioxacyclopentanyl, morpholinyl and thiomorpholinyl, all of which may be substituted or unsubstituted. The cyclic group is most commonly an aromatic ring.

Most preferably, the cyclic group is selected from phenyl, pyrrole, imidazole, pyrazole, isoxazole, oxazole, thiazole, pyridazine, pyrimidine, pyrazine and pyridyl, of which phenyl is most common. As previously indicated, the cyclic group may be substituted.

The cyclic group may be substituted by one or more of the substituents as listed under the heading "Substituents". Examples of substituents are, halo, especially chloro, hydroxyl, etherified or esterified hydroxy, cyano, azo (N=N=N), nitro; and substituted or unsubstituted moieties selected from lower alkyl, especially $C_1$, $C_2$, $C_3$ or $C_4$ alkyl, especially trifluoromethyl, lower alkenyl, lower alkynyl, lower alkoxy, especially methoxy or ethoxy, amino, a carbocyclic group, a heterocyclic group or mono- or di-substituted amino, the amino group being substituted by a substituted or unsubstituted hydrocarbyl moiety, the hydrocarbyl moiety being, for example, selected from lower alkyl, especially $C_1$, $C_2$, $C_3$ or $C_4$ alkyl; cycloalkyl, especially cyclohexyl; lower alkanoyl, especially acetyl; phenyl.

In one class of compounds it is preferred that at least one hydrogen of the cyclic group is replaced by a substituent. In another class of compounds it is preferred that at least two hydrogens are relaced by a substituent. In yet another class of compounds it is preferred that the substituents are in the meta or para positions, especially where the cyclic group is phenyl.

Ar is particularly selected from

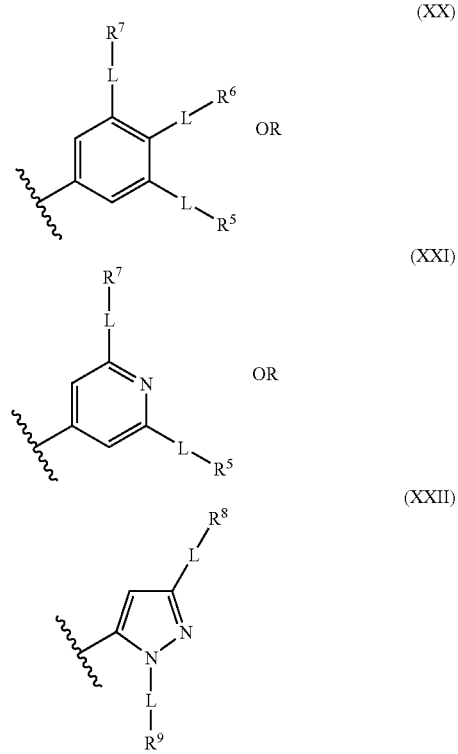

where $R^5$, $R^6$, $R^7$, $R^8$ and $R^9$ are each independently selected from an organic or inorganic moiety;
  where the inorganic moiety is especially selected from hydrogen, halo, especially chloro, hydroxyl, etherified or esterified hydroxy, cyano, azo (N=N=N), nitro; and
  where the organic moiety is substituted or unsubstituted and is especially selected from lower alkyl, especially $C_1$, $C_2$, $C_3$ or $C_4$ alkyl, lower alkenyl, lower alkynyl, lower alkoxy, especially methoxy or ethoxy, amino, a carbocyclic group, a heterocyclic group or
mono- or di-substituted amino, the amino group being substituted by a substituted or unsubstituted hydrocarbyl moiety, the hydrocarbyl moiety being, for example, selected from lower alkyl, especially $C_1$, $C_2$, $C_3$ or $C_4$ alkyl; cycloalkyl, especially cyclohexyl; lower alkanoyl, especially acetyl; phenyl;
  or any two of -L-$R^5$, -L-$R^6$ or -L-$R^7$ together form a lower alkylene-dioxy bridge bound via the oxygen atoms;
  or any two of -L-$R^5$, -L-$R^6$ or -L-$R^7$ together form a five, six or seven membered ring e.g. a heterocyclic ring, or unsubstituted, especially a substituted indazole ring;

L is a covalent bond or a moiety which comprises 1, 2, 3 or 4 in-chain atoms selected from carbon, oxygen, sulphur and nitrogen (e.g. —NH—). Preferably, the linker L or each linker L is selected from —CH$_2$—, O or a covalent bond. L can also represent carbonyl.

Normally, Ar groups have at least one -L-R″ substituent which is not H, e.g. two which are not H. In the case of Formulae XX and XXI exactly two -L-R″ substituents may be other than H In the case of Formula XXII, exactly one -L-R″ substituent may be other than H.

Any carbocyclic group especially comprises $C_3$, $C_4$, $C_5$, $C_6$ and $C_7$ in ring carbon atoms and may be aromatic (aryl) or non aromatic. Where the carbocycle is non-aromatic, it may be saturated or unsaturated. Especially preferred carbocycles are phenyl, cyclohexyl and cyclopentyl. As indicated above, any carbocyclic group may be substituted by one or more of the substituents as listed under the heading "Substituents".

Any heterocyclic group especially comprises five, six or seven in-ring atoms of which at least one is a heteroatom selected from N, O or S. Especially preferred heterocycles are pyridine, pyrrolidine, pyrazole, thiazole, imidazole, especially 1-imidazole, 1-thia-2,3-diazolyl, piperazine, piperidine, morpholine and 1,1-dioxo-thiomorpholine. As indicated above, any heterocyclic group may be substituted by one or more of the substituents as listed under the heading "Substituents".

In a class of compounds according to the present invention, $R^5$, $R^6$, $R^7$, $R^8$ and $R^9$ are each independently selected from:
  lower alkyl, especially $^tBu$ and $^iPr$, halo, especially chloro or fluoro, halo-lower alkyl, especially trifluoromethyl, lower alkoxy, especially methoxy, halo-lower alkoxy, especially 2,2,2-trifluoroethoxy, acylamino, substituted acylamino, especially dimethyl formamyl (—CO—NMe$_2$), phenyl, substituted phenyl, cyano; amino, hydroxyl, azo (N=N=N), nitro, carbamate, or
  mono- or di-substituted amino, being substituted by a hydrocarbyl moiety, for example lower alkyl, especially $C_1$, $C_2$, $C_3$ or $C_4$ alkyl, cycloalkyl, especially cyclohexyl, phenyl, substituted phenyl; lower alkanoyl, especially acetyl, haloalkyl;
  a heterocyclic group, either substituted or unsubstituted, selected from: furan, thiophene, pyrrole, imidazole, pyrazole, isoxazole, oxazole, thiazole, pyran, pyridazine, indole, isoindole, indazole, purine, indolizidine, quinoline, isoquinoline, quinazoline, pteridine, quinolizidine, pyrimidine, pyrazine, pyridyl, alkyl-pyridyl, piperidyl, especially piperidin-1-yl, especially 4-methyl-piperidin-1-yl, piperazinyl, especially piperazin-1-yl, alkyl-piperazinyl, e.g. 4-methyl, 4-ethyl or 4-$^i$Pr-piperazin-1-yl, pyrollidine, especially dimethyl amino pyrrolidine, morpholinyl or thiomorpholinyl.

In one class of compounds, Ar is of Formula XX:

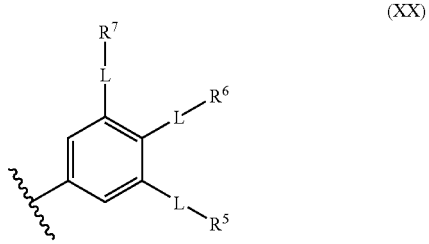

For all compounds according to the invention, although particularly relevant to a class of compounds where Ar is of the formula XX, $R^5$ is commonly selected from $CF_3$, Me, Cl, F, OMe, most commonly $CF_3$. Where $R^5$ is $CF_3$, it is preferred that only one of $R^6$ and $R^7$ is present.

In one embodiment of the present invention X represents $CR^3$ and $R^3$ and $R^1$ together with the carbon atoms to which they are attached form a five- or six-membered unsaturated ring containing at least one nitrogen atom. In such embodiment the five-membered unsaturated ring is preferred and such ring preferably contains exactly one nitrogen atom.

In one selection of compounds from the present invention, either $R^5$ is $CF_3$ and $R^6$ is

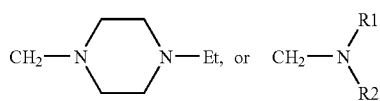

In some compounds of the present invention, one of $R^5$, $R^6$, $R^7$ or $R^8$ is a heterocyclic group, for example a piperazine group or a pyrrolidine group. The piperazine group may be separated from the aromatic ring by a linker, for example by an alkyl linker, for example by —$CH_2$—, thus providing a piperazin-1-ylmethyl group. Separation by an oxygen or nitrogen linker (e.g. —NH—) is also contemplated. The piperazine group may be substituted by, for example an alkyl group, for example methyl, ethyl, propyl, isopropyl, butyl, isobutyl or tertiary butyl, thus providing, by way of example, a 3-(isopropylpiperazin-1-yl)methyl substituent. The pyrrolidine group may be separated from the aryl group by a linker and be substituted by, for example alkyl. An example of a pyrrolidine group would be pyrrolidin-1-ylmethyl. The full list of contemplated substituents is identified under the heading "Substituents".

In some compounds of the present invention, $R^9$ is selected from a substituted or unsubstituted moiety selected from phenyl, pyridyl, pyrrole, imidazole and pyrazole. Any substituent may be selected from the list presented under the heading "Substituents". An exemplary $R^9$ group is p-methyl benzene.

In a first embodiment of the present invention $R^1$ is NHCO—$R^{10}$, which provides compounds of Formula II or salts, esters or prodrugs thereof:

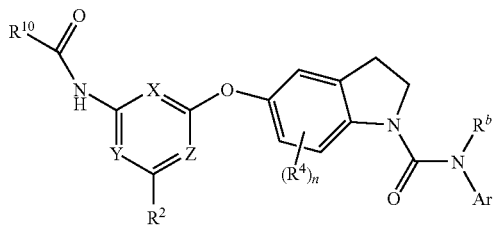

where $R^2$, $R^3$, $R^4$, $R^b$ and Ar are as hereinbefore defined; and $R^{10}$ may be selected from substituted or unsubstituted organic moieties especially selected from lower alkyl, especially $C_1$, $C_2$, $C_3$ or $C_4$ alkyl, lower alkenyl, lower alkynyl, halo-lower alkyl, an ester-forming group such as lower alkoxy, halo-lower alkoxy, mono- or di-substituted amino, phenyl, substituted phenyl; or a heterocyclic group, either substituted or unsubstituted, selected from: furan, thiophene, pyrrole, imidazole, pyrazole, isoxazole, oxazole, thiazole, pyran, pyridazine, indole, isoindole, indazole, purine, indolizidine, quinoline, isoquinoline, quinazoline, pteridine, quinolizidine, pyrimidine, pyrazine, pyridyl, alkyl-pyridyl, piperidyl, especially piperidin-1-yl, especially 4-methyl-piperidin-1-yl, piperazinyl, especially piperazin-1-yl, alkyl-piperazinyl, e.g. 4-methyl, 4-ethyl or 4-$^i$Pr-piperazin-1-yl, pyrollidine, especially dimethyl amino pyrrolidine, morpholinyl, thiomorpholinyl.

A preferred selection of compounds of Formula III are, for example, where $R^2$ and $R^3$ (if present) are independently selected from hydrogen, lower alkyl, amino, cycloalkyl amino, lower alkanoylamino, halo and azo, especially, $R^2$ and $R^3$ are hydrogen.

n is preferably zero.

$R^{10}$ is as previously defined and is most preferably selected from lower alkyl, an ester-forming group (e.g. lower alkoxy), pyridyl, piperidyl, piperidinyl, piperazinyl, alkyl-piperazinyl, pyrollidine, morpholinyl, thiomorpholinyl. $R^{10}$ is more preferably lower-alkyl, e.g. methyl.

In one particular class of compounds, X is $CR^3$ and Y and Z are N. In another class of compounds X and Y are N and Z is $CR^3$. In both classes, $R^3$ is preferably H.

In variants, $R^{10}$CONH—, is replaced by $R^{10}$CONH-alkyl-, where -alkyl is $C_1$-$C_4$ alkyl.

In particular, compounds of Formula II have the general structure of Formula IIA:

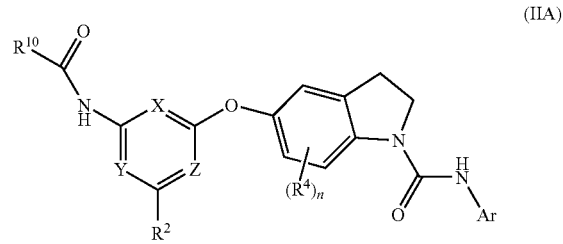

In a further preferred embodiment of Formula II are the compounds of Formula III:

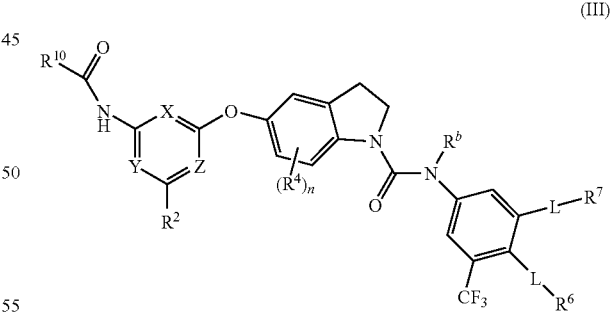

where $R^{10}$ is as previously defined and is most preferably selected from lower alkyl, an ester-forming group (e.g. lower alkoxy), pyridyl, piperidyl, piperidinyl, piperazinyl, alkyl-piperazinyl, pyrollidine, morpholinyl, thiomorpholinyl. $R^{10}$ is more preferably lower-alkyl, e.g. methyl.

$R^6$ and $R^7$ are as previously defined. In a selection of compounds at least one of $R^6$ and $R^7$ is hydrogen. In another selection of compounds at least one of $R^6$ and $R^7$ is selected from cyano, a substituted or unsubstituted heterocyclic group, selected from: pyrrole, imidazole, pyrazole, pyrimidine, pyrazine, pyridyl, pyridyl, alkyl-pyridyl, piperidyl, piperazinyl, alkyl-piperazinyl, pyrollidine, morpholinyl, thiomorpholinyl; the other of $R^6$ and $R^7$ may be hydrogen.

As previously mentioned, $R^6$ and $R^7$ may be bound directly to the ring or may be bound by a linker, L, for example by a —$CH_2$— group or —O—.

A preferred selection of compounds of Formula III are, for example, where $R^2$ and $R^3$ (if present) are independently selected from hydrogen, lower alkyl, amino, cycloalkyl amino, lower alkanoylamino, halo and azo; especially, $R^2$ and $R^3$ are hydrogen.

n is preferably zero.

In particular, compounds of Formula III may have the general structure of Formula IIIA:

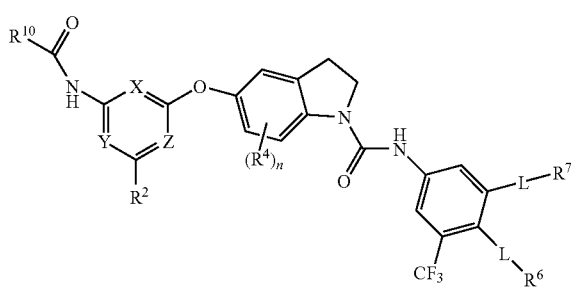

(IIIA)

Particularly preferred substituents for $R^2$ and $R^3$ (if present) are hydrogen and:

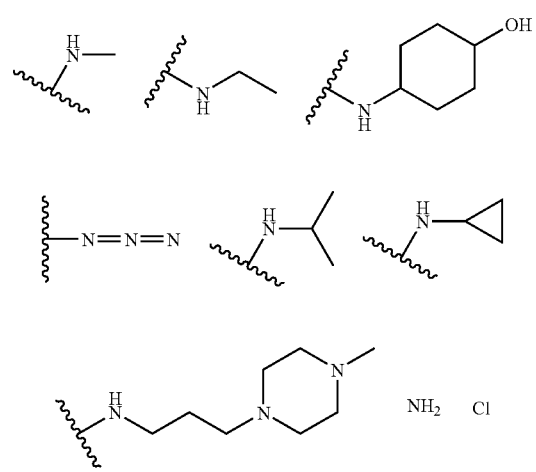

More commonly $R^2$ and $R^3$ (if present) are H.

In a further embodiment of the present invention, in particular of the compounds of Formula I, are the compounds of Formula IV:

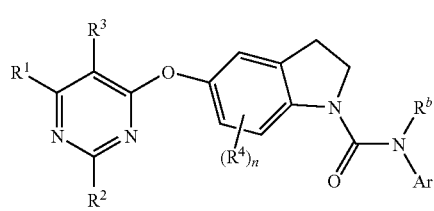

(IV)

A particular sub-class of compounds having the Formula IV are shown below:

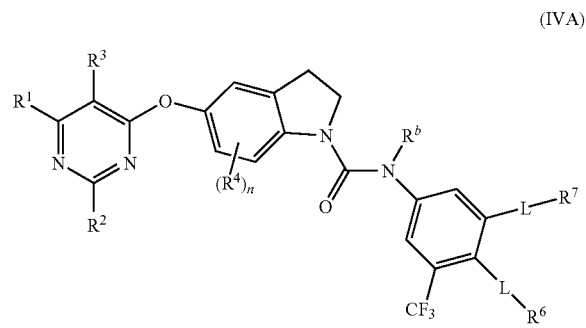

(IVA)

For a class of compounds of the invention, most particularly for compounds of Formula IV, $R^1$ is especially selected from $R^{10}$—CO—NH—, Cl or H and $R^2$ is especially selected from H or $NH_2$. Most especially, when $R^1$ is H, $R^2$ is preferably $NH_2$ or Cl and when $R^2$ is $NH_2$, $R^1$ is H or Cl. $R^3$ is most commonly H.

In particular, compounds of Formula IVA have the general structure of Formula IVB:

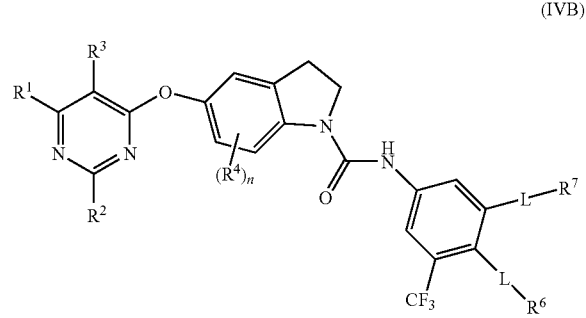

(IVB)

In another embodiment of the present invention, in particular of the compounds of Formula I, there is provided compounds of Formula V:

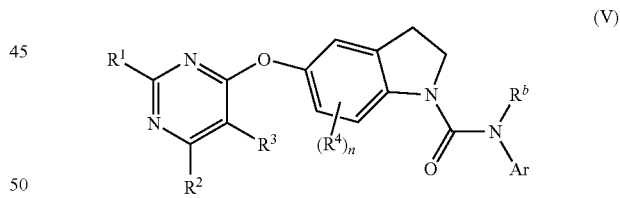

(V)

A particular sub-class of compounds having the Formula V is shown below:

(VA)

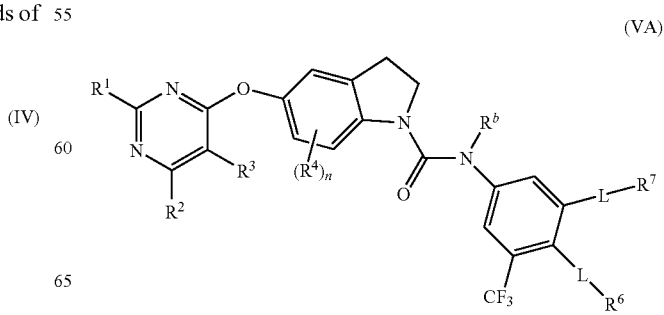

In one class of compounds, at least one of $R^1$, $R^2$ and $R^3$ is selected from hydrogen, halo, amino and mono- or di-substituted amino, the amino optionally being substituted by a hydrocarbyl moiety, the hydrocarbyl moiety being, for example, selected from lower alkyl, especially $C_1$, $C_2$, $C_3$ or $C_4$ alkyl, carboxy, lower alkanoyl, especially acetyl; a carbocyclic group, for example phenyl cycloalkyl, especially cyclohexyl; a heterocyclic group; where the hydrocarbyl moiety is substituted or unsubstituted. Most common is a mono substituted amino group.

For a class of compounds of the invention, most particularly for compounds of Formula V, $R^1$ is especially selected from Cl and H, most commonly H, and $R^2$ and $R^3$ are especially selected from hydrogen and:

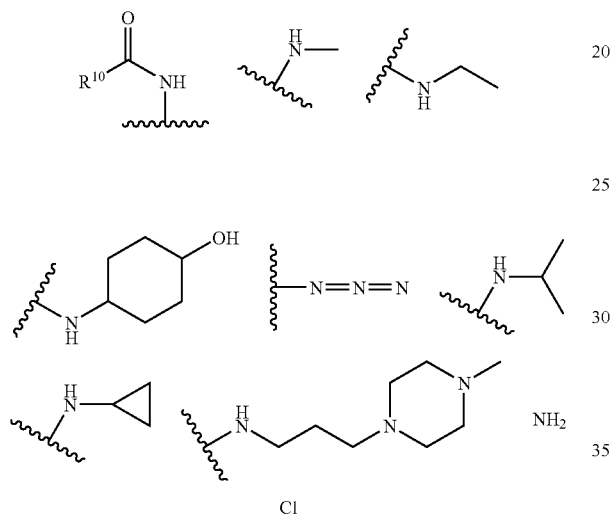

$R^2$ is most especially $NH_2$. $R^3$ is most commonly H.

In particular, compounds of Formula VA have the general structure of Formula VB:

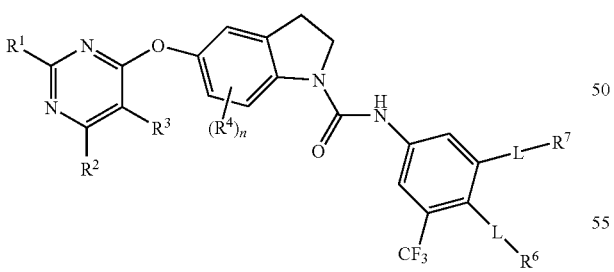

(VB)

The definitions of $R^1$, $R^2$, $R^3$, $R^4$, $R^5$, $R^6$, $R^7$, $R^8$, $R^9$, $R^{10}$, $R^a$ or $R^b$ as hereinbefore described are not limiting, and as such additional contemplated definitions of the aforementioned substituents may be further identified under the heading "Substituents".

For a common class of compounds according to the invention, n is zero and $R^3$, when present, is hydrogen and at least one of $R^7$ and $R^6$ are also hydrogen.

A further class of compounds of the present invention, in particular of the compounds of Formula I have the Formula VI:

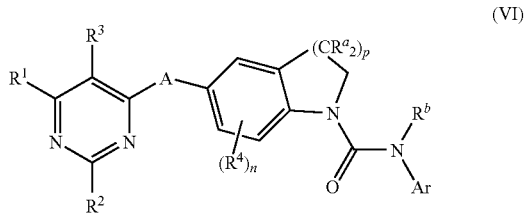

(VI)

Particular examples of compounds of Formula VI are shown below:

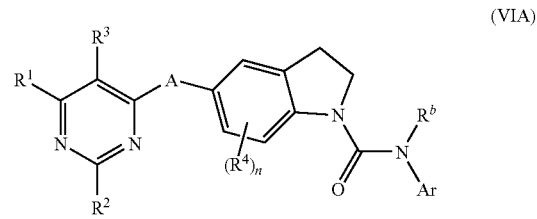

(VIA)

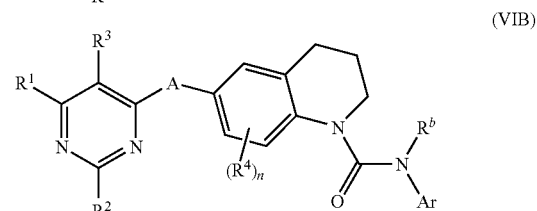

(VIB)

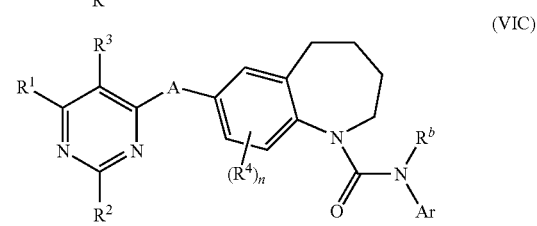

(VIC)

A second further class of compounds of the present invention, in particular of the compounds of Formula I, have the Formula VII:

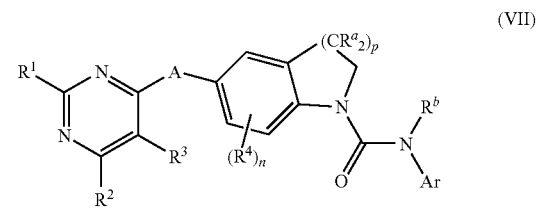

(VII)

Particular examples of compounds of Formula VII are shown below:

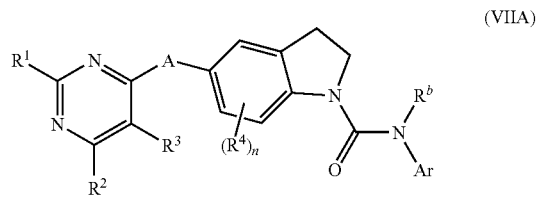

(VIIA)

-continued

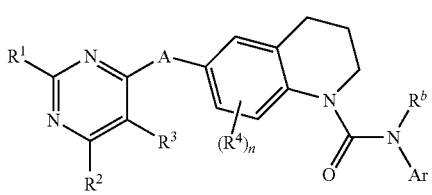
(VIIB)

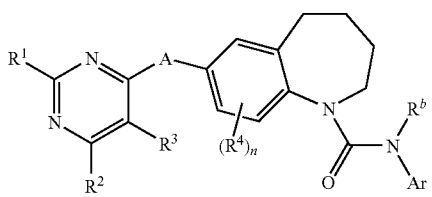
(VIIC)

A third further class of compounds of the present invention, in particular of the compounds of Formula 1, have the Formula VII:

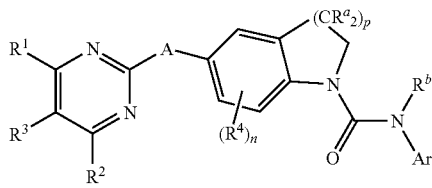
(VIII)

Particular examples of compounds of Formula VIII are shown below:

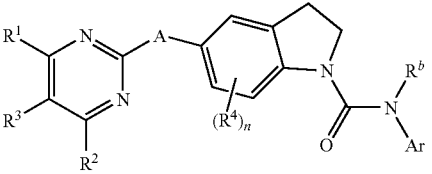
(VIIIA)

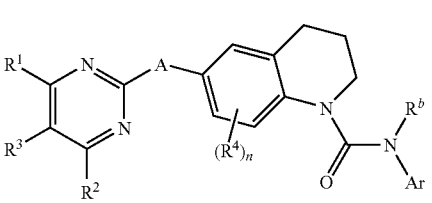
(VIIIB)

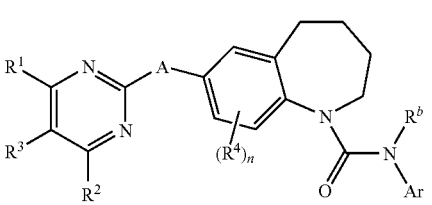
(VIIIC)

A third further class of compounds of the present invention, in particular of the compounds of Formula I, have the Formula IX:

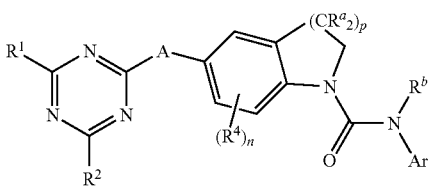
(IX)

Particular examples of compounds of Formula IXI are shown below:

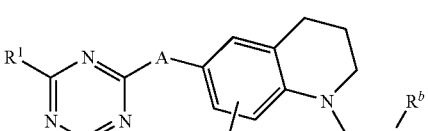
(IXA)

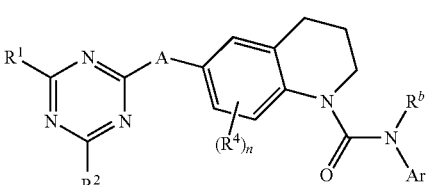
(IXB)

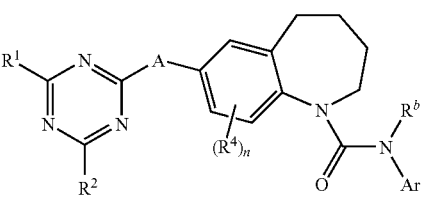
(IXC)

It will be understood that, for the Formulae as hereinbefore illustrated, in particular the Formulae VI, VII, VIII and IX and their examples labelled with suffixes A, B and C, the definitions of the moieties $R^1$, $R^2$, $R^3$, $R^4$, $R^a$, $R^b$, n, p, A and Ar are as previously defined, including any selected groups, classes and sub-classes as hereinbefore described which may relate to these moieties.

It is contemplated that where a direct bond is indicated to an aryl ring, the substituent may be linked to the aryl ring by a linker group, although not specifically shown, such as a lower alkyl group, e.g. in the form of a methyl or ethyl spacer, or alternatively an oxygen, nitrogen or sulphur group, for example.

Substituents

"Substituted", wherever used for a moiety, means that one or more hydrogen atoms in the respective moiety, especially up to 5, more especially 1, 2 or 3 of the hydrogen atoms are replaced independently of each other by the corresponding number of substituents which preferably are independently selected from the group consisting of lower alkyl, for example methyl, ethyl or propyl, halo-lower alkyl, for example trifluoromethyl, $C_6$-$C_{16}$-aryl, especially phenyl pyridine.

$C_6$-$C_{16}$-aryl is unsubstituted or substituted by one or more, especially 1, 2 or 3 moieties selected from, for example, lower alkyl, halogen, carboxy, lower alkoxycarbonyl, hydroxy, etherified or esterified hydroxy, lower alkoxy, phenyl-lower alkoxy, lower alkanoyloxy, lower alkanoyl, amino, mono- or di-substituted amino, halo, halo-lower alkyl, e.g. trifluoromethyl, sulfo, sulfamoyl, carbamoyl, N-mono substituted or N,N-disubstituted carbamoyl, N-lower alkyl-carbamoyl, N-(hydroxy-lower alkyl)-carbamoyl, such as N-(2-hydroxyethyl)-carbamoyl, cyano, cyano-lower alkyl and nitro;

Substituents also include hydroxy, $C_3$-$C_{10}$-cycloalkyl, especially cyclopropyl or cyclohexyl, hydroxy-$C_3$-$C_8$-cycloalkyl, such as hydroxy-cyclohexyl, substituted or unsubstituted heterocyclyl with 5 or 6 ring atoms and I to 3 ring heteroatoms selected from O, N and S, especially piperidinyl, especially piperidin-1-yl, piperazinyl being unsubstituted or substituted by lower alkyl such as iso-propyl or methyl, especially piperazin-1-yl and 4-me-thyl-piperazin-1-yl, morpholinyl, especially morpholin-1-yl, hydroxy, lower alkoxy, for example methoxy, halo-lower alkoxy, especially 2,2,2-trifluoroethoxy, phenyl-lower alkoxy, phenoxy, amino-lower alkoxy, such as 2-eminoethoxy; lower alkanoyloxy, hydroxy-lower alkyl, such as hydroxymethyl or 2-hydroxyethyl, amino, mono- or di-substituted amino, carbamoyl-lower alkoxy, N-lower alkylcarbamoyl-lower alkoxy or N,N-di-lower alkylcarbamoyl-lower alkoxy, amidino, ureido, mercapto, N-hydroxy-amidino, guanidino, amidino-lower alkyl, such as 2-amidinoethyl, N-hydroxyami-dino-lower alkyl, such as N-hydroxy-amidino-methyl or -2-ethyl, halogen, for example fluoro, chloro, bromo or iodo, carboxy, esterified carboxy, lower alkoxycarbonyl, phenyl-, naphthyl- or fluorenyl-lower alkoxycarbonyl, such as benzyloxycarbonyl, benzoyl, lower alkanoyl, sulfo, lower alkanesulfonyl, for example methanesulfo-nyl ($CH_3$—$S(O)_2$—), lower alkylthio, phenylthio, phe-nyl-lower alkylthio, lower alkylphenylthio, lower alkyl-sulfinyl, phenylsulfinyl, phenyl-lower alkylsulfinyl, lower alkylphenylsulfinyl, halogen-lower alkylmer-capto, halogen-lower alkylsulfonyl, such as especially trifluoromethanesulfonyl, dihydroxybora (—$B(OH)_2$), phosphono (—$P(=O)(OH)_2$), hydroxy-lower alkoxy phosphoryl or di-lower alkoxyphosphoryl, carbamoyl, mono- or di-lower alkylcarbamoyl, mono- or di-(hy-droxy-lower alkyl)-carbamoyl, sulfamoyl, mono- or di-lower alkylaminosulfonyl, nitro, cyano-lower alkyl, such as cyanomethyl, cyano, lower alkenyl, lower alky-nyl and methylendioxy.

It goes without saying that substituents are only at positions where they are chemically possible, the person skilled in the art being able to decide (either experimentally or theoretically) without inappropriate effort which substitutions are possible and which are not. For example, amino or hydroxy groups with free hydrogen may be unstable if bound to carbon atoms with unsaturated (e.g. olefinic) bonds. Additionally, it will of course be understood that the substituents as listed above may themselves be substituted by any substituent, subject to the aforementioned restriction to appropriate substitutions as recognised by the skilled man.

Other Definitions

The general terms used hereinbefore and hereinafter preferably have within the context of this disclosure the following meanings, unless otherwise indicated:

The prefix "lower" denotes a radical having up to and including a maximum of 7 in-chain atoms, especially up to and including a maximum of 4 in-chain atoms. A particular class of alkyl comprises a maximum of 4 carbon atoms. The radicals in question being either linear or branched with single or multiple branching.

Lower alkyl is preferably alkyl with from and including 1 up to and including 7 carbon atoms, preferably from and including 1, 2, 3 or 4 carbon atoms, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl, propyl or tert-butyl.

Where the plural form is used for compounds, salts, and the like, this is taken to mean also a single compound, salt, or the like.

Any asymmetric carbon atoms may be present in the (R)—, (S)— or (R,S)-configuration, preferably in the (R)— or (S)-configuration. Radicals having any unsaturation are present in cis-, trans- or (cis, trans) form. The compounds may thus be present as mixtures of isomers or as pure isomers, preferably as enantiomer-pure diastereomers.

The invention relates also to possible tautomers of the disclosed compounds.

In view of the close relationship between the diaryl urea derivatives in free form and in the form of their salts, including those salts that can be used as intermediates, for example in the purification or identification of the novel compounds, tautomers or tautomeric mixtures and their salts, any reference hereinbefore and hereinafter to these compounds, especially the compounds of the Formula I, II, III, IV, V, VI, VII, VIII or IX (or exemplary formula thereof), is to be understood as referring also to the corresponding tautomers of these compounds, especially of compounds of the Formula I, II, III, IV, V, VI, VII, VIII or IX (or exemplary formula thereof), tautomeric mixtures of these compounds, especially of compounds of the Formula I, II, III, IV, V, VI, VII, VIII or IX (or exemplary formula thereof), or salts of any of these, as appropriate and expedient and if not mentioned otherwise.

Tautomers can, e.g., be present in cases where amino or hydroxy, each with a least one bound hydrogen, are bound to carbon atoms that are bound to adjacent atoms by double bonds (e.g. keto-enol or imine-enamine tautomerism). Preferred tautomers are the pyridin-on-yl or pyrimidin-on-yl forms of compounds wherein $R^1$ or $R^2$ is hydroxy and the other moieties are defined as for compounds of the Formula I, II, III, IV, V, VI, VII, VIII or IX (or exemplary formula thereof), respectively.

Where "a compound . . . , a tautomer thereof; or a salt thereof" or the like is mentioned, this means "a compound . . . , a tautomer thereof, or a salt of the compound or the tautomer".

By acyl is meant an organic radical derived from, for example, an organic acid by the removal of the hydroxyl group, i.e., a radical having the formula R—C(O)—, where R may be selected from lower $C_1$-$C_6$ alkyl, $C_3$-$C_7$ cycloalkyl, phenyl, benzyl or phenethyl group. Acyl is alkyl-carbonyl. Examples of acyl groups, include, but are not limited to, formyl, acetyl, propionyl and butyryl. Lower acyl is preferably formyl or lower alkylcarbonyl, in particular acetyl.

Alkyl preferably has up to 20, more preferably up to 12 carbon atoms and is linear or branched one or more times a; preferred is lower alkyl, especially $C_1$-$C_4$-alkyl, in particular methyl, ethyl or i-propyl or t-butyl. Where alkyl may be substituted by one or more substituents independently selected from those mentioned above under the title "Substituents". Unsubstituted alkyl, preferably lower alkyl, is especially preferred. The term alkyl also encompasses cycloalkyl as defined further below:

Alkyl may be optionally interrupted by one or more in-chain heteroatoms, for example —O—, thus forming, for example, an ether linkage.

Cycloalkyl is preferably $C_3$-$C_{10}$-cycloalkyl, especially cyclopropyl, dimethylcyclopropyl, cyclobutyl, cyclopentyl, cyclohexyl or cycloheptyl, cycloalkyl being unsubstituted or substituted by one or more, especially 1, 2 or 3, substituents independently selected from the group consisting of the substituents defined above under the title "Substituents".

Substituted alkyl is alkyl as last defined, especially lower alkyl, preferably methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred. One class of compounds includes a substituted alkyl where the alkyl is substituted with a heterocyclic ring, for example a pyrazine ring, thus forming an alkylene-het group, i.e. —CH$_2$-Het, the alkyl group effectively acting as a linker between the heterocycle and a second moiety.

Among the moieties corresponding to substituted alkyl, hydroxy-lower alkyl, especially 2-hydroxyethyl, and/or halo-lower alkyl, especially trifluoromethyl or 2,2,2-trifluoroethyl, are especially preferred.

Alkenyl may have one or more double bonds and preferably has 2 to 20, more preferably up to 12, carbon atoms; it is linear or branched one or more times (as far as possible in view of the number of carbon atoms). Preferred is $C_2$-$C_7$-alkenyl, especially $C_3$ or $C_4$-alkenyl, such as allyl or crotyl. Alkenyl can be unsubstituted or substituted, especially by one or more, more especially up to three, of the substituents mentioned above under "the title "Substituents". Substituents such as amino or hydroxy (with free dissociable hydrogen) preferably are not bound to carbon atoms that participate at a double bond, and also other substituents that are not sufficiently stable are preferably excluded. Unsubstituted alkenyl, in particular $C_2$-$C_7$-alkenyl, is preferred.

Alkynyl is preferably a moiety with one or more triple bonds and preferably has 2 to 20, more preferably up to 12, carbon atoms; it is linear of branched one or more times (as far as possible in view of the number of carbon atoms). Preferred is $C_2$-$C_7$-alkynyl, especially $C_3$ or $C_4$-alkynyl, such as ethinyl or propin-2-yl. Alkynyl can be unsubstituted or substituted, especially by one or more, more especially up to three, of the substituents mentioned above under the title "Substituents". Substituents such as amino or hydroxy (with free dissociable hydrogen) preferably are not bound to carbon atoms that participate at a triple bond, and also other substituents that are not sufficiently stable are preferably excluded. Unsubstituted alkynyl, in particular $C_2$-$C_7$-alkynyl, is preferred.

An aryl group is an aromatic radical and may be heterocyclic or carbocyclic. Preferably, aryl is carbocyclic and is bound to the molecule via a bond located at an aromatic ring carbon atom of the radical (or optionally bound via a linking group, such as —O— or —CH$_2$—). Preferably aryl has a ring system of not more than 16 carbon atoms and is preferably mono- bi- or tri-cyclic and may be fully or partially substituted, for example substituted by at least two substituents. Preferably, aryl is selected from phenyl, naphthyl, indenyl, azulenyl and anthryl, and is preferably in each case unsubstituted or lower alkyl, especially methyl, ethyl or n-propyl, halo (especially fluoro, chloro, bromo or iodo), halo-lower alkyl (especially trifluoromethyl), hydroxy, lower alkoxy (especially methoxy), halo-lower alkoxy (especially 2,2,2-trifluoroethoxy), amino-lower alkoxy (especially 2-amino-ethoxy), lower alkyl (especially methyl or ethyl) carbamoyl, N-(hydroxy-lower alkyl)-carbamoyl (especially N-(2-hydroxyethyl)-carbamoyl) and/or sulfamoyl-substituted aryl, especially a corresponding substituted or unsubstituted phenyl. Also, heterocyclic groups can be mentioned here, as defined below.

Any carbocyclic group especially comprises 3, 4, 5, 6 or 7 in ring carbon atoms and may be aromatic (aryl) or non aromatic. Where the carbocycle is non-aromatic, it may be saturated or unsaturated. Especially preferred carbocycles are phenyl, cyclohexyl and cyclopentyl.

Heterocyclyl (or heterocyclic group) is preferably a heterocyclic radical that is unsaturated, saturated or partially saturated and is preferably a monocyclic or in a broader aspect of the invention bicyclic or tricyclic ring; has 3 to 24, more preferably 4 to 16 ring atoms. Heterocycles may contain one or more, preferably one to four, especially one or two ring-forming heteroatoms selected from the group consisting of nitrogen, oxygen and sulfur, the ring preferably having 4 to 12, especially 5 to 7 ring atoms. Heterocycles may be unsubstituted or substituted by one or more, especially 1 to 3, substituents independently selected from the group consisting of the substituents defined above under the tile "Substituents". Heterocycle especially is a radical selected from the group consisting of oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, pyranyol, thiazolyl, isothiazolyl, dithiazolyl, oxazolyl, isoxazolyl, pyridyl, pyrazinyl, pyrimidinyl, piperidyl, especially piperidin-1-yl, piperazinyl, especially piperazin-1-yl, pyridazinyl, morpholinyl, especially morpholino, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl and chromanyl, each of these radicals being unsubstituted or substituted by one to two radicals selected from the group consisting of lower alkyl, especially methyl or tert-butyl, lower alkoxy, especially methoxy, and halo, especially bromo or chloro. Unsubstituted heterocyclyl, especially piperidyl, piperazinyl, thiomorpholino or morpholino, is preferred.

Any heterocyclic group especially comprises five or six in-chain atoms of which at least one is a heteroatom selected from N, O or S. Especially preferred heterocycles are pyridine, pyrrolidine, piperidine and morpholine.

Mono- or disubstituted amino may be an amino group substituted by one or more of the substituents as listed under the heading "Substituents" and may form a secondary or tertiary amine group and/or is especially an amino and having the formula $NR^k_2$, $NR^kOH$, $NR^kCOR^k$ (e.g. NHCO-alkyl), $NR^kCOOR^k$ (e.g $NR^kCOO$-alkyl), $NR^kC(NR^k)H$ (e.g. NHC(NH)H), $NR^kC(NR^k)NR^kOH$ (e.g. NHC(NH)NHOH), $NR^kC(NR^k)NR^kCN$, (e.g. NHC(NH)NHCN), $NR^kC(NR^k)NR^k$-$COR^k$, (e.g. $NHC(NH)NHCOR^k$), $NR^kC(NR^k)NR^kR^2$, (e.g. $NHC(NH)NHR^k$), $N(COOR^k)C(NH_2)$=$NCOOR^k$, (e.g. $N(COOR^k)C(NH_2)$=$NCOOR^k$), where each $R^k$ is independently selected from the substituents as listed under the heading "Substituents" and may especially be selected from hydrogen, hydroxy, alkyl, substituted alkyl, lower alkyl, such as methyl; hydroxy-lower alkyl, such as 2-hydroxyethyl; halo-lower alkyl, lower alkoxy lower alkyl, such as methoxy ethyl; alkenyl, substituted alkenyl, alkynyl, substituted alkynyl, aryl, cycloalkyl, substituted cycloalkyl, heteroaryl, heterocyclyl, lower alkanoyl, such as acetyl; benzoyl; substituted benzoyl, phenyl, phenyl-lower alkyl, such as benzyl or 2-phenylethyl. Any $R^k$ group may be substituted by the substituents as defined under the heading "Substituents" and the substituents may be selected from, preferably one or two of, nitro, amino, halogen, hydroxy, cyano, carboxy, lower alkoxycarbonyl, lower alkanoyl, and carbamoyl; and phenyl-lower alkoxycarbonyl.

As such, exemplary substituted amino groups are N-lower alkylamino, such as N-methylamino, N,N-di-lower alkylamino, N-lower alkylaminoamino-lower alkyl, such as aminomethyl or 2-aminoethyl, hydroxy-lower alkylamino, such as 2-hydroxy-ethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, benzoylamino, phenyl-lower alkoxycarbonylamino, carbamoyl or aminocarbonylamino, amino-lower alkyl-oxyphenyl-amino, sulfamoylphenylamino, [N-(hydroxy-lower alkyl)-carbamoyl]-phenylamino. An example of a substituted amino is an amino substituted by a 4-substituted cyclohexyl, for example cyclohexan-4-ol.

Disubstituted amino may also be lower alkylene-amino, e.g. pyrrolidino, 2-oxopyrrolidino or piperidino; lower oxaalkylene-amino, e.g. morpholino, or lower azaalkylene-amino, e.g. piperazino or N-substituted piperazino, such as N-methylpiperazine, N-methoxycarbonylpiperazino, N-mono substituted or N,N-disubstituted carbamoyl, N-lower alkyl-carbamoyl or N-(hydroxy-lower alkyl)-carbamoyl, such as N-(2-hydroxyethyl)-carbamoyl. It is also contemplated that an alkanoylamino extends to a carbamate, such as carbamic acid methyl ester.

Halogen (halo) is especially fluorine, chlorine, bromine, or iodine, especially fluorine, chlorine, or bromine most especially chlorine or fluorine.

Etherified hydroxy is especially $C_8$-$C_{20}$alkyloxy, such as n-decyloxy, lower alkoxy (preferred), such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bicyclic heteroaryl comprising one or two nitrogen atoms, preferably lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, iso-propoxycarbonyl, methoxycarbonyl or ethoxycarbonyl, phenyl-lower alkoxycarbonyl, or phenyloxycarbonyl.

Alkanoyl is alkylcarbonyl, especially lower alkanoyl, e.g. acetyl. The alkyl part of the alkanoyl group may be substituted to form a moiety $R^{10}$.

N-Mono- or N,N-disubstituted carbamoyl is especially substituted by one or two substituents independently selected from lower alkyl, phenyl-lower alkyl and hydroxy-lower alkyl, or lower alkylene, oxa-lower alkylene or aza-lower alkylene optionally substituted at the terminal nitrogen atom.

Salts are especially the pharmaceutically acceptable salts of compounds of Formula I, II, III, IV, V, VI, VII, VIII or IX (or exemplary formula thereof), especially if they are forming salt-forming groups.

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, hetero-aromatic carboxylic acids, such as nicotinic acid or isonicotinic acid, aliphatic sulfonic acids, such as methane-, ethane- or 2-hydroxyethanesulfonic acid, or aromatic sulfonic acids, for example benzene-, p-toluene- or naphthalene-2-sulfonic acid. When several basic groups are present mono- or poly-acid addition salts may be formed.

Compounds having acidic groups, a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

Such salts are formed, for example, as acid addition salts, preferably with organic or inorganic acids, from compounds of Formula I, II, III, IV, V, VI, VII, VIII or IX (or exemplary formula thereof) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of Formula I, II, III, IV, V, VI, VII, VIII or IX (or exemplary formula thereof) may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of Formula I, II, III, IV, V, VI, VII, VIII or IX (or exemplary formula thereof) and N-oxides thereof have valuable pharmacological properties, as described hereinbefore and hereinafter.

Biology

The efficacy of the compounds of the invention as inhibitors of c-Abl, Bcr-Abl, and VEGF-receptor tyrosine kinase activity can be demonstrated as follows:

Test for activity against c-Abl protein tyrosine kinase:

The test, an in vitro enzyme assay, is conducted as a filter binding assay as follows:

The His-tagged kinase domain of c-Abl is cloned and expressed in the baculovirus/Sf9 system as described by Bhat et al., J Biol Chem. 272, 16170-5 (1997). A protein of 37 kD (c-Abl kinase) is purified by a two-step procedure over a Cobalt metal chelate column followed by an anion exchange column with a yield of 1-2 mg/L of Sf9 cells. The purity of the c-Abl kinase is >90% as judged by SDS-PAGE after Coomassie blue staining. The assay contains: c-Abl kinase (50 ng), 20 mM Tris·HCl, pH 7.5, 10 mM $MgCl_2$, 10 µM $Na_3VO_4$, 1 mM DTT and 0.06 µCi/assay [$\gamma^{33}$ P]-ATP (5 µM ATP) using 30 µg/mL poly-Ala,Glu,Lys,Tyr-6:2:5:1 (Poly-AEKY, Sigma P1152) in the presence of 1% DMSO, total volume of 30 µL. Reactions are terminated by adding 10 µL of 250 mM EDTA, and 30 µL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µL 0.5% $H_3PO_4$. Membranes are removed and washed on a shaker with 0.5% $H_3PO_4$ (4 times) and once with ethanol. Membranes are counted after drying at ambient temperature, mounting in Packard TopCount 96-well frame, and addition of 10 µL/well of Microscint™ (Packard). Using this test system, compounds of the invention show $IC_{50}$ values in the range 11 nM to 600 nM, usually from 11 nM to 60 nM.

The compounds of the invention here preferably show $IC_{50}$ values below 250 nM for inhibition of autophosphorylation and inhibition of IL-3 independent proliferation of Abl mutants in particular T315I.

Test for activity against Bcr-Abl:

The murine myeloid progenitor cell line 32Dcl3 transfected with the p210 Bcr-Abl expression vector pGDp210Bcr/Abl (32D-bcr/abl) was obtained from J. D. Griffin (Dana Faber Cancer Institute, Boston, Mass., USA). The cells express the fusion Bcr-Abl protein with a constitutively active Abl kinase and proliferate growth factor independent. The cells are expanded in RPMI 1640 (AMIMED), 10% fetal calf serum (FCS), 2 mM glutamine (Gibco) ("complete medium"), and a working stock is prepared by freezing aliquots of $2 \times 10^6$ cells per vial in freezing medium (95% FCS, 5% DMSO (SIGMA)). After thawing, the cells are used during maximally 10-12 passages for the experiments. The antibody anti-Abl SH3 domain cat. #06-466 from Upstate Biotechnology is used for the ELISA. For detection of Bcr-Abl phosphorylation, the anti-phosphotyrosine antibody Ab PY20, labelled with alkaline phosphatase (PY10(AP)) from ZYMED (cat. #03-7722) is used. As comparison and reference compound, (N-{5-[4-(4-methyl-piperazino-methyl)-benzoylamido]-2-methylphenyl}-4-(3-pyridyl)-2-pyrimidine-amine, in the form of the methane sulfonate (monomesylate) salt (STI571) (marketed as Gleevec® or Glivec®, Novartis), is used. A stock solution of 10 mM is prepared in DMSO and stored at –20° C. For the cellular assays, the stock solution is diluted in complete medium in two steps (1:100 and 1:10) to yield a starting concentration of 10 µM followed by preparation of serial three-fold dilutions in complete medium. No solubility problems are encountered using this procedure. The test compounds are treated analogously. For the assay, 200'000 32D-bcr/abl cells in 50 µL are seeded per well in 96 well round bottom tissue culture plates. 50 µL per well of serial threefold dilutions of the test compound are added to the cells in triplicates. The final concentration of the test compound range e.g. from 5 µM down to 0.01 µM. Untreated cells are used as control. The compound is incubated together with the cells for 90 min at 37° C., 5% $CO_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 µl lysis buffer (50 mM Tris/HCl, pH 7.4, 150 mM sodium chloride, 5 mM EDTA, 1 mM EGTA, 1% NP-40 (non-ionic detergent, Roche Diagnostics GmbH, Mannheim, Germany), 2 mM sodium ortho-vanadate, 1 mM phenylmethyl sulfonylfluoride, 50 µg/mL aprotinin and 80 µg/mL leupeptin) and either used immediately for the ELISA or stored frozen at –20° C. until usage. The anti-abl SH3 domain antibody is coated at 200 ng in 50 µL PBS per well to black ELISA plates (Packard HTRF-96 black plates; 6005207) overnight at 4° C. After washing 3× with 200 µL/well PBS containing 0.05% Tween 20 (PBST) and 0.5% TopBlock (Juro, Cat. # TB 232010), residual protein binding sites are blocked with 200 µl/well PBST, 3% TopBlock for 4 h at room temperature, followed by incubation with 50 µl lysates of untreated or test compound-treated cells (20 µg total protein per well) for 3-4 h at 4° C. After 3× washing, 50 µL/well PY20(AP) (Zymed) diluted to 0.5 µg/ml in blocking buffer is added and incubated overnight (4° C.). For all incubation steps, the plates are covered with plate sealers (Costar, cat. #3095). Finally, the plates are washed another three times with washing buffer and once with deionized water before addition of 90 µL/well of the AP substrate CPDStar RTU with Emerald II. The plates now sealed with Packard Top Seal™-A plate sealers (cat. #6005185) are incubated for 45 min at room temperature in the dark and luminescence is quantified by measuring counts per second (CPS) with a Packard Top Count Microplate Scintillation Counter (Top Count). For the final optimized version of the ELISA, 50 µL of the lysates of the cells grown, treated and lysed in 96 well tissue culture plates, are transferred directly from these plates to the ELISA plates that are precoated with 50 ng/well of the rabbit poylclonal ant-Abl-SH3 domain AB 06-466 from Upstate. The concentration of the anti-phosphotyrosine AB PY20 (AP) can be reduced to 0.2 µg/mL. Washing, blocking and incubation with the luminescent substrate are as above. The quantification is achieved as follows: The difference between the ELISA readout (CPS) obtained for with the lysates of the untreated 32D-bcr/abl cells and the readout for the assay background (all components, but without cell lysate) is calculated and taken as 100% reflecting the constitutively phosphorylated Bcr-Abl protein present in these cells. The activity of the compound in the Bcr-Abl kinase activity is expressed as percent reduction of the Bcr-Abl phosphorylation. The values for the $IC_{50}$ are determined from the dose response curves by graphical inter- or extrapolation. The compounds of the invention here preferably show $IC_{50}$ values in the range from 15 nM to 500 µM, most preferably 15 nM to 200 µM.

For cellular assays, compounds are dissolved in DMSO and diluted with complete medium to yield a starting concentration of 10 µM followed by preparation of serial 3-fold dilutions in complete medium. 32D or Ba/F3 cells expressing either 'wt'-Bcr-Abl or Bcr-Abl mutants (e.g. T-315-I) were seeded at 200'000 cells in 50 µL complete medium are seeded per well in 96 well round bottom tissue culture plates. 50 µL per well of serial 3-fold dilutions of the test compound are added to the cells in triplicates. Untreated cells are used as control. The compound is incubated together with the cells for 90 min at 37° C., 5% $CO_2$, followed by centrifugation of the tissue culture plates at 1300 rpm (Beckmann GPR centrifuge) and removal of the supernatants by careful aspiration taking care not to remove any of the pelleted cells. The cell pellets are lysed by addition of 150 µL lysis buffer (50 mM Tris/HCl, pH 7.4, 150 mM sodium chloride, 5 mM EDTA, 1 mM EGTA, 1% NP-40, 2 mM sodiumn ortho-vanadate, 1 mM PMSF, 50 µg/mL aprotinin and 80 µg/mL leupeptin) and either used immediately for the ELISA or stored frozen in the plates at −20° C. until usage.

The rabbit polyclonal anti-Abl-SH3 domain Ab 06466 from Upstate was coated at 50 ng in 50 µl PBS per well to black ELISA plates (Packard HTRF-96 black plates; 6005207) over night at 4° C. After washing 3 times with 200 µL/well PBS containing 0.05% Tween20 (PBST) and 0.5% TopBlock (Juro), residual protein binding sites are blocked with 200 µL/well PBST, 3% TopBlock for 4 h at room temperature followed by incubation with 50 L lysates of untreated or compound-treated cells (20 µg total protein per well) for 3-4 h at 4° C. After 3 washings, 50 µL/well anti-phosphotyrosine Ab PY20(AP) labeled with alkaline phosphatase (Zymed) diluted to 0.2 µg/mL in blocking buffer is added and incubated over night (4° C.). For all incubation steps the plates are covered with plate sealers (Costar). Finally, the plates are washed another three times with washing buffer and once with deionized water before addition of 90 µL/well of the AP-substrate CDPStar RTU with Emerald II. The plates, now sealed with Packard TopSeal™-A plate sealers, are incubated for 45 min at room temperature in the dark and luminescence is quantified by measuring counts per second (CPS) with a Packard Top Count Microplate Scintillation Counter (Top Count).

The difference between the ELISA-readout (CPS) obtained for with the lysates of the untreated 32D-Bcr/Abl cells and the readout for the assay-background (all components, but without cell lysate) is calculated and taken as 100% reflecting the constitutively phosphorylated Bcr-Abl protein present in these cells. The activity of the compound on the Bcr-Abl kinase activity is expressed as percent reduction of the Bcr-Abl phosphorylation. The values for the $IC_{50}$ (and $IC_{90}$) are determined from the dose response curves by graphical extrapolation.

The compounds of the invention here preferably show $IC_{50}$ values below 500 nM for inhibition of autophosphorylation and inhibition of IL-3 independent proliferation of Bcr-Abl mutants in Ba/F3 transfected cells, in particular T315I.

The 32D cl3 cells were obtained from the American Type Culture Collection (ATCC CRL11346) and the Ba/F3 cells from the German Collection of Microorganisms and Cell Cultures (DSMZ, Braunschweig and DSMZ No. ACC 300)

Palacios et al., *Nature,* 1984;309:126.

Palacios et al., *Cell,* 1985:41: 727

The Ba/F3.p210 cells and the murine hematopoietic 32D cl3cells, (32D p210 cells) were obtained by transfecting the IL-3-dependent murine hematopoietic Ba/F3 cell line with a pGD vector containing p210BCR-ABL (B2A2) cDNA.

Daley, G.Q., Baltimore, D. (1988) Transformation of an interleukin 3-dependent hematopoietic cell line by the chronic myeloid leukemia-specific p210 BCR-ABL protein. *PNAS* 1988;85:9312-9316

Sattler M, Salgia R, Okuda K, Uemura N, Durstin M A, Pisick E, et al. The proto-oncogene product p120CBL and the adaptor proteins CRKL and c-CRK link c-ABL, p190BCR-ABL and p210BCR-ABL to the phosphatidylinositol-3' kinase pathway. *Oncogene* 1996;12: 839-46.

Okuda K, Golub T R, Gilliland D G, Griffin J D. p210BCR-ABL, p190BCR-ABL, and TEL/ABL activate similar signal transduction pathways in hematopoietic cell lines. *Oncogene* 1996;13:1147-52.

The inhibition of VEGF-induced receptor autophosphorylation can be confirmed with a further in vitro experiments in cells such as transfected CHO cells, which permanently express human VEGF-R2 receptor (KDR), are seeded in complete culture medium (with 10% FCS) in 96-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After two hours of incubation at 37° C., recombinant VEGF is added; the final VEGF concentration is 20 ng/mL. After a further five minutes incubation at 37° C., the cells are washed twice with ice-cold PBS (phosphate-buffered saline) and immediately lysed in 100 µL lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the VEGF-R2 phosphorylation: a monoclonal antibody to VEGF-R2 (for example Mab 1495.12.14; prepared by H. Towbin, Novartis or comparable monoclonal antibody) is immobilized on black ELISA plates (OptiPlate™ HTRF-96 from Packard). The plates are then washed and the remaining free protein-binding sites are saturated with 3% TopBlock® (Juro, Cat. # TB232010) in phosphate buffered saline with Tween 20® (polyoxyethylen(20)-sorbitane monolaurate, ICI/Uniquema) (PBST). The cell lysates (20 µg protein per well) are then incubated in these plates overnight at 4° C. together with an anti-phosphotyrosine antibody coupled with alkaline phosphatase (PY20:AP from Zymed). The (plates are washed again and the) binding of the antiphosphotyrosine antibody to the captured phosphorylated receptor is then demonstrated using a luminescent AP substrate (CDP-Star, ready to use, with Emerald II; Applied Biosystems). The luminescence is measured in a Packard Top Count Microplate Scintillation Counter. The difference between the signal of the positive control (stimulated with VEGF) and that of the negative control (not stimulated with VEGF) corresponds to VEGF-induced VEGF-R2 phosphorylation (=100%). The activity of the tested substances is calculated as percent inhibition of VEGF-induced VEGF-R2 phosphorylation, wherein the concentration of substance that induces half the maximum inhibition is defined as the $IC_{50}$ (inhibitory dose for 50% inhibition).

On the basis of the inhibitory studies hereinbefore described, a compound of Formula I, II, III, IV, V, VI, VII, VIII or IX (or exemplary formula thereof) according to the invention shows therapeutic efficacy especially against disorders dependent on protein kinase, especially proliferative diseases.

For example, as inhibitors of VEGF-receptor tyrosine kinase activity, the compounds of the invention may primarily inhibit the growth of blood vessels and are thus, for example, effective against a number of diseases associated with deregulated angiogenesis, especially diseases caused by ocular neovascularisation, especially retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, diabetes, endometriosis, chronic asthma, and especially neoplastic diseases (solid tumors, but also leukemias and other "liquid tumors", especially those expressing c-Kit, KDR, Flt-1 or Flt-3), such as especially breast cancer, cancer of the colon, lung cancer (especially small-cell lung cancer), cancer of the prostate or Kaposi's sarcoma. A compound of Formula I, II, III, IV, V, VI, VII, VIII or IX (or exemplary formula thereof) (or an N-oxide thereof) inhibits the growth of tumours and is especially suited to preventing the metastatic spread of tumors and the growth of micrometastases.

The diaryl urea derivatives useful according to the invention, especially compounds of Formula I, II, III, IV, V, VI, VII, VII or IX (or exemplary formula thereof), that inhibit the protein kinase activities mentioned, especially tyrosine protein kinases mentioned above and below, can therefore be used in the treatment of protein kinase dependent diseases. Protein kinase dependent diseases are especially proliferative diseases, preferably benign or especially malignant tumours (for example carcinoma of the kidneys, liver, adrenal glands, bladder, breast, stomach, ovaries, colon, rectum, prostate, pancreas, lungs, vagina or thyroid, sarcoma, glioblastomas and numerous tumours of the neck and head, as well as leukemias). They are able to bring about the regression of tumours and to prevent the formation of tumour metastases and the growth of (also micro)metastases. In addition they can be used in epidermal hyperproliferation (e.g. psoriasis), in prostate hyperplasia, and in the treatment of neoplasias, especially of epithelial character, for example mammary carcinoma. It is also possible to use the compounds of Formula I, II, III, IV, V, VI, VII, VIII or IX (or exemplary formula thereof) in the treatment of diseases of the immune system insofar as several or, especially, individual tyrosine protein kinases are involved; furthermore, the compounds of Formula I, II, III, IV, V, VI, VII, VIII or IX (or exemplary formula thereof) can be used also in the treatment of diseases of the central or peripheral nervous system where signal transmission by at least one tyrosine protein kinase, especially selected from those mentioned specifically, is involved.

Vascular endothelial growth factor receptor-2 (VEGF-R2; KDR) is selectively expressed on the primary vascular endothelium and is essential for normal vascular development. In order to grow beyond minimal size, tumors must generate new vascular supply. Angiogenesis, or the sprouting of new blood vessels, is a central process in the growth of solid tumors. For many cancers, the extent of vascularization of a tumor is a negative prognostic indicator signifying aggressive disease and increased potential for metastasis. Recent efforts to understand the molecular basis of tumor-associated angiogenesis have identified several potential therapeutic targets, including the receptor tyrosine kinases for the angiogenic factor vascular endothelial growth factor (VEGF) (see Zeng et al., J. Biol. Chem. 2001;276:32714-32719). The diaryl urea derivatives according to the present invention, especially the compounds of Formula I, II, III, IV, V, VI, VII, VIII or IX (or exemplary formula thereof), most especially the compounds of Formula I or IV, for use as KDR inhibitors are thus especially appropriate for the therapy of diseases related to VEGF receptor tyrosine kinase overexpression. Among these diseases, especially retinopathies, age-related macula degeneration, psoriasis, haemangioblastoma, haemangioma, arteriosclerosis, inflammatory diseases, such as rheumatoid or rheumatic inflammatory diseases, especially arthritis, such as rheumatoid arthritis, or other chronic inflammatory disorders, such as chronic asthma, arterial or post-transplantational atherosclerosis, endometriosis, and especially neoplastic diseases, for example so-called solid tumors (especially cancers of the gastrointestinal tract, the pancreas, breast, stomach, cervix, bladder, kidney, prostate, ovaries, endometrium, lung, brain, melanoma, Kaposi's sarcoma, squamous cell carcinoma of head and neck, malignant pleural mesothelioma, lymphoma or multiple myeloma) and liquid tumors (e.g. leukemias) are especially important.

In chronic myelogeous leukemia (CML), a reciprocally balanced chromosomal translocation in hematopoietic stem cells (HSCs) produces the BCR-ABL hybrid gene. The latter encodes the oncogenic Bcr-Abl fusion protein. Whereas ABL encodes a tightly regulated protein tyrosine kinase, which plays a fundamental role in regulating cell proliferation, adherence and apoptosis, the BCR-ABL fusion gene encodes as constitutively activated kinase, which transforms HSCs to produce a phenotype exhibiting deregulated clonal proliferation, reduced capacity to adhere to the bone marrow stroma and a reduces apoptotic response to mutagenic stimuli, which enable it to accumulate progressively more malignant transformations. The resulting granulocytes fail to develop into mature lymphocytes and are released into the circulation, leading to a deficiency in the mature cells and increased susceptibility to infection. ATP-competitive inhibitors of Bcr-Abl have been described which prevent the kinase from activating mitogenic and anti-apoptotic pathways (e.g. P-3 kinase and STAT5), leading to the death of the BCR-ABL phenotype cells and thereby providing an effective therapy against CML. The diaryl urea derivatives useful according to the present invention, especially the compounds of the Formula I, II, III, IV, V, VI, VII, VIII or IX (or exemplary formula thereof), most especially the compounds of Formula II, III, IV or V, even more especially compounds of Formula III or V as Bcr-Abl inhibitors, including mutants thereof, are thus especially appropriate for the therapy of diseases related to its overexpression, especially leukemias, such as leukemias, e.g. CML or ALL.

Compounds of the Formula I, II, III, IV, V, VI, VII, VIII or IX (or exemplary formula thereof), in view of their activity as PDGF receptor inhibitors, are also especially appropriate in the treatment of proliferate diseases, especially small lung cancer, atherosclerosis, thrombosis, psoriasis, scleroderma or fibrosis.

There are also experiments to demonstrate the antitumor activity of compounds of the Formula I, II, III, IV, V, VI, VII, VIII or IX (or exemplary formula thereof) in vivo: The in vivo antitumor activity is tested, for example, using breast carcinoma cell lines, such as the human estrogen dependent breast carcinoma MCF-7 (ATCC: HTB22) or ZR-75-1 (ATCC: CRL1500), or the estrogen-independent breast carcinomas MDA-MB468 (ATCC: HTB132) or MDA-MB231 (ATCC: HTB26); colon carcinoma cell lines, such as the colon-carcinoma Colo 205 (ATCC: CCL222); glioblastoma cell lines, such as the glioblastomas U-87MG (ATCC: HTB14) or U-373MG (ATCC: HTB17); lung carcinoma cell lines, such as the "small cell lung carcinomas" NCI-H69 (ATCC: HTB119) or NCI-H209 (ATCC: HTB172), or the lung carcinoma NCI-H596 (ATCC: HTB178); skin tumor cell lines, such as the melanomas Hs294T (ATCC: HTB140) or A375 (ATCC: CRL1619); tumor cell lines from the genitourinry systems, such as the ovarial carcinoma NIH-Ovcar3 (ATCC: HTB161), as well as the prostate carzinomas DU145 (ATCC: HTB81) or PC-3 (ATCC: CRL1435), or the bladder carcinoma T24 (ATCC: HTB4); epithelial carcinomas, such as the epithelial carcinoma KB31; or (especially with regard to leukemias) K562 cells (American Type Culture Collection, Mannassas, Va.) or human CFU-G cells (CFU-G stands for qranulocyte colony forming unit, and it represents an early but committed granulocyte forming precursor cell that circulates in the blood stream or bone marrow) each of which is transplanted into female or male Balb/c nude mice. Other cell lines include leukemic cell lines such as K-562, SUPB15, MEG01, Ku812F, MOLM-13, BaF3, CEM/0, JURKAT/0 or U87MG.

Tumors are obtained after subcutaneous injection of the respective cells (minimum $2 \times 10^6$ cells in 100 mL phosphate buffered physiological saline) into the carrier mice (e.g. 4-8 mice per cell line). The resulting tumors are passed serially through at least three subsequent transplantations before treatment is started. Tumor fragments (about 25 mg each) are injected subcutaneously into the left flank of the animals using a 13-gauge Trocar needle under Forene narcosis (Abbott, Switzerland) for implantation. Mice transplanted with estrogen-dependent tumor are, in addition, supplied with an estrogen pellet (1.0 cm of a tube with a quality appropriate for medical purposes, Dow Chemicals, with 5 mg estradiole, Sigma). The treatment is started routinely (that is at low or intermediate tumor burden), as soon as the tumor has reached an average size of 100 mm$^3$. Tumor growth is determined once, twice or thrice weekly (depending on tumor growth of the cell line) and 24 h after the last treatment by measurement of the perpendicular diameter. In case of tumors, tumor volumes are determined according to the Formula L×D×p/6 (see Evans, B. D., Smith, I. E., Shorthouse, A. J. and Millar, J. J., Brit. J. Cancer, 1982:45:466-468). The antitumor activity is expressed as T/C % (average increase of the tumor volume of treated animals divided by the average increase of tumor volume in control animals multiplied by 100). Tumor regression (%) represents the smallest mean tumor volume compared to the mean tumor volume at the beginning of the treatment. Each animal in which the tumor reaches a diameter of more than 1.5 to 2 cm$^3$ is sacrificed. Leukemia burden is assessed by examining both peripheral white blood count and weight of spleen and thymus in animals tumored with leukemia cell lines.

An exemplary (though not limiting) schedule for administration of a diaryl urea derivative, especially of Formula I, II, III, IV, V, VI, VII, VIII or IX (or exemplary formula thereof), or a salt thereof, is daily administration, with preferably 1 to 3 daily dosages for a longer time, possibly until the disease is cured or, if only palliateive treatment is achieved, for as long as required; alternatively, treatment e.g. for 5 days, and/or administration at days 1, 4 and 9, with eventual repetition after a certain time without treatment is possible. Alternatively, treatment several times a day (e.g. 2 to 5 times) or treatment by continuous administration (e.g. infusion), e.g. at the time points indicated in the last sentence, are possible. Generally, administration is orally or parenterally, preferably orally. The test compounds are preferably diluted in water or in sterile 0.9% saline.

All human tumor cell lines are obtained from the American Type Culture Collection (ATCC, Rockville, Md., USA) if not indicated otherwise and are cultivated in the suggested media with the corresponding additives (ATCC culture conditions), if not mentioned otherwise. The c-sis- and v-sis-transformed BALB/c 3T3 cells are obtained from C. Stiles (Dana Farber Cancer Institute, Boston, Mass., USA). They are cultured in "Dulbecco's modified Eagle's medium" (DMEM), that is supplemented with 10% calf serum and Hygromycin B in a concentration of 0.2 mg/mL or G418 in a concentration of 0.5 mg/ml. BALB/c AMuLV A.6R.1 cells (ATCC) are kept in DMEM, supplemented with 10% FCS.

The pharmacological activity of a diaryl urea derivative of the Formula I, II, III, IV, V, VI, VII, VIII or IX (or exemplary formula thereof) may, for example, be demonstrated in a clinical study or in a test procedure as essentially described hereinafter.

Suitable clinical studies are, for example, open label non-randomized, dose escalation studies in patients with one of the tumor diseases mentioned above. The beneficial effects on proliferative diseases can be determined directly through the results of these studies or by changes in the study design which are known as such to a person skilled in the art. The efficacy of the treatment can be determined in such studies, e.g., in case of tumors after 18 or 24 weeks by radiologic evaluation of the tumors every 6 weeks, in case of a leukemia e.g. by determination of the count of aberrant white blood cells, and by staining mononuclear cells and/or by means of determining minimum residual disease (MRD) e.g. by FACS-LPC MRD or PCR.

Alternatively, a placebo-controlled, double blind study can be used in order to prove the benefits of the diaryl urea derivatives useful according to the invention, especially the compounds of the Formula I, II, III, IV, V, VI, VII, VIII or IX (or exemplary formula thereof), mentioned herein.

A compound of Formula I, II, III, IV, V, VI, VII, VIII or IX (or exemplary formula thereof) can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of Formula I, II, III, IV, V, VI, VII, VIII or IX (or exemplary formula thereof) can besides or in addition be administered especially for tumor therapy, such as leukaemia therapy, in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Therapeutic agents for possible combination are especially one or more cytostatic or cytotoxic compounds, for example a chemotherapeutic agent or several selected from the group comprising indarubicin, cytarabine, interferon, hydroxyurea, bisulfan, or an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, and an inhibitor of the interaction of an SH2 domain with a phosphorylated protein. A specific example of a combination agent is (N-{5-[4-(4-methyl-piperazino-methyl)-benzoylamido]-2-methylphenyl}-4-(3-pyridyl)-2-pyrimidine-amine (Glivec®)/Gleevec®).

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

In general, the invention relates also to the use of a compound of Formula I, II, III, IV, V, VI, VII, VIII or IX (or exemplary formula thereof) or a N-oxide thereof for the inhibition of tyrosine kinase activity, either in vitro or in vivo.

With the groups of preferred compounds of Formula I, II, III, IV, V, VI, VII, VIII or IX (or exemplary formula thereof) and N-oxides thereof, definitions of substituents from the general definitions mentioned hereinbefore may reasonably be used, for example, to replace more general definitions with more specific definitions or especially with definitions characterized as being preferred.

Especially, the invention relates to the use of a compound of Formula I, II, III, IV, V, VI, VII, VIII or IX (or exemplary formula thereof) or of a N-oxide or a possible tautomer thereof or of a pharmaceutically acceptable salt of such a compound for the preparation of a pharmaceutical composition for the treatment of a disease which responds to an inhibition of protein kinase activity, wherein the disease is a neoplastic disease.

More particularly, the invention relates to the use of a compound of the Formula I, II, III, IV, V, VI, VII, VIII or IX (or exemplary formula thereof) or of a N-oxide or a possible tautomer thereof; or of a pharmaceutically acceptable salt of such a compound for the preparation of a pharmaceutical composition for the treatment of leukaemia which responds to an inhibition of the Abl, Abl-Bcr, including mutant forms thereof, and VEGF-R2 tyrosine kinase activity.

The compounds of the invention that are in particular referred to are:

6-(6-Amino-pyrimidin-4-yloxy)-3,4-dihydro-2H-quinoline-1-carboxylic acid (3-trifluoromethyl-phenyl)-amide
6-(6-Amino-pyrimidin-4-yloxy)-3,4-dihydro-2H-quinoline-1-carboxylic acid [3-(4-isopropylpiperazin-1-ylmethyl)-5-trifluoromethyl-phenyl]-amide
6-(6-Methylamino-pyrimidin-4-yloxy)-3,4-dihydro-2H-quinoline-1-carboxylic acid (4-tert.butyl-phenyl)-amide
6-(6-Methylamino-pyrimidin-4-yloxy)-3,4-dihydro-2H-quinoline-1-carboxylic acid [3-(4-isopropylpiperazin-1-ylmethyl)-5-trifluoromethyl-phenyl]-amide
7-(2-Amino-pyrimidin-4-yloxy)-2,3,4,5-tetrahydro-benzo[b]azepine-1-carboxylic acid (3-trifluoromethyl-phenyl)-amide
7-(6-Chloro-pyrimidin-4-yloxy)-2,3,4,5-tetrahydro-benzo[b]azepine-1-carboxylic acid (3-trifluoromethyl-phenyl)-amide
7-(6-Methylamino-pyrimidin-4-yloxy)-2,3,4,5-tetrahydro-benzo[b]azepine-1-carboxylic acid (3-trifluoromethyl-phenyl)-amide
7-(6-Azido-pyrimidin-4-yloxy)-2,3,4,5-tetrahydro-benzo[b]azepine-1-carboxylic acid (3-trifluoromethyl-phenyl)-amide
7-(6-Amino-pyrimidin-4-yloxy)-2,3,4,5-tetrahydro-benzo[b]azepine-1-carboxylic acid (3-trifluoromethyl-phenyl)-amide
7-(2-Amino-6-chloro-pyrimidin-4-yloxy)-2,3,4,5-tetrahydro-benzo[b]azepine-1-carboxylic acid [3-trifluoromethyl-4-(4-methylpiperazin-1-ylmethyl)-phenyl]-amide
7-(2-Amino-pyrimidin-4-yloxy)-2,3,4,5-tetrahydro-benzo[b]azepine-1-carboxylic acid [3-trifluoromethyl-4-(4-methylpiperazin-1-ylmethyl)-phenyl]-amide
5-(6-Chloro-pyrimidin-4-yloxy)-2,3-dihydro-indole-1-carboxylic acid [4-(4-ethyl-piperazin-1-ylmethyl)-phenyl]-amide
5-(6-Azido-pyrimidin-4-yloxy)-2,3-dihydro-indole-1-carboxylic acid [4-(4-ethyl-piperazin-1-ylmethyl)-phenyl]-amide
5-(6-Amino-pyrimidin-4-yloxy)-2,3-dihydro-indole-1-carboxylic acid [4-(4-ethyl-piperazin-1-ylmethyl)-phenyl]-amide
5-(6-Methylamino-pyrimidin-4-yloxy)-2,3-dihydro-indole-1-carboxylic acid [4-(4-ethyl-piperazin-1-ylmethyl)-phenyl]-amide
5-{6-[3-(4-Methylpiperazin-1-yl)-propylamino]-pyrimidin-4-yloxy}-2,3-dihydro-indole-1-carboxylic acid (3-trifluormethyl-phenyl)-amide
5-(6-Isopropylamino-pyrimidin-4-yloxy)-2,3-dihydro-indole-1-carboxylic acid (3-trifluormethyl-phenyl)-amide
5-(6-Amino-pyrimidin-4-yloxy)-2,3-dihydro-indole-1-carboxylic acid (4-tert.butyl-phenyl)-amide
5-(6-Methylamino-pyrimidin-4-yloxy)-2,3-dihydro-indole-1-carboxylic acid (4-tert.butyl-phenyl)-amide
5-(6-Amino-pyrimidin-4-yloxy)-2,3-dihydro-indole-1-carboxylic acid [3-(4-isopropylpiperazin-1-ylmethyl)-5-trifluoromethyl-phenyl]-amide
5-(2-Amino-6-chloro-pyrimidin-4-yloxy)-2,3-dihydro-indole-1-carboxylic acid (3-trifluoromethyl-phenyl)-amide
5-(2-Amino-pyrimidin-4-yloxy)-2,3-dihydro-indole-1-carboxylic acid (3-trifluoromethyl-phenyl)-amide
5-(2-Amino-pyrimidin-4-yloxy)-2,3-dihydro-indole-1-carboxylic acid (2-trifluoromethyl-pyridin-4-yl)-amide
6-(6-Amino-pyrimidin-4-yloxy)-3,4-dihydro-2H-quinoline-1-carboxylic acid (4-pyrrolidin-1-ylmethyl-3-trifluoromethyl-phenyl)-amide
6-(2-Amino-pyrimidin-4-yloxy)-3,4-dihydro-2H-quinoline-1-carboxylic acid (3-trifluoromethyl-phenyl)-amide
6-(2-Amino-pyrimidin-4-yloxy)-3,4-dihydro-2H-quinoline-1-carboxylic acid (3,5-bis-trifluoromethyl-phenyl)-amide
6-(2-Amino-pyrimidin-4-yloxy)-3,4-dihydro-2H-quinoline-1-carboxylic acid (4-chloro-3-trifluoromethyl-phenyl)-amide
6-(2-Amino-pyrimidin-4-yloxy)-3,4-dihydro-2H-quinoline-1-carboxylic acid (4-fluoro-3-trifluoromethyl-phenyl)-amide 6-(2-Amino-pyrimidin-4-yloxy)-3,4-dihydro-2H-quinoline-1-carboxylic acid [4-(4-methyl-piperazin-1-ylmethyl)-3-trifluoromethyl-phenyl]-amide
6-(2-Amino-pyrimidin-4-yloxy)-3,4-dihydro-2H-quinoline-1-carboxylic acid (4-morpholin-4-ylmethyl-3-trifluoromethyl-phenyl)-amide
[6-[[1-[[4-(4-Morpholinyl)-3-(trifluoromethyl)phenylamino]carbonyl]-1H-indol-5-yl]oxy]-4-pyrimidinyl]acetamide
2-Methyl-[6-[[1-[[4-(4-morpholinyl)-3-(trifluoromethyl)phenylamino]carbonyl]-1H-indol-5-yl]oxy]-4-pyrimidinyl]propanamide
3-Hydroxy-[6-[[1-[[4-(4-morpholinyl)-3-(trifluoromethyl)phenylamino]carbonyl]-1H-indol-5-yl]oxy]-4-pyrimidinyl]propanamide
4-Methyl-4-nitro-[6-[[1-[[4-(4-morpholinyl)-3-(trifluoromethyl)phenylamino]carbonyl]-1H-indol-5-yl]oxy]-4-pyrimidinyl]pentanamide
4-Amino-4-methyl-[6-[[1-[[4-(4-morpholinyl)-3-(trifluoromethyl)phenylamino]carbonyl]-1H-indol-5-yl]oxy]-4-pyrimidinyl]propanamide
[6-[[1-[[4-(4-Morpholinyl)-3-(trifluoromethyl)phenylamino]carbonyl]-1H-indol-5-yl]oxy]-4-pyrimidinyl]-3-pyridinecarboxamide
[6-[1-[[4-(4-Morpholinyl)-3-(trifluoromethyl)phenylamino]carbonyl]-1H-indol-5-yl]oxy]-4-pyrimidinyl]carbamic acid, methyl ester
4-Methyl-N-[[6-[1-[[4-(4-morpholinyl)-3-(trifluoromethyl)phenylamino]carbonyl]-1H-indol-5-yl]oxy]-4-pyrimidinyl]-1-piperazinecarboxamide
[6-[[1-[[4-[(4-Methyl-1-piperazinyl)methyl]-3-(trifluoromethyl)phenylamino]carbonyl]-1H-indol-5-yl]oxy]-4-pyrimidinyl]acetamide
[6-[[1-[[4-[(4-Methyl-1-piperazinyl)methyl]-3-(trifluoromethyl)phenylamino]carbonyl]-1H-indol-5-yl]oxy]-4-pyrimidinyl]-3-pyridinecarboxamide
[6-[[1-[[4-[(4-Methyl-1-piperazinyl)methyl]-3-(trifluoromethyl)phenylamino]carbonyl]-1H-indol-5-yl]oxy]-4-pyrimidinyl]carbamic acid methyl ester
[6-[[1-[[4-Cyano-3-(trifluoromethyl)phenylamino]carbonyl]-1H-indol-5-yl]oxy]-4-pyrimidinyl]acetamide
[6-[[1-[[4-(4-Methyl-1-piperazinyl)-3-(trifluoromethyl)phenylamino]carbonyl]-1H-indol-5-yl]oxy]-4-pyrimidinyl]acetamide
[6-[[1-[[4-(4-Cyclopropyl-1-piperazinyl)-3-(trifluoromethyl)phenylamino]carbonyl]-1H-indol-5-yl]oxy]-4-pyrimidinyl]acetamide
[6-[[1-[[4-(3-Pyridinyl)-3-(trifluoromethyl)phenylamino]carbonyl]-1H-indol-5-yl]oxy]-4-pyrimidinyl]acetamide
[6-[[1-[[4-(4-Methyl-1H-imidazol-1-yl)-3-(trifluoromethyl)phenylamino]carbonyl]-1H-indol-5-yl]oxy]-4-pyrimidinyl]acetamide
[6-[[1-[[5-(4-Methyl-1H-imidazol-1-yl)-3-(trifluoromethyl)phenylamino]carbonyl]-1H-indol-5-yl]oxy]-4-pyrimidinyl]acetamide
[6-[[1-[[5-(4-Morpholinyl)-3-(trifluoromethyl)phenylamino]carbonyl]-1H-indol-5-yl]oxy]-4-pyrimidinyl]acetamide
[6-[[1-[[4-(4-Morpholinylmethyl)-3-(trifluoromethyl)phenylamino]carbonyl]-1H-indol-5-yl]oxy]-4-pyrimidinyl]acetamide
[6-[[1-[[4-(2-Methyl-1H-imidazol-1-yl)methyl])-3-(trifluoromethyl)phenylamino]carbonyl]-1H-indol-5-yl]oxy]-4-pyrimidinyl]acetamide
[6-[[1-[[4-[(Diethylamino)methyl])-3-(trifluoromethyl)phenylamino]carbonyl]-[1H-indol-5-yl]oxy]-4-pyrimidinyl]acetamide
[6-[[1-[[4-(Diethylamino)-3-(trifluoromethyl)phenylamino]carbonyl]-1H-indol-5-yl]oxy]-4-pyrimidinyl]acetamide
(±)-[6-[[1-[[4-[(2-Hydroxypropyl)amino]-3-(trifluoromethyl)phenylamino]carbonyl]-1H-indol-5-yl]oxy]-4-pyrimidinyl]acetamide
(±)-[6-[[1-[[4-[3-(Dimethylamino)-1-pyrrolidinyl]-3-(trifluoromethyl)phenylamino]carbonyl]-1H-indol-5-yl]oxy]-4-pyrimidinyl]acetamide
[6-[[1-[[4-[(1-Methyl-4-piperidinyl)oxy]-3-(trifluoromethyl)phenylamino]carbonyl]-1H-indol-5-yl]oxy]-4-pyrimidinyl]acetamide
[4-[[[2,3-Dihydro-5-(6-acetylamino-4-pyrimidinyloxy)-1H-indol-1-yl]carbonyl]amino]-2-(trifluoromethyl)phenoxy]-2-methylpropanoic acid, 1,1-dimethylethyl ester
[4-[[[2,3-Dihydro-5-(6-acetylamino-4-pyrimidinyloxy)-1H-indol-1-yl]carbonyl]amino]-2-(trifluoromethyl)phenoxy]-2-methylpropanoic acid, 2-propenyl ester
[6-[[1-[[4-[3-(trifluoromethyl)phenylamino]carbonyl]-1H-indol-5-yl]oxy]-4-pyrimidinyl]acetamide
[4-[[[2,3-Dihydro-5-(6-acetylamino-4-pyrimidinyloxy)-1H-indol-1-yl]carbonyl]amino]-2-(trifluoromethyl)phenyl]-1-piperazinecarboxylic acid, 1,1-dimethylethyl ester
[6-[[1-[[4-Piperazinyl-3-(trifluoromethyl)phenylamino]carbonyl]-1H-indol-5-yl]oxy]-4-pyrimidinyl]acetamide
[6-[[1-[[4-[(4-Cyclopropyl-1-piperazinyl)methyl]-3-(trifluoromethyl)phenylamino]carbonyl]-1H-indol-5-yl]oxy]-4-pyrimidinyl]acetamide.
[4-[[[2,3-Dihydro-5-(6-acetylamino-4-pyrimidinyloxy)-1H-indol-1-yl]carbonyl]amino]-2-(trifluoromethyl)phenylmethyl]-1-piperazinecarboxylic acid, 1,1-dimethylethyl ester
[6-[[1-[[4-(1,1-Dioxido-4-thiomorpholinyl)-3-(trifluoromethyl)phenylamino]carbonyl]-1H-indol-5-yl]oxy]-4-pyrimidinyl]acetamide
[6-[[1-[[4-(1-Pyrrolidinylmethyl)-3-(trifluoromethyl)phenylamino]carbonyl]-1H-indol-5-yl]oxy]-4-pyrimidinyl]acetamide
[6-[[1-[[4-[(1-Piperazinyl)methyl]-3-(trifluoromethyl)phenylamino]carbonyl]-1H-indol-5-yl]oxy]-4-pyrimidinyl]acetamide
[2-[[1-[[4-[(4-Methyl-1-piperazinyl)methyl]-3-(trifluoromethyl)phenylamino]carbonyl]-1H-indol-5-yl]oxy]-4-pyrimidinyl]acetamide
[4-[[[2,3-Dihydro-5-(6-acetylamino-4-pyrimidinyloxy)-1H-indol-1-yl]carbonyl]amino]-2-(trifluoromethyl)phenoxy]-2-methylpropanoic acid
6-[1-[[3-(Trifluoromethyl)phenylamino]carbonyl]-1H-indol-5-yl]oxy]-4-pyrimidinyl]carbamic acid, methyl ester
5-[(4-amino-6-pyrimidinyl)oxy]-N-[3-(trifluoromethyl)phenyl]-1H-indole-1-carboxamide is prepared as follows:
5-[(4-azido-6-pyrimidinyl)oxy]-N-[3-(trifluoromethyl)phenyl]-1H-indole-1-carboxamide
or salts, esters, N-oxides or prodrugs thereof.

In particular, the compounds of the invention may be selected from:
[6-[[1-[[4-(4-Morpholinyl)-3-(trifluoromethyl)phenylamino]carbonyl]-1H-indol-5-yl]oxy]-4-pyrimidinyl]acetamide
2-Methyl-[6-[[1-[[4-(4-morpholinyl)-3-(trifluoromethyl)phenylamino]carbonyl]-1H-indol-5-yl]oxy]-4-pyrimidinyl]propanamide
3-Hydroxy-[6-[[1-[[4-(4-morpholinyl)-3-(trifluoromethyl)phenylamino]carbonyl]-1H-indol-5-yl]oxy]-4-pyrimidinyl]propanamide
4-Methyl-4-nitro-[6-[[1-[[4-(4-morpholinyl)-3-(trifluoromethyl)phenylamino]carbonyl]-1H-indol-5-yl]oxy]-4-pyrimidinyl]pentanamide 4-Amino-4-methyl-[6-[[1-[[4-(4-morpholinyl)-3-(trifluoromethyl)phenylamino]carbonyl]-1H-indol-5-yl]oxy]-4-pyrimidinyl]propanamide

[6-[[1-[[4-(4-Morpholinyl)-3-(trifluoromethyl)phenylamino]carbonyl]-1H-indol-5-yl]oxy]-4-pyrimidinyl]-3-pyridinecarboxamide

[6-[1-[[4-(4-Morpholinyl)-3-(trifluoromethyl)phenylamino]carbonyl]-1H-indol-5-yl]oxy]-4-pyrimidinyl]carbamic acid, methyl ester 4-Methyl-N-[[6-[1-[[4-(4-morpholinyl)-3-(trifluoromethyl)phenylamino]carbonyl]-1H-indol-5-yl]oxy]-4-pyrimidinyl]-1-piperazinecarboxamide

[6-[[1-[[4-[(4-Methyl-1-piperazinyl)methyl]-3-(trifluoromethyl)phenylamino]carbonyl]-1H-indol-5-yl]oxy]-4-pyrimidinyl]acetamide

[6-[[1-[[4-[(4-Methyl-1-piperazinyl)methyl]-3-(trifluoromethyl)phenylamino]carbonyl]-1H-indol-5-yl]oxy]-4-pyrimidinyl]-3-pyridinecarboxamide

[6-[[1-[[4-[(4-Methyl-1-piperazinyl)methyl]-3-(trifluoromethyl)phenylamino]carbonyl]-1H-indol-5-yl]oxy]-4-pyrimidinyl]carbamic acid methyl ester

[6-[[1-[[4-Cyano-3-(trifluoromethyl)phenylamino]carbonyl]-1H-indol-5-yl]oxy]-4-pyrimidinyl]acetamide

[6-[[1-[[4-(4-Methyl-1-piperazinyl)-3-(trifluoromethyl)phenylamino]carbonyl]-1H-indol-5-yl]oxy]-4-pyrimidinyl]acetamide

[6-[[1-[[4-(4-Cyclopropyl-1-piperazinyl)-3-(trifluoromethyl)phenylamino]carbonyl]-1H-indol-5-yl]oxy]-4-pyrimidinyl]acetamide

[6-[[1-[[4-(3-Pyridinyl)-3-(trifluoromethyl)phenylamino]carbonyl]-1H-indol-5-yl]oxy]-4-pyrimidinyl]acetamide

[6-[[1-[[4-(4-Methyl-1H-imidazol-1-yl)-3-(trifluoromethyl)phenylamino]carbonyl]-1H-indol-5-yl]oxy]-4-pyrimidinyl]acetamide

[6-[[1-[[5-(4-Methyl-1H-imidazol-1-yl)-3-(trifluoromethyl)phenylamino]carbonyl]-1H-indol-5-yl]oxy]-4-pyrimidinyl]acetamide

[6-[[1-[[5-(4-Morpholinyl)-3-(trifluoromethyl)phenylamino]carbonyl]-1H-indol-5-yl]oxy]-4-pyrimidinyl]acetamide

[6-[[1-[[4-(4-Morpholinylmethyl)-3-(trifluoromethyl)phenylamino]carbonyl]-1H-indol-5-yl]oxy]-4-pyrimidinyl]acetamide

[6-[[1-[[4-(2-Methyl-1H-imidazol-1-yl)methyl])-3-(trifluoromethyl)phenylamino]carbonyl]-1H-indol-5-yl]oxy]-4-pyrimidinyl]acetamide

[6-[[1-[[4-[(Diethylamino)methyl])-3-(trifluoromethyl)phenylamino]carbonyl]-1H-indol-5-yl]oxy]-4-pyrimidinyl]acetamide

[6-[[1-[[4-(Diethylamino)-3-(trifluoromethyl)phenylamino]carbonyl]-1H-indol-5-yl]oxy]-4-pyrimidinyl]acetamide (±)-[6-[[1-[[4-[(2-Hydroxypropyl)amino]-3-(trifluoromethyl)phenylamino]carbonyl]-1H-indol-5-yl]oxy]-4-pyrimidinyl]acetamide (±)-[6-[[1-[[4-[3-(Dimethylamino)-1-pyrrolidinyl]-3-(trifluoromethyl)phenylamino]carbonyl]-1H-indol-5-yl]oxy]-4-pyrimidinyl]acetamide

[6-[[1-[[4-[(1-Methyl-4-piperidinyl)oxy]-3-(trifluoromethyl)phenylamino]carbonyl]-1H-indol-5-yl]oxy]-4-pyrimidinyl]acetamide

[4-[[[2,3-Dihydro-5-(6-acetylamino-4-pyrimidinyloxy)-1H-indol-1-yl]carbonyl]amino]-2-(trifluoromethyl)phenoxy]-2-methylpropanoic acid, 1,1-dimethylethyl ester

[6-[[1-[[4-[3-(trifluoromethyl)phenylamino]carbonyl]-1H-indol-5-yl]oxy]-4-pyrimidinyl]acetamide

[4-[[[2,3-Dihydro-5-(6-acetylamino-4-pyrimidinyloxy)-1H-indol-1-yl]carbonyl]amino]-2-(trifluoromethyl)phenyl]-1-piperazinecarboxylic acid, 1,1-dimethylethyl ester

[6-[[1-[[4-Piperazinyl-3-(trifluoromethyl)phenylamino]carbonyl]-1H-indol-5-yl]oxy]-4-pyrimidinyl]acetamide

[6-[[1-[[4-[(4-Cyclopropyl-1-piperazinyl)methyl]-3-(trifluoromethyl)phenylamino]carbonyl]-1H-indol-5-yl]oxy]-4-pyrimidinyl]acetamide.

[4-[[[2,3-Dihydro-5-(6-acetylamino-4-pyrimidinyloxy)-1H-indol-1-yl]carbonyl]amino]-2-(trifluoromethyl)phenylmethyl]-1-piperazinecarboxylic acid, 1,1-dimethylethyl ester

[6-[[1-[[4-(1,1-Dioxido-4-thiomorpholinyl)-3-(trifluoromethyl)phenylamino]carbonyl]-1H-indol-5-yl]oxy]-4-pyrimidinyl]acetamide

[6-[[1-[[4-(1-Pyrrolidinylmethyl)-3-(trifluoromethyl)phenylamino]carbonyl]-1H-indol-5-yl]oxy]-4-pyrimidinyl]acetamide

[6-[[1-[[4-[(1-Piperazinyl)methyl]-3-(trifluoromethyl)phenylamino]carbonyl]-1H-indol-5-yl]oxy]-4-pyrimidinyl]acetamide

[2-[[1-[[4-[(4-Methyl-1-piperazinyl)methyl]-3-(trifluoromethyl)phenylamino]carbonyl]-1H-indol-5-yl]oxy]-4-pyrimidinyl]acetamide

[4-[[[2,3-Dihydro-5-(6-acetylamino-4-pyrimidinyloxy)-1H-indol-1-yl]carbonyl]amino]-2-(trifluoromethyl)phenoxy]-2-methylpropanoic acid 6-[1-[[3-(Trifluoromethyl)phenylamino]carbonyl]-1H-indol-5-yl]oxy]-4-pyrimidinyl]carbamic acid, methyl ester or salts, esters, N-oxides or prodrugs thereof.

The compounds of the invention may be further selected from:

[6-[[1-[[4-(4-Morpholinyl)-3-(trifluoromethyl)phenylamino]carbonyl]-1H-indol-5-yl]oxy]-4-pyrimidinyl]acetamide 3-Hydroxy-[6-[[1-[[4-(4-morpholinyl)-3-(trifluoromethyl)phenylamino]carbonyl]-1H-indol-5-yl]oxy]-4-pyrimidinyl]propanamide

[6-[[1-[[4-(4-Morpholinyl)-3-(trifluoromethyl)phenylamino]carbonyl]-1H-indol-5-yl]oxy]-4-pyrimidinyl]-3-pyridinecarboxamide

[6-[1-[[4-(4-Morpholinyl)-3-(trifluoromethyl)phenylamino]carbonyl]-1H-indol-5-yl]oxy]-4-pyrimidinyl]carbamic acid, methyl ester

[6-[[1-[[4-[(4-Methyl-1-piperazinyl)methyl]-3-(trifluoromethyl)phenylamino]carbonyl]-1H-indol-5-yl]oxy]-4-pyrimidinyl]acetamide

[6-[[1-[[4-[(4-Methyl-1-piperazinyl)methyl]-3-(trifluoromethyl)phenylamino]carbonyl]-1H-indol-5-yl]oxy]-4-pyrimidinyl]-3-pyridinecarboxamide

[6-[[1-[[4-[(4-Methyl-1-piperazinyl)methyl]-3-(trifluoromethyl)phenylamino]carbonyl]-1H-indol-5-yl]oxy]-4-pyrimidinyl]carbamic acid methyl ester

[6-[[1-[[4-(3-Pyridinyl)-3-(trifluoromethyl)phenylamino]carbonyl]-1H-indol-5-yl]oxy]-4-pyrimidinyl]acetamide

[6-[[1-[[5-(4-Morpholinyl)-3-(trifluoromethyl)phenylamino]carbonyl]-1H-indol-5-yl]oxy]-4-pyrimidinyl]acetamide

[6-[[1-[[4-(4-Morpholinylmethyl)-3-(trifluoromethyl)phenylamino]carbonyl]-1H-indol-5-yl]oxy]-4-pyrimidinyl]acetamide

[6-[[1-[[4-[(Diethylamino)methyl])-3-(trifluoromethyl)phenylamino]carbonyl]-1H-indol-5-yl]oxy]-4-pyrimidinyl]acetamide

[6-[[1-[[4-(Diethylamino)-3-(trifluoromethyl)phenylamino]carbonyl]-1H-indol-5-yl]oxy]-4-pyrimidinyl]acetamide

[6-[[1-[[4-[(1-Methyl-4-piperidinyl)oxy]-3-(trifluoromethyl)phenylamino]carbonyl]-1H-indol-5-yl]oxy]-4-pyrimidinyl]acetamide

[6-[[1-[[4-[(4-Cyclopropyl-1-piperazinyl)methyl]-3-(trifluoromethyl)phenylamino]carbonyl]-1H-indol-5-yl]oxy]-4-pyrimidinyl]acetamide.

[6-[[1-[[4-(1-Pyrrolidinylmethyl)-3-(trifluoromethyl)phenylamino]carbonyl]-1H-indol-5-yl]oxy]-4-pyrimidinyl]acetamide.

or salts, esters, N-oxides or prodrugs thereof.

In addition, the invention provides a method for the treatment of a disease which responds to an inhibition of protein kinase activity, which comprises administering a compound of Formula I, II, III, IV, V, VI, VII, VIII or IX (or exemplary formula thereof) or a N-oxide or a pharmaceutically acceptable salt thereof, wherein the radicals and symbols have the meanings as defined above, in a quantity effective against said disease, to a warm-blooded animal requiring such treatment.

A compound of the invention may be prepared by processes that, though not applied hitherto for the new compounds of the present invention, are known per se, where the compounds and intermediates may also be present with functional groups in protected form if necessary and/or in the form of salts, provided a salt-forming group is present and the reaction in salt form is possible;

any protecting groups in a protected derivative of a compound of the Formula I, II, III, IV, V, VI, VII, VIII or IX (or exemplary formula thereof) are removed;

and, if so desired, an obtainable compound of Formula I, II, III, IV, V, VI, VII, VIII or IX (or exemplary formula thereof) is converted into another compound of Formula I, II, III, IV, V, VI, VII, VIII or IX (or exemplary formula thereof) or a N-oxide thereof, a free compound of Formula I, II, III, IV, V, VI, VII, VIII or IX (or exemplary formula thereof) is converted into a salt, an obtainable salt of a compound of Formula I, II, III, IV, V, VI, VII, VIII or IX (or exemplary formula thereof) is converted into the free compound or another salt, and/or a mixture of isomeric compounds of Formula I, II, III, IV, V, VI, VII, VIII or IX (or exemplary formula thereof) is separated into the individual isomers.

Protecting Groups

If one or more other functional groups, for example carboxy, hydroxy, amino, or mercapto, are or need to be protected in a compound of Formula I, II, III, IV, V, VI, VII, VIII or IX (or exemplary formula thereof)II, because they should not take part in the reaction, these are such groups as are usually used in the synthesis of amides, in particular peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis as cited hereinbefore, and in special books on protective groups such as J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/I, Georg Thieme Verlag, Stuttgart 1974, and in T. W. Greene, "Protective Groups in Organic Synthesis", Wiley, N.Y.

Pharmaceutical Preparations, Methods, and Uses

The present invention relates also to pharmaceutical compositions that comprise a compound of Formula I, II, III, IV, V, VI, VII, VIII or IX (or exemplary formula thereof) or a N-oxide thereof as active ingredient and that can be used especially in the treatment of the aforementioned diseases.

The pharmacologically acceptable compounds of the present invention may be used, for example, for the preparation of pharmaceutical compositions that comprise a pharmaceutically effective amount of a compound of the Formula I, II, III, IV, V, VI, VII, VIII or IX (or exemplary formula thereof), or a pharmaceutically acceptable salt thereof, as active ingredient together or in admixture with a significant amount of one or more inorganic or organic, solid or liquid, pharmaceutically acceptable carriers.

The invention relates also to a pharmaceutical composition that is suitable for administration to a warm-blooded animal, especially a human (or to cells or cell lines derived from a warm-blooded animal, especially a human, e.g. lymphocytes), for the treatment or, in a broader aspect of the invention, prevention of (=prophylaxis against) a disease that responds to inhibition of tyrosin protein kinase activity, especially one of the diseases mentioned above as being preferred for use of a compound of Formula I, II, III, IV, V, VI, VII, VIII or IX (or exemplary formula thereof), comprising an amount of a novel compound of Formula I, II, III, IV, V, VI, VII, VIII or IX (or exemplary formula thereof), or a pharmaceutically acceptable salt thereof, which is effective for said inhibition, together with at least one pharmaceutically acceptable carrier.

Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The present invention relates especially to pharmaceutical compositions that comprise a compound of Formula I, II, III, IV, V, VI, VII, VIII or IX (or exemplary formula thereof), a tautomer, a N-oxide or a pharmaceutically acceptable salt, or a hydrate or solvate thereof, and at least one pharmaceutically acceptable carrier.

The invention relates also to pharmaceutical compositions for use in a method for the prophylactic or especially therapeutic management of the human or animal body, to a process for the preparation thereof (especially in the form of compositions for the treatment of tumors) and to a method of treating tumor diseases, especially those mentioned hereinabove.

The invention relates also to processes and to the use of compounds of Formula I, II, III, IV, V, VI, VII, VIII or IX (or exemplary formula thereof) or N-oxides thereof for the preparation of pharmaceutical preparations which comprise compounds of Formula I, II, III, IV, V, VI, VII, VIII or IX (or exemplary formula thereof) or N-oxides thereof as active component (active ingredient).

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, sprays, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents or solubilizers, such as sodium carboxymethyl cellulose, carboxymethyl-cellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydroxy, for example a mono-, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

Injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragé cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it being possible also for stabilisers and/or antibacterial agents to be added. Dyes or pigments may be added to the tablets or dragée coatings or the capsule casings, for example for identification purposes or to indicate different doses of active ingredient.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations.

Pharmaceutical compositions for oral administration also include hard capsules consisting of gelatin, and also soft, sealed capsules consisting of gelatin and a plasticizer. The hard capsules may contain the active ingredient in the form of granules, for example in admixture with fillers, binders, and/or glidants, and optionally stabilizers. In soft capsules, the active ingredient is preferably dissolved or suspended in suitable liquid excipients, to which stabilizers and detergents may also be added.

Pharmaceutical compositions suitable for rectal administration are, for example, suppositories that consist of a combination of the active ingredient and a suppository base.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antioxidants, such as ascorbic acid, or microbicides, such as sorbic acid or benzoic acid.

The invention relates likewise to a process or a method for the treatment of one of the pathological conditions mentioned hereinabove, especially a disease which responds to an inhibition of a tyrosine kinase, especially a corresponding neoplastic disease. The compounds of Formula I, II, III, IV, V, VI, VII, VIII or IX (or exemplary formula thereof) or N-oxides thereof can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

The invention also provides for a method of treating a protein kinase dependent disease, comprising administering to a warm-blooded animal, for example a human, one or more cytostatic or cytotoxic compounds e.g. Glivec® in combination with a compound of the invention, whether at the same time, or a separate time. The term "the same time" is taken to mean in quick succession or immediately after one another.

The present invention relates especially also to the use of a compound of Formula I, II, III, IV, V, VI, VII, VIII or IX (or exemplary formula thereof) or N-oxides thereof, or a pharmaceutically acceptable salt thereof, especially a compound of Formula I, II, III, IV, V, VI, VII, VIII or IX (or exemplary formula thereof) which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably a disease which responds to an inhibition of a protein kinase, especially a neoplastic disease, more especially leukaemia which responds to an inhibition of the Abl tyrosine kinase.

The preferred dose quantity, composition, and preparation of pharmaceutical formulations (medicines) which are to be used in each case are described above.

A compound of the Formula I, II, III, IV, V, VI, VII, VIII or IX (or exemplary formula thereof) may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, anti-androgens, bengamides, bisphosphonates, antiproliferative antibodies and temozolomide (TEMODAL®).

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Anastrozole can be administered, e.g., in the form as it is marketed, e.g. under the trademark ARIMIDEX™. Letrozole can be administered, e.g., in the form as it is marketed, e.g. under the trademark FEMARA™ or FEMAR™. Aminoglutethimide can be administered, e.g., in the form as it is marketed, e.g. under the trademark ORIMETEN™.

A combination of the invention comprising an antineoplastic agent which is an aromatase inhibitor is particularly useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be Formulated as disclosed in U.S. Pat. No. 4,659,516 or it can be administered, e.g., in the form as it is marketed, e.g. under the trademark FASLODEX™.

The term "topoisomerase I inhibitors" as used herein includes, but is not limited to topotecan, irinotecan, 9-nitrocamptothecin and the macromolecular camptothecin conjugate PNU-166148 (compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal Formulation, e.g. CAELYX™), epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™. Doxorubicin can be administered, e.g., in the form as it is marketed, e.g. under the trademark ADRIBLASTIN™. Epirubicin can be administered, e.g., in the form as it is marketed, e.g. under the trademark FARMORUBICIN™. Idarubicin can be administered, e.g., in the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agents" as used herein includes, but is not limited to cyclophosphamide, ifosfamide and melphalan. Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity.

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enyzme (COX-2) and which possess antiproliferative activity such as celecoxib (Celebrex®), rofecoxib (Vioxx®) and lumiracoxib (COX189).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "antineoplastic antimetabolites" includes, but is not limited to 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cis-platin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF), c-Src, protein kinase C, the Platelet-derived Growth Factor (PDGF), Bcr-Abl, c-Kit, Flt-3, the Insulin-like Growth Factor I Receptor (IGF-IR) and the Cyclin-dependent kinases (CDKs), and anti-angiogenic compounds having another mechanism of action than decreasing the protein kinase activity. Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO 98/35958, WO 00/09495, WO 00/27820, WO 00/59509, WO 98/11223, WO 00/27819, WO 01/55114, WO 01/58899 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, vol. 27, no. 1, pp 14-21, 1999; in WO 00/37502 and WO 94/10202; Angiostatin™, described by M. S. O'Reilly et al, Cell 79, 1994, 315-328; and Endostatin™, described by M. S. O'Reilly et al, Cell 88, 1997, 277-285;

compounds which decrease the activity of EGF are especially
   compounds which inhibit the EGF receptor, especially the tyrosine kinase activity of the EGF receptor, and compounds binding to EGF, and are in particular those compounds generically and specifically disclosed in WO 97/02266, EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980;

compounds which decrease the activity of c-Src include, but
   are not limited to, compounds inhibiting the c-Src protein tyrosine kinase activity as defined below and to SH2 interaction inhibitors such as those disclosed in WO97/07131 and WO97/08193;

compounds inhibiting the c-Src protein tyrosine kinase activity include, but are not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d]pyrimidines. Preferably, the term relates to those compounds disclosed in WO 96/10028, WO 97/28161, WO97/32879 and WO97/49706;

compounds which decreases the activity of the protein kinase C are especially those staurosporine derivatives disclosed in EP 0 296 110 (pharmaceutical preparation described in WO 00/48571) which compounds are protein kinase C inhibitors; further specific compounds that decrease protein kinase activity and which may also be used in combination with the compounds of the present invention are Imatinib (Gleevec®/Glivec®), PKC412, Iressa™ (ZD1839), PKI166, PTK787, ZD6474, GW2016, CHIR-200131, CEP-7055/CEP-5214, CP-547632, KRN-633 and SU5416; anti-angiogenic compounds having another mechanism of action than decreasing the protein kinase activity include, but are not limited to e.g. thalidomide (THALOMID), celecoxib (Celebrex) and ZD6126.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™.

The term "anti-androgens" as used herein includes, but is not limited to bicalutamide (CASODEX™), which can be formulated, e.g. as disclosed in U.S. Pat. No. 4,636,505.

The term "bisphosphonates" as used herein includes, but is not limited to etridonic acid, clodronic acid, tiludronic acid, pamidronic acid, alendronic acid, ibandronic acid, risedronic acid and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOS™. "Tiludronic acid" can be administered, e.g., in the form as it is marketed, e.g. under the trademark SKELID™. "Pamidronic acid" can be administered, e.g., in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g., in the form as it is marketed, e.g. under the trademark ZOMETA™.

The term "antiproliferative antibodies" as used herein includes, but is not limited to trastuzumab (Herceptin™), Trastuzumab-DM1, erlotinib (Tarceva™), bevacizumab (Avastin™), rituximab (Rituxan®), PRO64553 (anti-CD40) and 2C4 Antibody.

For the treatment of acute myeloid leukemia (AML), compounds of Formula I, II, III, IV, V, VI, VII, VIII or IX (or exemplary formula thereof) can be used in combination with standard leukemia therapies, especially in combination with therapies used for the treatment of AML. In particular, compounds of Formula I, II, III, IV, V, VI, VII, VIII or IX (or exemplary formula thereof) can be administered in combination with e.g. farnesyltransferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the Formula I, II, III, IV, V, VI, VII, VIII or IX (or exemplary formula thereof), can be prepared and administered as described in the art such as in the documents cited above.

General Process Conditions

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the H$^+$ form, depending on the type of reaction and/or reactants at reduced, normal, or elevated temperature, for example in the range from −100° C. to about 190° C., preferably from about −80° C. to about 150° C., for example at −80 to −60° C., at room temperature, at −20 to 40° C. or at the boiling point of the solvent used, under atmospheric pressure or in a closed vessel, where appropriate under pressure, and/or in an inert atmosphere, for example under argon or nitrogen.

It should be emphasized that reactions analogous to the conversions mentioned in this chapter may also take place at the level of appropriate intermediates.

Detailed Description of the Process

The diaryl urea derivatives of the present invention may be prepared according to conventional methods known in the art e.g. as described in the Examples.

According to a general exemplary process, compounds having the structure of general Formula I, wherein R$^1$ represents R$^{10}$C(O)NH—, A is oxygene, R$^a$ and R$^b$ are both hydrogen and p is 1, may be prepared from halides of general Formula (ii):

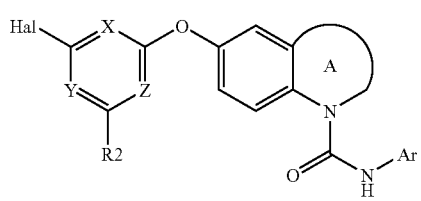

In which Hal represents a halogen atom, preferably, Cl, Br or F, by reaction with amides of general Formula R$^{10}$CONH$_2$ (iii), wherein the radical R$^{10}$ has the meaning as defined for a compound of Formula II, in the presence of a suitable catalyst, as for example according to the method described by J. Yin and S. Buchwald (*J. Amer. Chem. Soc.* 2002:124:6043-6048).

Halides of general Formula (ii) may be prepared from the corresponding azaheterocyclic compounds of general Formula (iv):

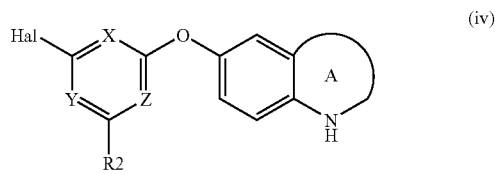

by reaction with a carbamate of general Formula R$_s$OCONHAr (v), in which R$_s$ represents an optionally substituted lower alkyl group, such as benzyl or tert-butyl, or an optionally substituted aryl group, such as phenyl or 4-nitrophenyl, in the presence of a suitable base such as a tertiary amine, for example triethylamine or Hunig's base in an aprotic solvent such as tetrahydrofuran, or an alkali metal alkoxide or alkali metal hydroxide, such as potassium tertiary-butoxide or sodium hydroxide, in either an aprotic solvent, such as DMF, or an alcohol, such as ethanol.

Alternatively, compounds of general Formula (ii) can be prepared by reacting compounds of general Formula IV with suitably substituted isocyanates of general Formula ArN=C=O (vi), in the presence of an organic base, such as pyridine, in an aprotic solvent, such as tetrahydrofuran.

Alternatively, compounds of general Formula (ii) can also be prepared by reacting compounds of general Formula (iv) with bis(trichloromethyl)carbonate (triphosgene) in the presence of an aprotic base, such as triethylamine or Hunig's base, in an aprotic solvent, followed by the addition of a suitable ArNH$_2$. Similarly, the reaction can be carried out by reacting the amine, ArNH$_2$ with bis(trichloromethyl)carbonate, followed by the addition of a compound of general Formula (iv).

Azaheterocyclic compounds of general Formula (iv) may be prepared by reacting a suitably substituted phenolic compound, such as 5-hydroxyindole, with a suitable heterocycle of general Formula (vii):

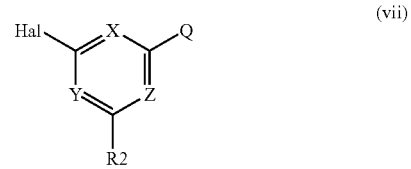

in which Q represents a suitable leaving group, such as a halogen atom or a group S(O)$_n$R$^2$, where R represents an alkyl group and n is an integer 0-2, in the presence of a suitable base or a catalyst.

The starting materials of Formula (vii) are known or may be prepared according to conventional procedures starting from known compounds, for example as described in the Examples. Compounds of Formula I, wherein the radicals and symbols R$^1$, A, R$^a$, R$^b$ and p have a different meaning, can be obtained analogously by using of starting materials and reaction conditions also known in the art.

Additional Process Steps

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

Salts of a compound of Formula I, II, III, IV, V, VI, VII, VIII or IX (or exemplary formula thereof) with a salt-forming group may be prepared in a manner known per se. Acid addition salts of compounds of Formula I, II, III, IV, V, VI, VII, VIII or IX (or exemplary formula thereof) may thus be obtained by treatment with an acid or with a suitable anion exchange reagent.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of Formula I, II, III, IV, V, VI, VII, VIII or IX (or exemplary formula thereof) itself. Enantiomers may be separated through the formation of diastereomeric salts, for example by salt formation with an enantiomer-pure chiral acid, or by means of chromatography, for example by HPLC, using chromatographic substrates with chiral ligands.

A compound of the invention, where hydrogen is present, can be converted to the respective compound wherein $R_1$ is lower alkyl by reaction e.g. with a diazo lower alkyl compound, especially diazomethane, in an inert solvent, preferably in the presence of a noble metal catalyst, especially in dispersed form, e.g. copper, or a noble metal salt, e.g. copper (I)-chloride or copper(II)-sulfate. Also reaction with lower alkylhalogenides is possible, or with other leaving group carrying lower alkanes, e.g. lower alkyl alcohols esterified by a strong organic sulfonic acid, such as a lower alkanesulfonic acid (optionally substituted by halogen, such as fluoro), an aromatic sulfonic acid, for example unsubstituted or substituted benzenesulfonic acid, the substituents preferably being selected from lower alkyl, such as methyl, halogen, such as bromo, and/or nitro, e.g. esterified by methanesulfonic acid, or p-toluene sulfonic acid. The alkylation takes place under usual conditions for alkylation of amides, especially in aqueous solution and/or in the presence of polar solvents, typically alcohols, for example methanol, ethanol, isopropanol, or ethylene glycol, or dipolar aprotic solvents, e.g. tetrahydrofuran, dioxane, or dimethylformamide, where applicable in the presence of acidic or basic catalysts, generally at temperatures from about 0° C. to the boiling temperature of the corresponding reaction mixture, preferably between 20° C. and reflux temperature, if necessary under increased pressure, e.g. in a sealed tube, and/or under inert gas, typically nitrogen or argon.

Salts may be present in all starting compounds and transients, if these contain salt-forming groups. Salts may also be present during the reaction of such corn pounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described hereinabove as preferred, particularly as especially preferred, primarily preferred, and/or preferred above all.

In the preferred embodiment, a compound of Formula I, II, III, IV, V, VI, VII, VIII or IX (or exemplary formula thereof) is prepared according to or in analogy to the processes and process steps defined in the Examples.

The compounds of Formula I, II, III, IV, V, VI, VII, VIII or IX (or exemplary formula thereof), including their salts, are also obtainable in the form of hydrates, or their crystals can include for example the solvent used for crystallization (present as solvates).

EXAMPLES

The following Examples serve to illustrate the invention without limiting the scope thereof.

Temperatures are measured in degrees Celsius. Unless otherwise indicated, the reactions take place at room temperature under $N_2$-atmosphere.

The $R_f$ values which indicate the ratio of the distance moved by each substance to the distance moved by the eluent front are determined on silica gel thin-layer plates (Merck, Darmstadt, Germany) by thin-layer chromatography using the respective named solvent systems.

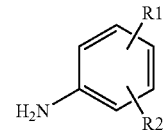

Most respective anilines are described in WO 03/099771 or can be prepared analogously to the therein exemplified derivatives. All others are described elsewhere.

| | Abbreviations: |
|---|---|
| Anal. | elemental analysis (for indicated atoms, difference between calculated and measured value $\leq 0.4\%$) |
| brine | saturated solution of NaCl in water |
| conc. | concentrated |
| d | day(s) |
| DIPE | diisopropyl-ether |
| DMAP | dimethylaminopyridine |
| DMEU | 1,3-dimethyl-2-imidazolidinone |
| DMF | dimethyl formamide |
| DMSO | dimethylsulfoxide |
| ether | diethylether |
| Et$_3$N | triethylamine |
| EtOAc | ethyl acetate |
| EtOH | ethanol |
| Ex. | Example |
| h | hour(s) |
| HPLC | high pressure liquid chromatography |
| l | litre(s) |
| Me | methyl |
| MeOH | methanol |
| min | minute(s) |
| m.p. | melting point |

-continued

| Abbreviations: | |
|---|---|
| MPLC | medium pressure liquid chromatography |
| Combi Flash system: | normal phase SiO$_2$ |
| Gilson system: | reversed phase Nucleosil C18 (H$_2$O/CH$_3$CN + TFA), generally product obtained as free base after neutralization with NaHCO$_3$ |
| MS | mass spectrum |
| NEt$_3$ | triethylamine |
| R$_f$ | ratio of fronts (TLC) |
| rt | room temperature |
| THF | tetrahydrofuran (distilled from Na/benzophenone) |
| TFA | trifluoroacetic acid |
| TLC | thin layer chromatography |
| t$_{Ret}$ | retention time (HPLC) |
| triphosgene | bis(trichloromethyl) carbonate |
| sat. | saturated |

HPLC Conditions:

$^A$t$_{Ret}$: retention time [min] for System A: Linear gradient 20-100% CH$_3$CN (0.1% TFA) and H$_2$O (0.1% TFA) in 13 min+5 min 100% CH$_3$CN (0.1% TFA); detection at 215 nm, flow rate 1 ml/min at 25 or 30° C. Column: Nucleosil 120-3 C18 (125×3.0 mm).

$^B$t$_{Ret}$: retention time [min] for System B: Linear gradient 5-40% CH$_3$CN (0.1% TFA) and H$_2$O (0.1% TFA) in 9 min+7 min 40% CH$_3$CN (0.1% TFA); detection at 215 nm, flow rate 1 ml/min at 25 or 30° C. Column: Nucleosil 120-3 C18 (125×3.0 mm).

$^C$t$_{Ret}$: retention time [min] for System C: Linear gradient 15-100% CH$_3$CN (0.1% TFA) and H$_2$O (0.1% TFA) in 2.25 min+1.25 min 100% CH$_3$CN (0.1% TFA); detection at 215 nm, flow rate 2 ml/min at 25 or 30° C. Column: CC (50×4.6 mm) Uptisphere UP3ODB-5QS.

$^D$t$_{Ret}$: retention time [min] for System D: Linear gradient 20-100% CH$_3$CN (0.1% TFA) and H$_2$O (0.1% TFA) in 14 min+5 min 100% CH$_3$CN (0.1% TFA); detection at 215 nm, flow rate 1 ml/min at 25 or 30° C. Column: CC (250×4.6 mm) Nucleosil 100-5 C18.

Examples of intermediates of the compounds of the present invention are shown below:

Intermediates of Formula (ii):

Intermediate IIa: 2,3-Dihydro-5-(6-chloro-4-pyrimidinyloxy)-N-[4-(4-morpholinyl)-3-(trifluoromethyl)phenyl]-1H-indole-1-carboxamide A solution containing 5-amino-2-(4-morpholinyl)benzotrifluoride (3.16 g, 12.8 mmol) and triethylamine (2.48 mL, 17.8 mmol) in CH$_2$Cl$_2$ (87 mL) is added dropwise to a stirred solution of bis(trichloromethyl)carbonate (1.26 g, 4.25 mmol) in CH$_2$Cl$_2$ (43 mL) at 0° C. After 30 min, a solution containing 5-[(6-chloro-4-pyrimidinyl)oxy]-1H-indole (Intermediate IVa; 3.48 g, 14 mmol) and triethylamine (1.96 mL, 14 mmol) in CH$_2$Cl$_2$ (52 mL) is added dropwise. After stirring for a further 15 min an aqueous solution of ammonia (100 mL of 2.5%) is added and the mixture is extracted with CH$_2$Cl$_2$. The combined extracts are washed with saturated aqueous NaCl, dried (K$_2$CO$_3$) and the solvent is evaporated off under reduced pressure to afford a crude product which is recrystallised from EtOH to give the title compound as a colourless crystalline solid: NMR (400 MHz; DMSO-d6) δ 2.11 (m, 4H), 3.20 (t, J=8.3 Hz, 2H), 3.68 (m, 4H), 4.16 (t, J=8.5 Hz, 2H), 6.96 (dd, J=8.6 Hz, J=2.5 Hz, 1H), 7.09 (d, J=1.5 Hz, 1H), 7.28 (s, 1H), 7.52 (d, J=8.6 Hz, 1H), 7.84 (dd, J=8.8 Hz, J=2.5 Hz, 1H), 7.88 (d, J=8.8 Hz, 1H), 7.92 (d, J=2.3 Hz, 1H), 8.62 (s, 1H) and 8.77 (s, 1H).

The following compounds are prepared analogously by utilising the appropriate amine:

Intermediate IIb: 2,3-Dihydro-5-(6-chloro-4-pyrimidinyloxy)-N-(4-[(4-methyl-1-piperazinyl)methyl]-3-(trifluoromethyl)phenyl]-1H-indole-1-carboxamide, utilising 5-amino-2-[(4-methyl-1-piperazinyl)methyl]benzotrifluoride.

Intermediate IIc: 2,3-Dihydro-5-(6-chloro-4-pyrimidinyloxy)-N-[4-[(4-cyano-3-(trifluoromethyl)phenyl]-1H-indole-1-carboxamide m.p. 237-243° C., utilising 4-amino-2-(trifluoromethyl)benzonitrile.

Intermediate IId: 2,3-Dihydro-5-(6-chloro-4-pyrimidinyloxy)-N-[4-(4-methyl-1-piperazinyl)-3-(trifluoromethyl)phenyl]-1H-indole-1-carboxamide utilising 4-(4-methyl-1-piperazinyl)-3-(trifluoromethyl)-benzenamine.

Intermediate IIe: 2,3-Dihydro-5-(6-chloro-4-pyrimidinyloxy)-N-[4-(4-cyclopropyl-1-piperazinyl)-3-(trifluoromethyl)phenyl]-1H-indole-1-carboxamide utilising 4-(4-cyclopropyl-1-piperazinyl)-3-(trifluoromethyl)-benzenamine.

Intermediate IIf: 2,3-Dihydro-5-(6-chloro-4-pyrimidinyloxy)-N-[4-(3-pyridinyl)-3-(trifluoromethyl)phenyl]-1H-indole-1-carboxamide utilising 4-(3-pyridinyl)-3-(trifluoromethyl)-benzenamine.

Intermediate IIg: 2,3-Dihydro-5-(6-chloro-4-pyrimidinyloxy)-N-[4-(4-methyl-1H-imidazol-1-yl)-3-(trifluoromethyl)phenyl]-1H-indole-1-carboxamide utilising 4-(4-methyl-1H-imidazol-1-yl)-3-(trifluoromethyl)-benzenamine.

Intermediate IIh: 2,3-Dihydro-5-(6-chloro-4-pyrimidinyloxy)-N-[5-(4-methyl-1H-imidazol-1-yl)-3-(trifluoromethyl)phenyl]-1H-indole-1-carboxamide utilising 5-(4-methyl-1H-imidazol-1-yl)-3-(trifluoromethyl)-benzenamine.

Intermediate IIi: 2,3-Dihydro-5-(6-chloro-4-pyrimidinyloxy)-N-[5-(4-morpholinyl)-3-(trifluoromethyl)phenyl]-1H-indole-1-carboxamide utilising 5-(4-morpholinyl)-3-(trifluoromethyl)-benzenamine.

Intermediate IIj: 2,3-Dihydro-5-(6-chloro-4-pyrimidinyloxy)-N-[4-(4-morpholinylmethyl)-3-(trifluoromethyl)phenyl]-1H-indole-1-carboxamide utilising 4-(4-morpholinylmethyl)-3-(trifluoromethyl)-benzenamine.

Intermediate IIk: 2,3-Dihydro-5-(6-chloro-4-pyrimidinyloxy)-N-[4-(2-methyl-1H-imidazol-1-yl)methyl)-3-(trifluoromethyl)phenyl]-1H-indole-1-carboxamide utilising 4-(2-methyl-1H-imidazol-1-yl)methyl)-3-(trifluoromethyl)-benzenamine.

Intermediate IIl: 2,3-Dihydro-5-(6-chloro-4-pyrimidinyloxy)-N-[4-(diethylamino)methyl]-3-(trifluoromethyl)phenyl]-1H-indole-1-carboxamide utilising 4-(diethylamino)methyl)-3-(trifluoromethyl)-benzenamine.

Intermediate IIm: (±)-2,3-Dihydro-5-(6-chloro-4-pyrimidinyloxy)-N-[4-[(2-hydroxypropyl)amino]-3-(trifluoromethyl)phenyl]-1H-indole-1-carboxamide utilising (±)-1-[[4-Amino-2-(trifluoromethyl)phenyl]amino]-2-propanol.

Intermediate IIn: (±)-2,3-Dihydro-5-(6-chloro-4-pyrimidinyloxy)-N-[4-[3-(dimethylamino)-1-pyrrolidinyl]-3-(trifluoromethyl)phenyl]-1H-indole-1-carboxamide utilising (±)-1-(4-amino-2-(trifluoromethyl)phenyl)-N,N-dimethyl-3-pyrrolidinamine.

Intermediate IIo: 2,3-Dihydro-5-(6-chloro-4-pyrimidinyloxy)-N-[4-[(1-methyl-4-piperidinyl)oxy]-3-(trifluoromethyl)phenyl]-1H-indole-1-carboxamide utilising 4-[(1-methyl4-piperidinyl)oxy]-3-(trifluoromethyl)-benzenamine.

Intermediate IIp: [4-[[[2,3-Dihydro-5-(6-chloro-4-pyrimidinyloxy)-1H-indol-1-yl]carbonyl]amino]-2-(trifluoromethyl)phenoxy]-2-methylpropanoic acid, 1,1-dimethylethyl ester utilising 2-[4-amino-2-(trifluoromethyl)phenoxy]-2-methylpropanoic acid, 1,1-dimethylethyl ester.

Intermediate IIq: [4-[[(2,3-Dihydro-5-(6-chloro-4-pyrimidinyloxy)-1H-indol-1-yl]carbonyl]amino]-2-(trifluoromethyl)phenoxy]-2-methylpropanoic acid, 2-propenyl ester utilising 2-[4-amino-2-(trifluoromethyl)phenoxy]-2-methylpropanoic acid, 2-propenyl ester.

Intermediate IIr: 2,3-Dihydro-5-(6-chloro-4-pyrimidinyloxy)-N-[3-(trifluoromethyl)phenyl]-1H-indole-1-carboxamide utilising 3-(trifluoromethyl)-benzenamine.

Intermediate IIs: [4-[[(2,3-Dihydro-5-(6-chloro-4-pyrimidinyloxy)-1H-indol-1-yl]carbonyl]amino]-2-(trifluoromethyl)phenyl]-1-piperazinecarboxylic acid, 1,1-dimethylethyl ester utilising 4-[4-amino-2-(trifluoromethyl)phenyl]-1-piperazinecarboxylic acid, 1,1-dimethylethyl ester.

Intermediate IIt: 2,3-Dihydro-5-(6-chloro-4-pyrimidinyloxy)-N-[4-[(4-cyclopropyl-1-piperazinyl)methyl]-3-(trifluoromethyl)phenyl]-1H-indole-1-carboxamide Triethylamine is added to a stirred mixture of (4-(4-cyclopropyl-1-piperazinyl)methyl)-3-(trifluoromethyl)phenyl] carbamic acid, phenyl ester (Intermediate Va; 672 mg, 1.60 mmol) and 5-[(6-chloro-4-pyrimidinyl)oxy]-2,3-dihydro-1H-indole (437 mg, 1.76 mmol) in dry THF (12 mL). The mixture is heated at 65° C. for 14 h, cooled to 25° C. and the solvent is evaporated off under reduced pressure. The residue is treated with aqueous NaOH (10 mL of 1 M) and extracted with CH$_2$Cl$_2$. The combined extracts are washed with water, dried (K$_2$CO$_3$) and the solvent is evaporated off under reduced pressure to afford the title compound as a foam:

1H NMR (400 MHz, DMSO-D6) δ ppm 0.24-0.29 (m, 2 H), 0.35-0.41 (m, 2 H) 1.55-1.62 (m, 1 H), 2.28-2.41 (m, 4 H), 2.50-2.58 (m,4 H), 3.21 (t, J=8.6 Hz, 2 H) 3.51 (s, 2 H) 4.18 (t, J=8.6 Hz, 2 H), 6.98 (dd, J=8.8, 2.5 Hz, 1 H), 7.09-7.12 (m, 1 H), 7.29-7.32 (m, 1 H), 7.63 (d, J=8.6 Hz, 1 H) 7.82-7.87 (m, 1 H) 7.90 (d, J=8.6 Hz, 1 H), 7.97 (d, J=2.0 Hz, 1 H), 8.63-8.66 (m, 1 H), 8.83 (s, 1 H).

The following compounds are prepared analogously by utilising the appropriate phenylcarbamate:

Intermediate IIu: [4-[[(2,3-Dihydro-5-(6-chloro-4-pyrimidinylozy)-1H-indol-1-yl]carbonyl]amino]-2-(trifluoromethyl)phenylmethyl]-1-piperazinecarboxylic acid, 1,1-dimethylethyl ester utilising 4-[[4-[(phenoxycarbonyl)amino]-3-(trifluoromethyl)phenyl]methyl]-1-piperazinecarboxylic acid, 1,1-dimethylethyl ester (Intermediate Vb).

Intermediate IIv: 2,3-Dihydro-5-(6-chloro-4-pyrimidinyloxy)-N-[4-(1,1-dioxido-4-thiomorpholinyl)-3-(trifluoromethyl)phenyl]-1H-indole-1-carboxamide m.p. 248-255° C., utilising [4-(1,1-dioxido-4-thiomorpholinyl)-3-(trifluoromethyl)phenyl]carbamic acid, phenyl ester (Intermediate Vc).

Intermediate IIw: 2,3-Dihydro-5-(6-chloro-4-pyrimidinyloxy)-N-[4-(1-pyrrolidinylmethyl)-3-(trifluoromethyl)phenyl]-1H-indole-1-carboxamide utilising [4-(1-pyrrolidinylmethyl)-3-(trifluoromethyl)phenyl]carbamic acid, phenyl ester (Intermediate Vd).

Intermediate IIx: 2,3-Dihydro-5-(2-chloro-4-pyrimidinyloxy)-N-[4-[(4-methyl-1-piperazinyl)methyl]-3-(trifluoromethyl)phenyl]-1H-indole-1-carboxamide utilising 5-[(2-chloro-4-pyrimidinyl)oxy]-1H-indole and [4-(4-methyl-1-piperazinyl)methyl)-3-(trifluoromethyl)phenyl]carbamic acid, phenyl ester hydrochloride (Intermediate Ve).

Intermediates of formula (v):

Intermediate Va: [4-(4-Cyclopropyl-1-piperazinyl) methyl)-3-(trifluoromethyl)phenyl]carbamic acid, phenyl ester A mixture of 5-amino-2-[(4-cyclopropyl-1-piperazinyl) methyl]benzotrifluoride (1.80 g, 6.0 mmol) and pyridine (5.0 mL) in dry THF (25 mL) is added dropwise to a stirred solution of phenylchloroformate (0.83 mL, 6.6 mmol) in dry THF (25 mL) at −25° C. under an argon atmosphere. The mixture is stirred for 90 min, treated with EtOAc and washed with aqueous $Na_2CO_3$. The EtOAc solution is dried ($Na_2SO_4$) and the solvent is evaporated off under reduced pressure to afford the product which is purified by chromatography (silica gel, EtOAc/$CH_2Cl_2$ 1:1) to give the title compound as an oil: 1H NMR (400 MHz, DMSO-D6) δ ppm 0.22-0.29 (m, 2 H), 0.35-0.42 (m, 2 H), 1.55-1.62 (m, 1 H), 2.25-2.49 (m, 4 H), 2.50-2.61 (m, 4 H), 3.51 (br s, 2 H), 7.21-7.30 (m, 3 H), 7.40-7.46 (m, 2 H), 7.65-7.74 (m, 2 H), 7.87-7.92 (m, 1 H) 10.52 (br s, 1 H)

The following compounds are prepared analogously by utilising the appropriate amine:

Intermediate Vb: 4-[[4-[(Phenoxycarbonyl)amino]-3-(trifluoromethyl)phenyl]methyl]-1-piperazinecarboxylic acid, 1,1-dimethylethyl ester m.p. 143-147° C., utilising 4-[[4-amino-3-(trifluoromethyl)phenyl]methyl]-1-piperazinecarboxylic acid, 1,1-dimethylethyl ester.

Intermediate Vc: [4-(1,1-Dioxido-4-thiomorpholinyl)-3-(trifluoromethyl)phenyl]carbamic acid, phenyl ester utilising 4-(1,1-dioxido-4-thiomorpholinyl)-3-(trifluoromethyl)benzenamine.

Intermediate Vd: [4-(1-Pyrrolidinylmethyl)-3-(trifluoromethyl)phenyl]carbamic acid, phenyl ester utilising 4-(1-pyrrolidinylmethyl)-3-(trifluoromethyl)benzenamine.

Intermediate Ve: [4-(4-Methyl-1-piperazinyl)methyl)-3-(trifluoromethyl)phenyl]carbamic acid, phenyl ester hydrochloride utilising 5-amino-2-[(4-methyl-1-piperazinyl)methyl]benzotrifluoride Intermediates of formula (iv):

Intermediate 5-[(6-chloro-4-pyrimidinyl)oxy]-2,3-dihydro-1H-indole

Sodium cyanoborohydride (3.60 g, 57 mmol) is added in portions to a stirred solution of 5-[(6-chloro-4-pyrimidinyl) oxy]-1H-indole (3.68 g, 15 mmol) in acetic acid (20 mL) at 15° C. The mixture is then poured onto ice (100 g), basified with NaOH (100 mL of 30%) and extracted with ether. The combined extracts are washed with saturated aqueous NaCl, dried ($K_2CO_3$) and the solvent is evaporated off under reduced pressure to afford the product as an oil, which is used directly without further purification.

1H NMR (400 MHz, DMSO-D6) δ ppm 2.91 (t, J=8.4 Hz, 2 H), 3.44 (t, J=8.4 Hz, 2 H), 5.60 (br s, 1 H), 6.50 (d, J=8.2 Hz, 1 H), 6.72 (dd, J=8.2, 2.3 Hz, 1 H), 6.88 (s, 1H), 7.16 (s, 1 H), 8.62 (s, 1 H).

Utilising a similar procedure, but employing 5-[(2-chloro-4-pyrimidinyl)oxy]-1H-indole in lieu of 5-[(6-chloro-4-pyrimidinyl)oxy]-1H-indole afforded 5-[(2-chloro-4-pyrimidinyl)oxy]-2,3-dihydro-1H-indole, as an oil.

Intermediate 5-[(6-Chloro-4-pyrimidinyl)oxy]-1H-indole

5-Hydroxyindole (91.8 g, 0.69 mol) is added in portions to a stirred solution of NaOH (27.9 g, 0.69 mol) in water (560 m L) at 10° C., to give a solution which is then cooled to −10° C. A solution of 4,6-dichloropyrimidine (95.3 g, 0.63 mol) in acetone (560 mL) is then added over a period of 65 min. The mixture is stirred at 0° C. for 30 min and then the acetone is evaporated off under reduced pressure, to give a mixture which is extracted with $CH_2Cl_2$. The combined extracts are washed with cold aqueous NaOH (0.5 M), dried ($Na_2SO_4$) and the solvent is evaporated off under reduced pressure to afford the product to afford the crude product which is purified by chromatography (silica gel; eluent 10% EtOAc in $CH_2Cl_2$) and recrystallised from $CH_2Cl_2$—hexane to give the title compound as a colourless crystalline solid, m.p. 149-150° C. Utilising a similar procedure, but employing 2,4-dichloropyrimidine in lieu of 4,6-dichloropyrimidine afforded 5-[(2-chloro-4-pyrimidinyl)oxy]-1H-indole, as cream crystalline solid, m.p. 169-176° C.

Example 1

6-(6-Amino-pyrimidin-4-yloxy)-3,4-dihydro-2H-quinoline-1-carboxylic acid (3-trifluoromethyl-phenyl)-amide

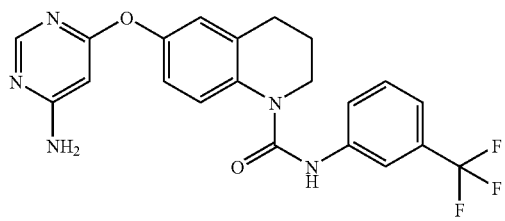

To a solution of 200 mg (0.83 mMol) of 6-amino-4-(1,2,3,4-tetrahydro-quinolin-6-yloxy)-pyrimidine (Step 1.3) in 5 ml of THF, 170 mg (94%; 0.85 mMol) of 3-trifluoromethyl-phenyl-isocyanate are added. After stirring for 1 h at rt, 1.5 g of $SiO_2$ are added and the reaction mixture concentrated in vacuo. The resulting powder is put on top of a $SiO_2$ chromatography column and the title compound eluated with EtOAc: MS: $[M+1]^+=430$; Anal.: C,H,N,F.

The starting material is prepared as follows:

Step 1.1: 6-Chloro-4-(quinolin-6-yloxy)-pyrimidine

A solution of 7.45 g (50 mMol) of 4,6-dichlor-pyrimidine, 7.64 g (50 mMol) of 6-hydroxy-chinolin and 2.0 g (50 mMol) NaOH dissolved in 200 ml of $H_2O$/acetone 1:1 is stirred for 3 h. The resulting solid is filtered off, washed with H₂O/acetone ans dried: m.p.: 136-137° C.; MS: [M+1]⁺=258.

Step 1.2: 6-Azido-4-(quinolin-6-yloxy)-pyrimidine

To a solution of 9.4 g (36.4 mMol) of 6-chloro-4-(quinolin-6-yloxy)-pyrimidine in 110 ml DMF, 4.74 g (73 mMol) NaN₃ are added. After stirring for 60 min at 60° C., the solution is diluted with EtOAc and water. The aqueous layer is separated off and extracted 2× with EtOAc. The organic phases are washed with water and brine, dried (Na₂SO₄) and concentrate in vacuo to give the crude title compound which is used as such in the next step: MS: [M+1]⁺=265.

Step 1.3: 6-Amino-4-(1,2,3,4-tetrahydro-quinolin-6-yloxy)-pyrimidine

The crude 6-azido-4-(quinolin-6-yloxy)-pyrimidine (36.4 mMol) in 324 ml of THF/acetic acid 4:1 is hydrogenated in the presence of 6 g Pd/C (10% Engelhard 4505). Then the catalyst is filtered off and the filtrate concentrated in vacuuo. The residue is put to pH 10 by addition of sat. Na₂CO₃ solution and extracted 3× with EtOAC. The organic phases are washed with water and brine, dried (Na₂SO₄) and after addition of 40 g of SiO₂ concentrate in vacuo. The resulting powder is put on top of a SiO₂ chromatography column and the title compound eluated with EtOAc: MS: [M+1]⁺=243.

Example 2

6-(6-Amino-pyrimidin-4-yloxy)-3,4-dihydro-2H-quinoline-1-carboxylic acid [3-(4-isopropylpiperazin-1-ylmethyl)-5-trifluoromethyl-phenyl]-amide

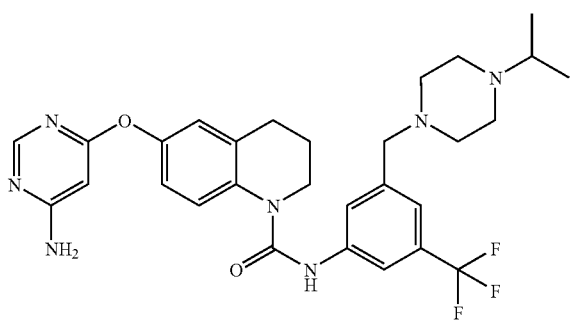

A solution of 83 mg (0.28 mMol) of triphosgene in 10 ml of CH₂Cl₂ is cooled to 2° C. Then a solution of 260 mg (0.86 mMol) of 3-(4-isopropylpiperazin-1-ylmethyl)-5-trifluoromethyl-aniline and 171 μl (1-23 mMol) Et₃N in 4 ml CH₂Cl₂ is added during 5 min. The mixture is stirred for 3 min at 2° C. and then warmed up to rt in a water bath. A solution of 200 mg (0.82 mMol) of 6-amino-4-(1,2,3,4-tetrahydro-quinolin-6-yloxy)-pyrimidine (Step 1.3) and 114 μl (0.82 mMol) Et₃N in 4 ml of CH₂Cl₂ is added during 5 min and stirring continued for 2 h at rt. EtOAc and a diluted solution of Na₂CO₃ is added to the reaction mixture. The aqueous phase is separated off and extracted twice with EtOAc. The organic layers are washed with water and brine, dried (Na₂SO₄) and concentrated. Column chromatography (SiO₂; EtOAc/EtOH/Et₃N 90:10:0→90:10:1) gives the title compound: TLC (EtOAc/EtOH/Et₃N 90:10:1): Rf=0.15; MS: [M+1]⁺=570; Anal.: C,H,N,F.

Example 3

6-(6-Methylamino-pyrimidin-4-yloxy)-3,4-dihydro-2H-quinoline-1-carboxylic acid (4-tert.butyl-phenyl)-amide

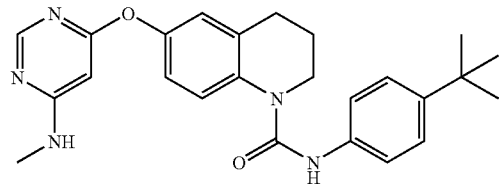

A solution of 90 mg (0.35 mMol) of 6-methylamino-4-(1,2,3,4-tetrahydro-quinolin-6-yloxy)-pyrimidine (Step 3.2) in 2 ml of THF and a solution of 63.3 mg (97%; 0-35 mMol) of 4-tert.butyl-phenyl-isocyanate in 4 ml ether are mixed and stirred for 30 min. After concentration of the reaction mixture, a chromatography (Combi Flash; hexane/EtOAc 1:2→EtOAc) gives the title compound: m.p.: 175-176° C.; MS: [M+1]⁺=432; Anal.: C,H,N.

The starting material is prepared as follows:

Step 3.1:
6-Methylamino-4-(quinolin-6-yloxy)-pyrimidine

A solution of 7.83 g (30.4 mMol) of 6-chloro-4-(quinolin-6-yloxy)-pyrimidine (step 1.1) and 121 ml of a 1 N MeNH₂ in THF is stirred for 7.5 h in a sealed vessel. After addition of 30 g of SiO₂, the mixture is concentrated and the resulting powder put on top of a chromatograph column (SiO₂; EtOAc). Eluation (EtOAc→EtOAc/EtOH 50:1→20:1→9:1) gives the title compound: m.p.: 173° C.; MS: [M+1]⁺=253; Anal.: C,H, N.

Step 3.2: 6-Methylamino-4-(1,2,3,4-tetrahydro-quinolin-6-yloxy)-pyrimidine

In the presence of 1 g of PtO₂ (Engelhard 7018), a solution of 2.63 g (10.4 mM) 6-methylamino-4-(quinolin-6-yloxy)-pyrimidine in 175 ml of THF/acetic acid 4:1 is hydrogenated. The catalyst is filtered off and the filtrate concentrated in vacuo. The residue is diluted with EtOAc and sat. Na₂CO₃ solution and extracted 3× with EtOAc. The organic phases are washed with water and brine, dried (Na₂SO₄) and partially concentrated in vacuo. The crystallized title compound can be filtered off and washed with EtOAc and DIPE: TLC(EtOAc): Rf=0.18; MS: [M+1]⁺=257. More product can be isolated from the filtrate by column chromatography (SiO₂; EtOAc).

Example 4

6-(6-Methylamino-pyrimidin-4-yloxy)-3,4-dihydro-2H-quinoline-1-carboxylic acid [3-(4-isopropylpiperazin-1-ylmethyl)-5-trifluoromethyl-phenyl]-amide

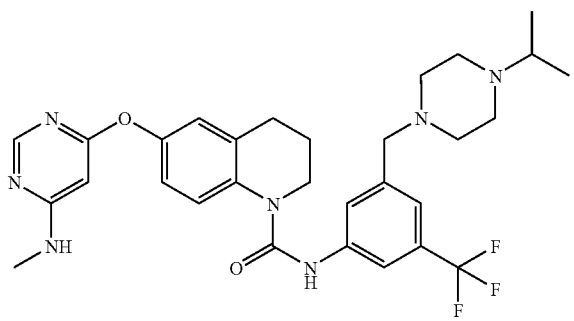

A solution of 41 mg (0.138 mMol) of triphosgene in 5 ml of CH$_2$Cl$_2$ is cooled to 2° C. Then a solution of 123 mg (0.41 mMol) of 3-(4-isopropylpiperazin-1-ylmethyl)-5-trifluoromethyl-aniline and 82 µl (0.59 mMol) Et$_3$N in 2 ml CH$_2$Cl$_2$ is added during 5 min. The mixture is stirred for 3 min at 2° C. and then warmed up to rt in a water bath. A solution of 100 mg (0.39 mMol) of 6-methylamino-4-(1,2,3,4-tetrahydro-quinolin-6-yloxy)-pyrimidine (Step 3.2) and 54 µl (0.39 mMol) Et$_3$N in 2 ml of CH$_2$Cl$_2$ is added during 5 min and stirring continued for 2 h at rt. EtOAc and a sat. solution of Na$_2$CO$_3$ is added to the reaction mixture. The aqueous phase is separated off and extracted twice with EtOAc. The organic layers are washed with water and brine, dried (Na$_2$SO$_4$) and concentrated. Column chromatography (Combi Flash; EtOAc/EtOH/Et$_3$N 95:5:0→90:10→90:10:1) gives the title compound: MS: [M+1]$^+$=584; TLC(EtOAc/EtOH/NH$_3$$^{conc.}$ 90:10:1): Rf=0.11; HPLC: $^A$t$_{Ret}$=10.1.

Example 5

The Following Compounds can be Obtained Analogously to Ex. 1 to 4

TABLE 1

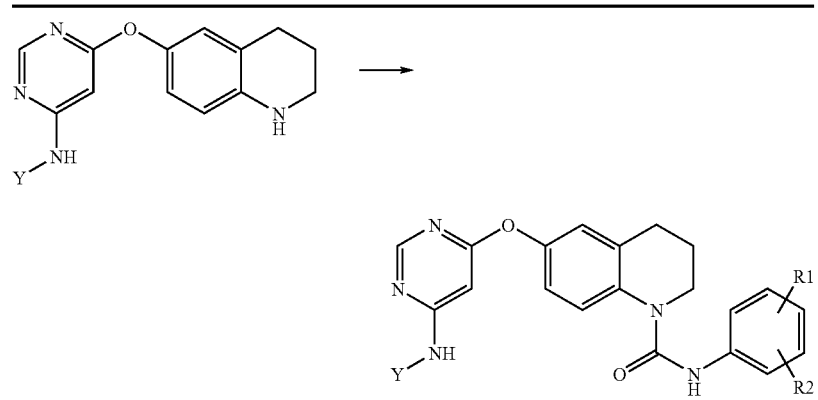

| | | Y | HPLC $^A$t$_{Ret}$ [min] | m.p. [° C.] | MS [M + 1]$^+$ | Anal. |
|---|---|---|---|---|---|---|
| a.1) | (3-trifluoromethylphenyl) | CH$_3$ | 12.3 | | 444 | |
| b.1) | (4-(4-methylpiperazin-1-ylmethyl)-3-trifluoromethylphenyl) | H | 9.3 | | 542 | C, H, N, F |

TABLE 1-continued
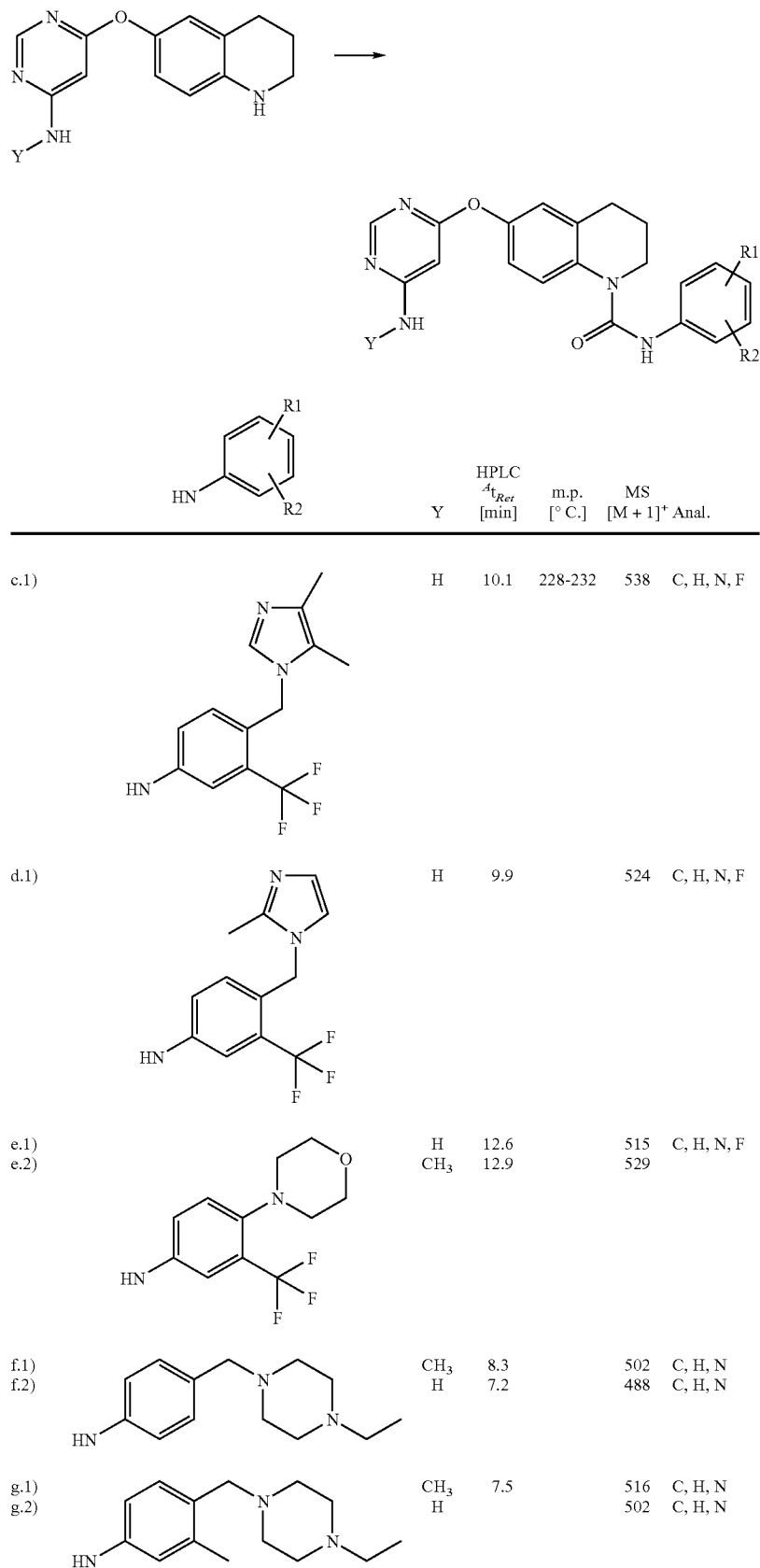
| | | Y | HPLC $^At_{Ret}$ [min] | m.p. [° C.] | MS [M + 1]$^+$ | Anal. |
|---|---|---|---|---|---|---|
| c.1) | | H | 10.1 | 228-232 | 538 | C, H, N, F |
| d.1) | | H | 9.9 | | 524 | C, H, N, F |
| e.1) | | H | 12.6 | | 515 | C, H, N, F |
| e.2) | | CH$_3$ | 12.9 | | 529 | |
| f.1) | | CH$_3$ | 8.3 | | 502 | C, H, N |
| f.2) | | H | 7.2 | | 488 | C, H, N |
| g.1) | | CH$_3$ | 7.5 | | 516 | C, H, N |
| g.2) | | H | | | 502 | C, H, N |

TABLE 1-continued
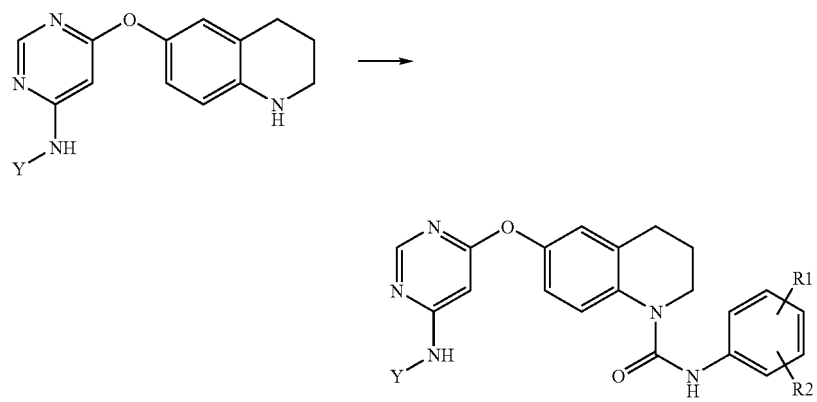
| | | Y | HPLC $t_{Ret}$ [min] | m.p. [°C.] | MS $[M+1]^+$ | Anal. |
|---|---|---|---|---|---|---|
| h.1) | | CH₃ | 11.7 | | 515 | C, H, N, F |
| h.2) | | H | 11.3 | | 501 | C, H, N, F |
| i.1) | | H | 9.4 | | 542 | C, H, N, F |
| j.1) | | H | 8.3 | | 522/524 | |
| k.1) | | H | 9.9 | | 584 | C, H, N, F |

TABLE 1-continued
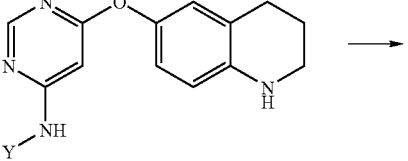
| | HNR1R2 | Y | HPLC $\Delta t_{Ret}$ [min] | m.p. [°C.] | MS $[M+1]^+$ | Anal. |
|---|---|---|---|---|---|---|
| l.1) | 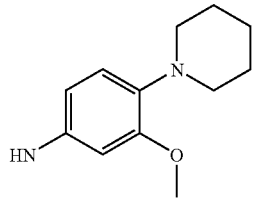 | H | 9.2 | 193-196 | 475 | C, H, N |
| m.1) | 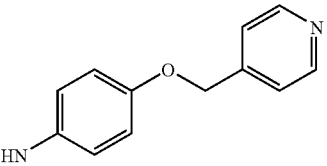 | H | 8.9 | | 469 | C, H, N |
| n.1) | 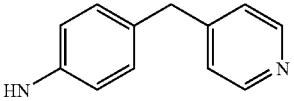 | H | 8.8 | | 453 | C, H, N |
| o.1) | 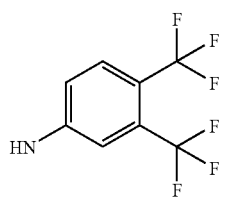 | H | 13.7 | | 498 | C, H, N |
| p.1) p.2) | ** 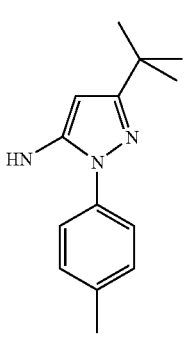 | H CH$_3$ | | 188-189 119-120 | 498 512 | |

TABLE 1-continued

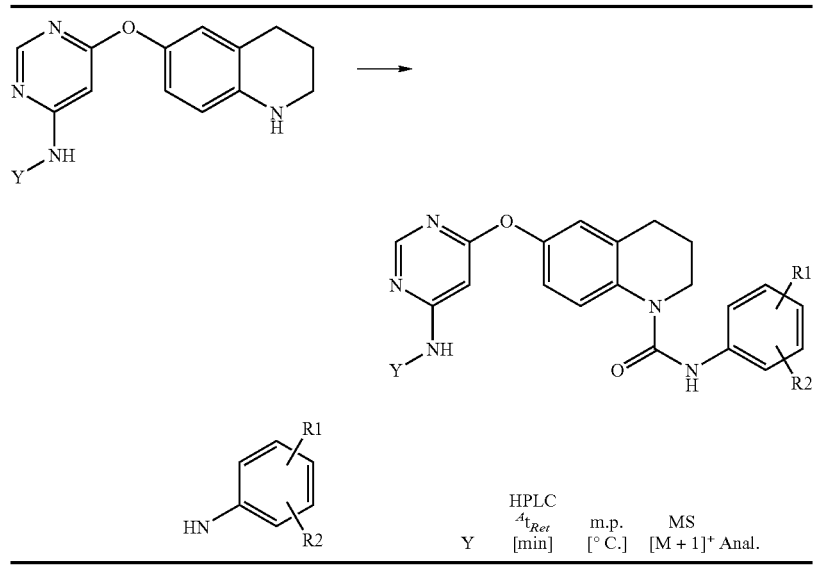

| | Y | HPLC $^A t_{Ret}$ [min] | m.p. [° C.] | MS [M + 1]⁺ | Anal. |
|---|---|---|---|---|---|

**)preparation of 3-amino-5-*tert*-butyl-2-(4-methyl-phenyl)-2H-pyrazole: *J. Med. Chem.* 2002, 45, 2994-3008

Example 6

7-(2-Amino-6-chloro-pyrimidin-4-yloxy)-2,3,4,5-tetrahydro-benzo[b]azepine-1-carboxylic acid (3-trifluoromethyl-phenyl)-amide

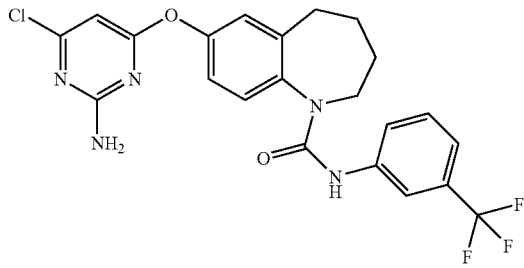

A mixture of 567 mg (1.62 mMol) of 7-hydroxy-2,3,4,5-tetrahydro-benzo[b]azepine-1-carboxylic acid (3-trifluoromethyl-phenyl)-amide (Step 6.2), 532 mg (3.24 mMol) 2-amino-4,6-dichloro-pyrimidine and 145 mg (3.62 mMol) NaOH in 5 ml acetone, 7 ml H₂O and 3 ml DMF is stirred at 60° C. for 24 h. Then it is poured into water and EtOAc, the aqueous phase separated off and extracted twice with EtOAc. The organic layers are washed with water and brine, dried (Na₂SO₄) and concentrated. Column chromatography (SiO₂; hexane/EtOAc 2:1→3:2) gives the title compound: m.p.: 175° C.; MS: [M+1]⁺=478/480; Anal.: C,H,N,Cl.

The starting material is prepared as follows:

Step 6.1: 7-Methoxy-2,3,4,5-tetrahydro-benzo[b]azepine-1-carboxylic acid (3-trifluoromethyl-phenyl)-amide A solution of 2.0 g (11.3 mMol) of 7-methoxy-2,3,4,5-tetrahydro-1H-benzo[b]azepine [*Monatsheft Chemie*, 97 (1966),150] and 2.28 g (97%; 11.8 mMol) of 3-trifluoromethyl-phenyl-isocyanate in 20 ml ether is stirred for 30 min in a icebath. After addition of hexane, the mixture is concentrated partially in vacuo and the crystallized product filtered off: m.p.: 108° C.; MS: [M+1]⁺=365; Anal.: C,H,N,F.

Step 6.2: 7-Hydroxy-2,3,4,5-tetrahydro-benzo[b]azepine-1-carboxylic acid (3-trifluoromethyl-phenyl)-amide A solution of 10 ml BBr₃ in 40 ml CH₂Cl₂ is cooled in dry ice and acetone. Then 2.43 g (6.67 mMol) of 7-methoxy-2,3,4,5-tetrahydro-benzo[b]azepine-1-carboxylic acid (3-trifluoromethyl-phenyl)-amide in 20 ml CH₂Cl₂ are added dropwise. The mixture is warmed up (−45 to −40° C.) and then stirred at this temperature for 1.5 h. The solution is poured into a mixture of 300 g ice, 150 ml sat. Na₂CO₃ solution and 200 ml EtOAc, the aqueous phase separated off and extracted twice with EtOAc. The organic layers are washed with water (2x) and brine, dried (Na₂SO₄) and concentrated. Crystallization from hexane gives the title compound: m.p.: 172-173° C.; MS: [M+1]⁺=351; Anal.: C,H,N,F.

Example 7

7-(2-Amino-pyrimidin-4-yloxy)-2,3,4,5-tetrahydro-benzo[b]azepine-1-carboxylic acid (3-trifluoromethyl-phenyl)-amide

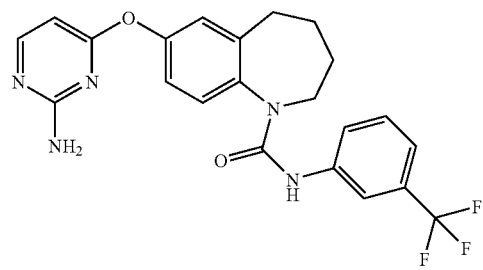

Hydrogenation of 0.26 g (0.54 mMol) 7-(2-amino-6-chloro-pyrimidin-4-yloxy)-2,3,4,5-tetrahydro-benzo[b]azepine-1-carboxylic acid (3-trifluoromethyl-phenyl)-amide in 15 ml methanol in the presence of 70 mg Pd/C (Engelhard 4505), filtration and column chromatography (SiO$_2$; hexane/EtOAc 3:2→2:3) of the filtrate gives the title compound: m.p.: 207° C.; MS: [M+1]$^+$=444/480; Anal.: C,H,N,F.

Example 8

7-(6-Chloro-pyrimidin-4-yloxy)-2,3,4,5-tetrahydro-benzo[b]azepine-1-carboxylic acid (3-trifluoromethyl-phenyl)-amide

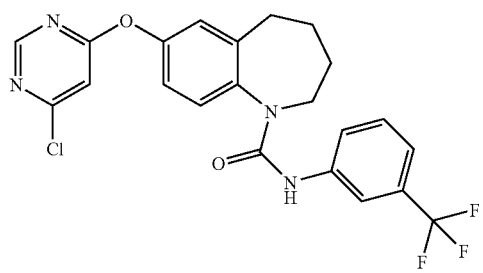

A mixture of 1.00 g (2.85 mMol) of 7-hydroxy-2,3,4,5-tetrahydro-benzo[b]azepine-1-carboxylic acid (3-trifluoromethyl-phenyl)-amide (Step 6.2) and 447 mg (3.0 mMol) 4,6-dichloro-pyrimidine in 8 ml acetone, 5 ml H$_2$O and 3 ml NaOH 1 M is stirred at rt for 5 h. The reaction mixture is diluted with water and EtOAc, the aqueous phase separated off and extracted twice with EtOAc. The organic layers are washed with water and brine, dried (Na$_2$SO$_4$) and concentrated. Chromatography (Combi Flash; hexane/EtOAc 19:1→7:3→1:4) gives the title compound: m.p.: 120° C.; MS: [M+1]$^+$=463/465; Anal.: C,H,N,F,Cl.

Example 9

7-(6-Methylamino-pyrimidin-4-yloxy)-2,3,4,5-tetrahydro-benzo[b]azepine-1-carboxylic acid (3-trifluoromethyl-phenyl)-amide

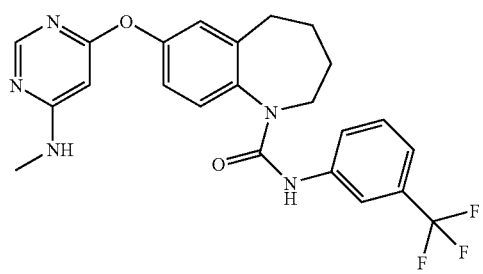

A solution of 0.23 g (0.50 mMol) of 7-(6-chloro-pyrimidin-4-yloxy)-2,3,4,5-tetrahydro-benzo[b]azepine-1-carboxylic acid (3-trifluoromethyl-phenyl)-amide in 5 ml THF and 2 ml MeNH$_2$ (2 M in THF) is kept at rt in a sealed vessel for 15 h. Then SiO$_2$ is added and the mixture concentrated in vacuo. The resulting powder is put on top of a chromatography column (SiO$_2$; hexane/EtOAc 95:5) and the title compound eluated with hexane/EtOAc 95:5→75:25→2:8: MS: [M+1]$^+$=458; Anal.: C,H,N,F.

Example 10

7-(6-Azido-pyrimidin-4-yloxy)-2,3,4,5-tetrahydro-benzo[b]azepine-1-carboxylic acid (3-trifluoromethyl-phenyl)-amide

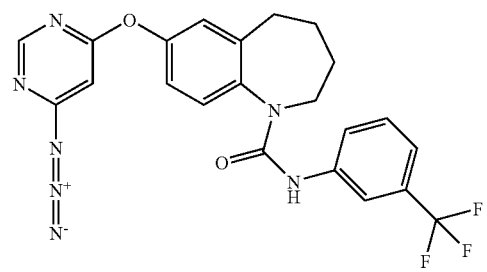

A solution of 300 mg (0.65 mMol) of 7-(6-chloro-pyrimidin-4-yloxy)-2,3,4,5-tetrahydro-benzo[b]azepine-1-carboxylic acid (3-trifluoromethyl-phenyl)-amide and 84 mg (1.3 mMol) NaN$_3$ in 3.8 ml DMF is stirred at 60° C. for 90 min. Then the solution is diluted with EtOAc and water, the aqueous layer separated off and extracted twice with EtOAc. The organic phases are washed with water and brine, dried (Na$_2$SO$_4$) and concentrated, yielding the title compound: MS: [M+1]$^+$=470; HPLC: $^A$t$_{Ret}$=16.9.

Example 11

7-(6-Amino-pyrimidin-4-yloxy)-2,3,4,5-tetrahydro-benzo[b]azepine-1-carboxylic acid (3-trifluoromethyl-phenyl)-amide

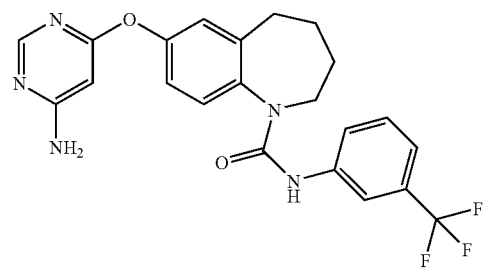

0.65 mMol of 7-(6-azido-pyrimidin-4-yloxy)-2,3,4,5-tetrahydro-benzo[b]azepine-1-carboxylic acid (3-trifluoromethyl-phenyl)-amide in 5 ml THF are hydrogenated in the presence of 0.1 g Pd/C (10% Engelhard 4505). Filtration and chromatography (Combi Flash; hexane/EtOAc 19:1→11:9→1:3) of the concentrated filtrate gives the title compound: MS: [M+1]$^+$=444; HPLC: $^A$t$_{Ret}$=10.6; Anal.: C,H, N,F.

Example 12

7-(2-Amino-6-chloro-pyrimidin-4-yloxy)-2,3,4,5-tetrahydro-benzo[b]azepine-1-carboxylic acid [3-trifluoromethyl-4-(4-methylpiperazin-1-ylmethyl)-phenyl]-amide

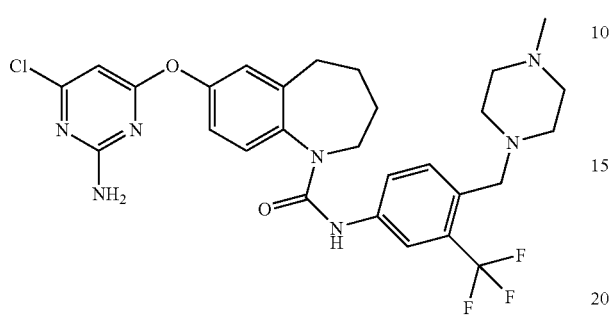

A mixture of 300 mg (0.65 mMol) of 7-hydroxy-2,3,4,5-tetrahydro-benzo[b]azepine-1-carboxylic acid [3-trifluoromethyl-4-(4-methylpiperazin-1-ylmethyl)-phenyl]-amide (Step 12.2), 106 mg (0.65 mMol) 2-amino-4,6-dichloro-pyrimidine and 26 mg (0.65 mMol) NaOH in 2 ml acetone, 2 ml H$_2$O and 1.2 ml DMEU is stirred at 60° C. for 12 h. Then the suspension is dissolved by addition of water and EtOAc, the aqueous phase separated off and extracted twice with EtOAc. The organic layers are washed with water and brine, dried (Na$_2$SO$_4$) and concentrated. Reversed phase MPLC (Gilson system) gives the title compound: MS: [M+1]$^+$=590/592; HPLC: $^A$t$_{Ret}$=12.7.

The starting material is prepared as follows:

Step 12.1: 7-Methoxy-2,3,4,5-tetrahydro-benzo[b]azepine-1-carboxylic acid [3-trifluoromethyl-4-(4-methylpiperazin-1-ylmethyl)-phenyl]-amide 586 mg (1.97 mMol) triphosgene are dissolved in 70 ml ice-cooled CH$_2$Cl$_2$. Then a solution of 1618 mg (5.92 mMol) 3-trifluoromethyl-4-(4-methylpiperazin-1-ylmethyl)-aniline and 1.179 ml (8.46 mMol) Et$_3$N in 12 ml CH$_2$Cl$_2$ is added during 11 min. After 3 additional minutes, the mixture is warmed up to rt by a water bath and then a solution of 1.00 g (5.64 mMol) of 7-methoxy-2,3,4,5-tetrahydro-1H-benzo[b]azepine [*Monatsheft Chemie*, 97 (1966), 150] and 786 µl (5.64 mMol) Et$_3$N in 18 ml CH$_2$Cl$_2$ is added during 10 min. After 2 h at rt, the mixture is diluted with water and EtOAc, the aqueous phase separated off and extracted twice with EtOAc. The organic layers are washed with water and brine, dried (Na$_2$SO$_4$) and concentrated. Column chromatography (SiO$_2$; EtOAc/EtOH/NH$_3$$^{conc.}$ 95:5:1→90:10:1) gives the title compound: MS: [M+1]$^+$=477; HPLC: $^A$t$_{Ret}$=12.0.

Step 12.2: 7-Hydroxy-2,3,4,5-tetrahydro-benzo[b]azepine-1-carboxylic acid [3-trifluoromethyl-4-(4-methylpiperazin-1-ylmethyl)-phenyl]-amide A solution of 38 ml BBr$_3$ (1 M in CH$_2$Cl$_2$) is cooled in dry ice and acetone. Then 1.828 g (3.8 mMol) of 7-methoxy-2,3,4,5-tetrahydro-benzo[b]azepine-1-carboxylic acid [3-trifluoromethyl-4-(4-methylpiperazin-1-ylmethyl)-phenyl]-amide in 20 ml CH$_2$Cl$_2$ are added dropwise. The mixture is stirred for 90 min at −78° C., warmed up (−40 to −30° C.) and then stirred at this temperature for 3.5 h. The solution is poured into a mixture of 300 g ice, 150 ml sat. Na$_2$CO$_3$ solution and 200 ml EtOAc, the aqueous phase separated off and extracted twice with EtOAc. The organic layers are washed with water (2×) and brine, dried (Na$_2$SO$_4$) and concentrated after addition of 15 g SiO$_2$. The resulting powder is put on top of a SiO$_2$ chromatography column. Eluation with EtOAC/EtOH 19:1→EtOAC/EtOH/Et$_3$N 90:10:1 gives the title compound: MS: [M+1]$^+$=463; Anal.: C,H,N,F.

Example 13

7-(2-Amino-pyrimidin-4-yloxy)-2,3,4,5-tetrahydro-benzo[b]azepine-1-carboxylic acid [3-trifluoromethyl-4-(4-methylpiperazin-1-ylmethyl)-phenyl]-amide

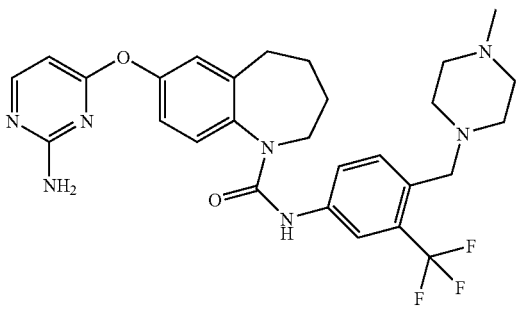

250 mg (0.42 mMol) of 7-(2-amino-6-chloro-pyrimidin-4-yloxy)-2,3,4,5-tetrahydro-benzo[b]azepine-1-carboxylic acid [3-trifluoromethyl-4-(4-methylpiperazin-1-ylmethyl)-phenyl]-amide in 35 ml methanol are hydrogenated in the presence of 160 mg Pd/C (10%; Engelhard 4505). The catalyst is filtered off, the filtrate diluted with EtOAc and sat. Na$_2$CO$_3$/H$_2$O 1:1 and the separated aqueous layer extracted twice with water. The organic layers are washed with water and brine, dried (Na$_2$SO$_4$) and concentrated. Reversed phase MPLC (Gilson system) gives the title compound: MS: [M+1]$^+$=556; HPLC: $^A$t$_{Ret}$=9.0.

Example 14

5-(6-Chloro-pyrimidin-4-yloxy)-2,3-dihydro-indole-1-carboxylic acid [4-(4-ethyl-piperazin-1-ylmethyl)-phenyl]-amide

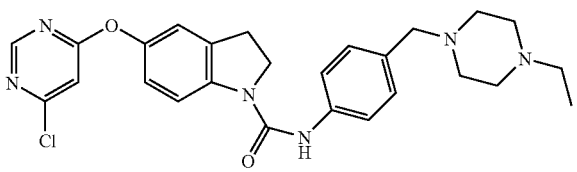

104 mg (0.35 mMol) triphosgene are dissolved in 13 ml ice-cooled CH$_2$Cl$_2$. Then a solution of 230 mg (1.05 mMol) 4-(4-ethylpiperazin-1-ylmethyl)-aniline and 209 µl (1.50 mMol) Et$_3$N in 6 ml CH$_2$Cl$_2$ is added during 8 min. After 3 additional minutes, the mixture is warmed up to rt by a water bath and then a solution of 1.0 mMol 5-(6-chloro-pyrimidin-4-yloxy)-2,3-dihydro-1H-indole (Step 14.1) and 139 µl (1.00 mMol) Et$_3$N in 6 ml CH$_2$Cl$_2$ is added during 8 min. After 2 h at rt, the mixture is diluted with sat. Na₂CO₃ solution/water 1:1 and EtOAc, the aqueous phase separated off and extracted twice with EtOAc. The organic layers are washed with water and brine, dried (Na₂SO₄) and concentrated. Crystallization from DIPE gives the title compound: MS: [M+1]⁺=493/495; TLC(CH₂Cl₂/MeOH/NH₃$^{conc.}$ 90:10:1): Rf=0.24; HPLC: $^{A}t_{Ret}$=10.5.

The starting material is prepared as follows:

Step 14.1: 5-(6-Chloro-pyrimidin-4-yloxy)-2,3-dihydro-1H-indole

A solution of 246 mg (1.0 mMol) of 5-(6-chloro-pyrimidin-4-yloxy)-1H-indole (WO 03/099771; Stage 163.1) in 5.5 ml acetic acid is cooled to 10-15° C. Then 314 mg (5 mMol) NaBH₃CN are added portionwise. After 1 h stirring, 9 g of ice are added and the mixture is concentrated partially in vacuo. The residue is dissolved in 25 ml 1 N NaOH and extracted three times with EtOAc. The organic layers are washed twice with water and brine, dried (Na₂SO₄) and concentrated at rt in vacuo: MS: [M+1]⁺=248; TLC(EtOAc/hexane 1:1): Rf=0.31.

Example 15

5-(6-Azido-pyrimidin-4-yloxy)-2,3-dihydro-indole-1-carboxylic acid [4-(4-ethyl-piperazin-1-ylmethyl)-phenyl]-amide

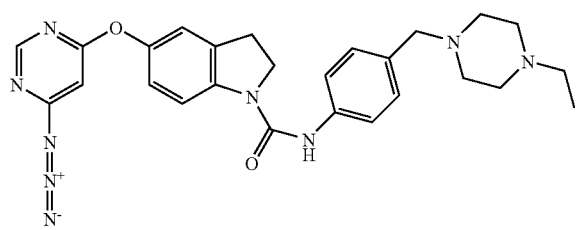

To a solution of 218 mg (0.44 mMol) 5-(6-chloro-pyrimidin-4-yloxy)-2,3-dihydro-indole-1-carboxylic acid [4-(4-ethyl-piperazin-1-ylmethyl)-phenyl]-amide in 2.5 ml DMF, 57 mg (0.88 mMol) NaN₃ are added at rt. After 2.5 h at 68° C., the resulting red solution is poured into water and extracted three times with EtOAc. The organic layers are washed twice with water and brine, dried (Na₂SO₄) and concentrated, yielding the title compound: MS: [M+1]⁺=500; HPLC: $^{A}t_{Ret}$=10.5.

Example 16

5-(6-Amino-pyrimidin-4-yloxy)-2,3-dihydro-indole-1-carboxylic acid [4-(4-ethyl-piperazin-1-ylmethyl)-phenyl]-amide

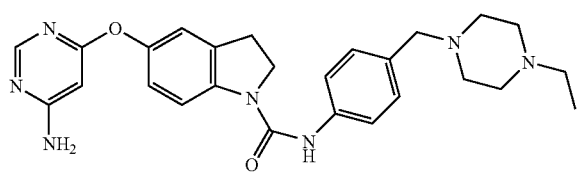

Hydrogenation of 0.38 mMol 5-(6-azido-pyrimidin-4-yloxy)-2,3-dihydro-indole-1-carboxylic acid [4-(4-ethyl-piperazin-1-ylmethyl)-phenyl]-amide in 10 ml THF in the presence of 70 mg Pd/C 10%, filtration, concentration of the filtrate, chromatography (Combi Flash; CH₂Cl₂/MeOH/NH₃$^{conc.}$ 98:2:0→90:10:1) and crystallization from DIPE gives the title compound: MS: [M+1]⁺=474; TLC(EtOAc/EtOH/NH₃$^{conc.}$ 80:20:1): Rf=0.09; Anal.: C,H,N.

Example 17

5-(6-Methylamino-pyrimidin-4-yloxy)-2,3-dihydro-indole-1-carboxylic acid [4-(4-ethyl-piperazin-1-ylmethyl)-phenyl]-amide

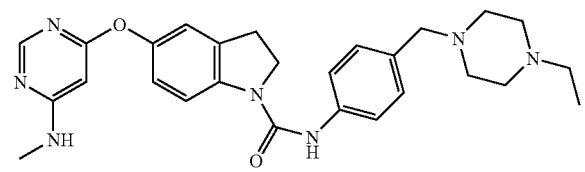

A solution of 134 mg (0.27 mMol) 5-(6-chloro-pyrimidin-4-yloxy)-2,3-dihydro-indole-1-carboxylic acid [4-(4-ethyl-piperazin-1-ylmethyl)-phenyl]-amide in 5 ml THF and 1.2 ml methylamin solution (2 M in THF) is stirred for 3 d in a sealed tube at rt. The reaction mixture is concentrated and the residue chromatographed by reversed phase MPLC (Gilson system), yielding the title compound: MS: [M+1]⁺=488; HPLC: $^{B}t_{Ret}$=11.5.

Example 18

5-{6-[3-(4-Methylpiperazin-1-yl)-propylamino]-pyrimidin-4-yloxy}-2,3-dihydro-indole-1-carboxylic acid (3-trifluormethyl-phenyl)-amide

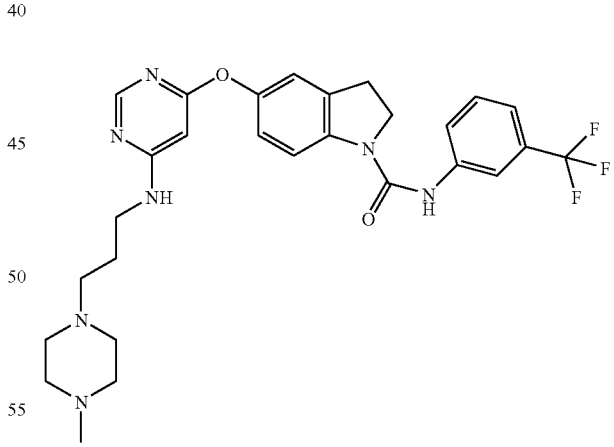

304 ring (0.70 mMol) of 5-(6-Chloro-pyrimidin-4-yloxy)-2,3-dihydro-indole-1-carboxylic acid (3-trifluoromethyl-phenyl)-amide (WO 03/099771; Stage 163), 477 µl (2.8 mMol) 1-(3-aminopropyl)-4-methyl-piperazine and a trace of NaI are heated in 10 ml isopropanol for 22 h at 50° C. Then the mixture is concentrated partially in vacuo. The residue is dissolved in EtOAc and NaHCO₃ and the aqueous layer extracted twice with EtOAc. The organic layers are washed twice with water and brine, dried (Na₂SO₄) and concentrated.

Column chromatography (SiO$_2$; CH$_2$Cl$_2$/MeOH/NH$_3^{conc.}$ 9:1:0→90:10:1) gives the title compound: m.p.: 163° C.; MS: [M+1]$^+$=556; TLC(CH$_2$Cl$_2$/MeOH/NH$_3^{conc.}$ 90:10:2): Rf=0.29.

Example 19

5-(6-Isopropylamino-pyrimidin-4-yloxy)-2,3-dihydro-indole-1-carboxylic acid (3-trifluormethyl-phenyl)-amide

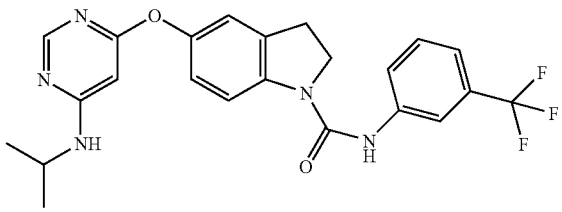

A solution of 261 mg (0.60 mMol) 5-(6-chloro-pyrimidin-4-yloxy)-2,3-dihydro-indole-1-carboxylic acid (3-trifluoromethyl-phenyl)-amide (WO 03/099771; ex. 163) in 15 ml isopropylamin is stirred for 18 h at rt and then concentrated in vacuo. The residue is dissolved in EtOAc and water and the aqueous layer extracted twice with EtOAc. -The organic layers are washed with water and brine, dried (Na$_2$SO$_4$) and concentrated. Column chromatography (SiO$_2$; EtOAc/hexane 1:1) gives the title compound: m.p.: 189° C.; MS: [M+1]$^+$= 458; TLC(EtOAc): Rf=0.45.

Example 20

5-(6-Amino-pyrimidin-4-yloxy)-2,3-dihydro-indole-1-carboxylic acid (4-tert.butyl-phenyl)-amide

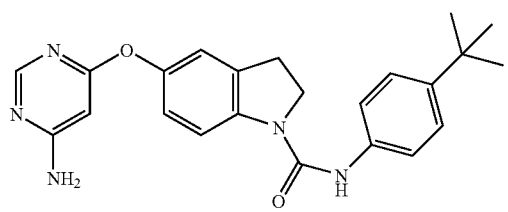

A solution of 70 mg (0.3 mMol) 5-(6-amino-pyrimidin-4-yloxy)-2,3-dihydro-indole (Step 20.3) and 70 mg (0.4 mMol) 4-tert.butyl-isocyanat in 2 ml THF is stirred for 90 min at rt. The reaction mixture is dissolved with EtOAc and water, the aqueous layer separated off and extracted twice with EtOAc. The organic phases are washed with water and brine, dried (Na$_2$SO$_4$) and concentrated. Column chromatography (SiO$_2$; EtOAc/hexane 1:1→3:1→9:1) gives the title compound: MS: [M+1]$^+$=404; TLC(EtOAc): Rf=0.16.

The starting material is prepared as follows:

Step 20.1: 5-(6-Azido-pyrimidin-4-yloxy)-1H-indole 490 mg (2.0 mMol) 5-(6-chloro-pyrimidin-4-yloxy)-indole (WO 03/099771; Stage 163.1) and 260 mg (4.0 mMol) NaN$_3$ in 3 ml DMF are stirred for 3 h at 90° C. Then the reaction mixture is poured into water and extracted three times with EtOAc. The organic layers are washed twice with water and brine, dried (Na$_2$SO$_4$) and concentrated, yielding the title compound: MS: [M+1]$^+$=253.

Step 20.2:
5-(6-Amino-pyrimidin-4-yloxy)-1H-indole 480 mg (1.9 mMol) 5-(6-azido-pyrimidin-4-yloxy)-1H-indole in 25 ml THF are hydrogenated in presence of 75 mg Pd/C 10%. Filtration, concentration of the filtrate and column chromatography (SiO$_2$; EtOAc/hexane 3:1→EtOAc) gives the title compound: MS: [M+1]$^+$=227; TLC(EtOAc): Rf=0.11

Step 20.3: 5-(6-Amino-pyrimidin-4-yloxy)-2,3-dihydro-1H-indole

Prepared from 136 mg (0.60 mMol) 5-(6-amino-pyrimidin-4-yloxy)-1H-indole analogously to Step 14.1: MS: [M+1]$^+$=229.

Example 21

5-(6-Methylamino-pyrimidin-4-yloxy)-2,3-dihydro-indole-1-carboxylic acid (4-tert.butyl-phenyl)-amide

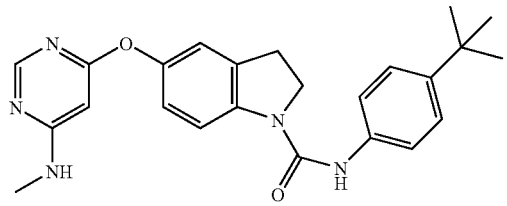

A solution of 70 mg (0.3 mMol) 5-(6-methylamino-pyrimidin-4-yloxy)-2,3-dihydro-indole (Step 21.2) and 70 mg (0.4 mMol) 4-tert.butyl-phenylisocyanat in 2 ml THF is stirred for 75 min at rt. The reaction mixture is dissolved with EtOAc and water, the aqueous layer separated off and extracted twice with EtOAc. The organic phases are washed with water and brine, dried (Na$_2$SO$_4$) and concentrated. Column chromatography (SiO$_2$; EtOAc/hexane 1:1→3:1→4:1) gives the title compound: MS: [M+1]$^+$=418; TLC(EtOAc): Rf=0.20.

The starting material is prepared as follows:

Step 21.1:
5-(6-Methylamino-pyrimidin-4-yloxy)-1H-indole

Dissolved in 6 ml methylamin solution (2 M in THF), 245 mg (1.0 mMol) 5-(6-chloro-pyrimidin-4-yloxy)-indole (WO 03/099771; Stage 163.1) are stirred for 24 h at rt and 8.5 h at 50° C. The concentrated reaction mixture is dissolved in water and EtOAC, the aqueous layer separated off and extracted twice with EtOAc. The organic layers are washed with water and brine, dried (Na$_2$SO$_4$) and concentrated. Column chromatography (SiO$_2$; EtOAc/hexane 1:1→3:1) gives the title compound: MS: [M+1]$^+$=241; TLC(EtOAc): Rf=0.15.

Step 21.2: 5-(6-Methylamino-pyrimidin-4-yloxy)-2,3-dihydro-1H-indole

Prepared from 72 mg (0.3 mMol) 5-(6-methylamino-pyrimidin-4-yloxy)-1H-indole analogously to Step 14.1: MS: [M+1]$^+$=243.

Example 22

5-(6-Amino-pyrimidin-4-yloxy)-2,3-dihydro-indole-1-carboxylic acid [3-(4-isopropylpiperazin-1-ylmethyl)-5-trifluoromethyl-phenyl]-amide

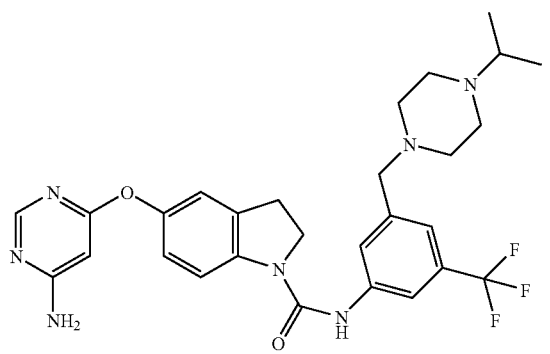

49 mg (0.16 mMol) triphosgene are dissolved in 5 ml ice-cooled $CH_2Cl_2$. Then a solution of 149 mg (0.49 mMol) 5-trifluoromethyl-3-(4-isopropylpiperazin-1-ylmethyl)-aniline and 98 μl (0.70 mMol) $Et_3N$ in 2 ml $CH_2Cl_2$ is added during 5 min. After 3 additional minutes, the mixture is warmed up to rt by a water bath and then a solution of 0.47 mMol 5-(6-amino-pyrimidin-4-yloxy)-2,3-dihydro-1H-indole (Step 20.3) and 65 μl (0.47 mMol) $Et_3N$ in 2 ml $CH_2Cl_2$ is added during 5 min. After 2 h at rt, the mixture is diluted with sat. $Na_2CO_3$ solution/water 1:1 and EtOAc, the aqueous phase separated off and extracted twice with EtOAc. The organic layers are washed with water and brine, dried ($Na_2SO_4$) and concentrated. Reversed phase MPLC (Gilson system) gives the title compound: MS: $[M+1]^+=556$; HPLC: $^At_{Ret}=9.7$.

Example 23

The Following Compounds can be Obtained Analogously to Ex. 14 to 22

TABLE II

| | HN-aryl(R1,R2) | Y | HPLC $^At_{Ret}$ [min] | m.p. [° C.] | MS $[M+1]^+$ | Anal. |
|---|---|---|---|---|---|---|
| a.1) | 4-Cl, 3-CF3 phenyl | Me—NH | | | 464 | |
| a.2) | | $H_2N$ | | | 450 | |
| b.1) | 4-Me phenyl | Me—NH | | 213 | 376 | C, H, N, F |
| b.2) | | $H_2N$ | | 230 | 362 | |
| c.1) | 4-morpholino, 3-CF3 phenyl | Cl | 16.5 | 212-214 | 520/522 | |
| c.2) | | $N_3$ | 16.4 | 199-200 | 527 | |
| c.3) | | $H_2N$ | 12.5 | | 501 | |
| c.4) | | Me—NH | | | 515 | |
| c.5) | | cyclopropyl-NH | | | 599 | |
| c.6) | | Et—NH | | | | |
| c.7) | | trans-4-hydroxycyclohexyl-NH | | | | |

TABLE II-continued

[Structure: pyrimidine(Y)-O-indoline-N-C(=O)-NH-phenyl(R1,R2)]

| | R1/R2 aniline group | Y | HPLC $^A t_{Ret}$ [min] | m.p. [°C.] | MS [M + 1]$^+$ | Anal. |
|---|---|---|---|---|---|---|
| d.1) | 4-[(4-ethylpiperazin-1-yl)methyl]-3-methylaniline | Cl | 10.4 | | 507/509 | C, H, N |
| d.2) | | N$_3$ | 10.9 | | 514 | |
| d.3) | | H$_2$N | | | 488 | |
| e.1) | 3-(N,N-dimethylcarbamoyl)-5-(trifluoromethyl)aniline | Cl | 14.9 | | 513 | C, H, N, F |
| e.2) | | N$_3$ | 11.2 | | 487 | |
| e.3) | | H$_2$N | | | | |
| f.1) | 4-methyl-3-(trifluoromethyl)aniline | Cl | 16.7 | | 449/451 | |
| f.2) | | N$_3$ | 16.6 | | 456 | |
| f.3) | | H$_2$N | 12.5 | | 430 | |
| g.1) | 4-fluoro-3-(trifluoromethyl)aniline | Cl | 16.4 | | 453/455 | |
| g.2) | | N$_3$ | 16.2 | | 434 | |
| g.3) | | H$_2$N | 12.1 | | | |
| h.1) | *) 2-(trifluoromethyl)pyridin-4-amine | Cl | 14.9 | | 436/438 | |
| h.2) | | N$_3$ | 10.6 | | 443 | |
| h.3) | | H$_2$N | | | 417 | |
| i.1) | 4-[(4-methylpiperazin-1-yl)methyl]-3-(trifluoromethyl)aniline | H$_2$N | | 224-225 | 528 | |

TABLE II-continued

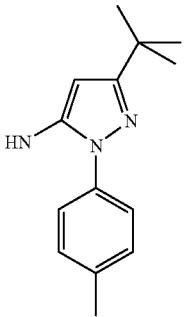

| | | Y | HPLC $^A t_{Ret}$ [min] | m.p. [° C.] | MS $[M + 1]^+$ | Anal. |
|---|---|---|---|---|---|---|
| j.1) | **) | H₂N | | 149-150 | 484 | |
| j.2) | | CH₃ | | 126-128 | 498 | |

*) preparation of 4-amino-2-trifluoromethyl-pyridine: *J. Med. Chem.* 1993, 36, 733-746.
**) preparation of 3-amino-5-*tert*-butyl-2-(4-methyl-phenyl)-2H-pyrazole: *J. Med. Chem.* 2002, 45, 2994-3008

Example 24

5-(2-Amino-6-chloro-pyrimidin-4-yloxy)-2,3-dihydro-indole-1-carboxylic acid (3-trifluoromethyl-phenyl)-amide

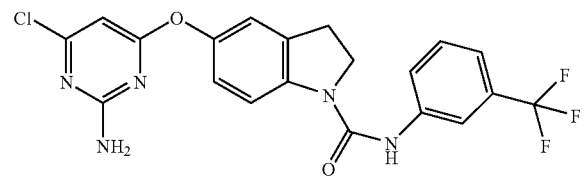

A solution of 226 mg (1.21 mMol) 3-trifluoromethyl-phenylisocyanat in 5 ml THF is added dropwise to 302 mg (1.15 mMol) 5-(2-amino-6-chloro-pyrimidin-4-yloxy)-2,3-dihydro-indole (Step 24.2) in 5 ml THF. After 30 min, the reaction mixture is diluted with EtOAc and water, the aqueous layer separated off and extracted twice with EtOAc. The organic phases are washed with water and brine, dried (Na₂SO₄) and concentrated. Chromatography (Combi Flash; EtOAc/hexane 1:4→2:5) gives the title compound: MS: [M+1]⁺=450; TLC(hexane/EtOAc 3:2): Rf=0.08; HPLC: $^A t_{Ret}$=15.6.

The starting material is prepared as follows:

Step 24.1: 5-(2-Amino-6-chloro-pyrimidin-4-yloxy)-1H-indole 10 g (61 mMol) 2-amino-4,6-dichloro-pyrimidine and 8.1 g (61 mMol) 5-hydroxyindole are suspended in 250 ml acetone. Then 120 ml 1 N NaOH in water are added and the mixture is stirred at an oilbath temperature of 70° C. for 2 h. The reaction mixture is partially concentrated and the residue diluted with water. Extraction with 3 portions of EtOAc, washing the organic layers twice with water and brine, drying (Na₂SO₄), addition of 100 g SiO₂ and concentration in vacuo gives a powder. This is put on top of a chromatography column (SiO₂; EtOAc/hexane 3:7) and eluted with EtOAc/hexane 3:7. Crystallization from hexane gives the title compound: m.p.: 192° C.; MS: [M+1]⁺=261; HPLC: $^A t_{Ret}$=12.4.

Step 24.2: 5-(2-Amino-6-chloro-pyrimidin-4-yloxy)-2,3-dihydro-1H-indole

Prepared from 300 mg (1.15 mMol) 5-(2-amino-6-chloro-pyrimidin-4-yloxy)-1H-indole analogously to Step 14.1.

Example 25

5-(2-Amino-pyrimidin-4-yloxy)-2,3-dihydro-indole-1-carboxylic acid (3-trifluoromethyl-phenyl)-amide

A solution of 170 mg (0.38 mMol) 5-(2-amino-6-chloro-pyrimidin-4-yloxy)-2,3-dihydro-indole-1-carboxylic acid (3-trifluoromethyl-phenyl)-amide in 19 ml EtOH/EtOAc 1:1 in hydrogenated in the presence of 80 mg Pd/C (10%; Engelhard 4505). The catalyst is filtered off and the filtrate diluted with EtOAc and sat. $Na_2CO_3/H_2O$ 1:1. The aqueous layer is extracted twice with EtOAc. The organic phases are washed with water and brine, dried ($Na_2SO_4$) and concentrated. Chromatography (Combi Flash; EtOAc/hexane 3:2→EtOAc) gives the title compound: MS: $[M+1]^+$=416; TLC(hexane/EtOAc 3:7): Rf=0.14; HPLC: $^At_{Ret}$=12.0.

Example 26

5-(2-Amino-pyrimidin-4-yloxy)-2,3-dihydro-indole-1-carboxylic acid (2-trifluoromethyl-pyridin-4-yl)-amide

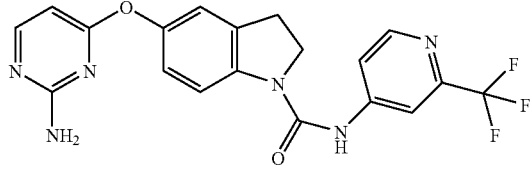

72 mg (0.24 mMol) triphosgene are dissolved in 10 ml ice-cooled $CH_2Cl_2$. Then a solution of 119 mg (0.74 mMol) 4-amino-2-trifluoromethyl-pyridine [*J. Med. Chem*, 36 (1993), 733] and 146 µl (1.05 mMol) $Et_3N$ in 2 ml $CH_2Cl_2$ is added during 5 min. After 3 additional minutes, a solution of 0.7 mMol 5-(2-amino-pyrimidin-4-yloxy)-2,3-dihydro-1H-indole (Step 26.2) and 98 µl (0.7 mMol) $Et_3N$ in 2 ml $CH_2Cl_2$ and 3 ml THF is added during 12 min. After 16 h at rt, the mixture is diluted with sat. $Na_2CO_3$ solution and EtOAc, the aqueous phase separated off and extracted twice with EtOAc. The organic layers are washed with water and brine, dried ($Na_2SO_4$) and concentrated after addition of 1.5 g $SiO_2$. This powder is put on top of a chromatography column ($SiO_2$; EtOAc) and eluted with EtOAc giving the title compound: MS: $[M+1]^+$=417; HPLC: $^At_{Ret}$=10.6.

The starting material is prepared as follows:

Step 26.1:

5-(2-Amino-pyrimidin-4-yloxy)-1H-indole

A solution of 1.00 g (3.84 mMol) 5-(2-amino-6-chloro-pyrimidin-4-yloxy)-1H-indole (Step 24.1) and 562 µl (4.0 mMol) $Et_3N$ in 170 ml THF is hydrogenated in the presence of 0.7 g Pd/C (10%; Engelhard 4505). The catalyst is filtered off, the filtrate concentrated and the residue dissolved in EtOAc and $H_2O$. The aqueous layer is extracted twice with water. The organic layers are washed with water and brine, dried ($Na_2SO_4$) and concentrated. Column chromatography ($SiO_2$; EtOAc/hexane 4:1) gives the title compound: MS: $[M+1]^+$=227; TLC(EtOAc/hexane 4:1): Rf=0.4; HPLC: $^At_{Ret}$= 8.5.

Step 26.2: 5-(2-Amino-pyrimidin-4-yloxy)-2,3-dihydro-1H-indole

A solution of 160 mg (0.70 mMol) of 5-(2-amino-pyrimidin-4-yloxy)-1H-indole in 4 ml acetic acid is cooled to 10-15° C. Then 222 mg (3.5 mMol) $NaBH_3CN$ are added. After 1 h stirring at rt, 8 g of ice are added. Then the mixture is made basic by addition of 1 N NaOH and extracted three times with EtOAc. The organic layers are washed with water and brine, dried ($Na_2SO_4$) and concentrated at rt in vacuo: MS: $[M+1]^+$= 229.

Example 27
The Following Compounds can be Obtained Analogously to Ex. 24 to 26
TABLE III
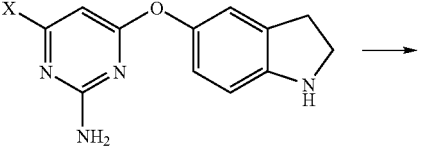
→
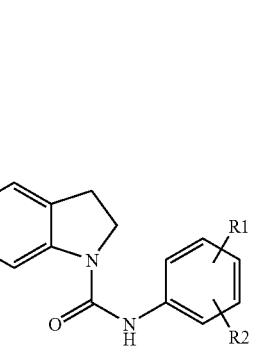
| | R1/R2 (HN-aryl) | X | HPLC $A_{t_{Ret}}$ [min] | m.p. [°C.] | MS $[M + 1]^+$ | Anal. |
|---|---|---|---|---|---|---|
| a.1) | 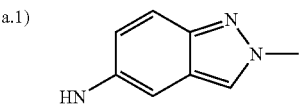 | H | H | 12.7 | 430 | C, H, N, F |
| b.1) | 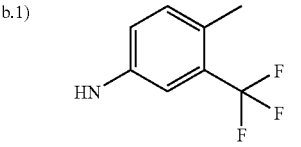 | H | H | 12.2 | 434 | |
| c.1) | 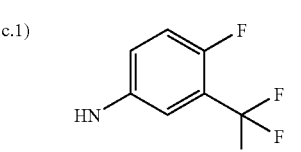 | H | H | 9.1 | 402 | |
| d.1) | 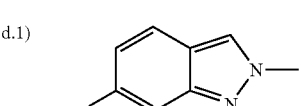 | H | H | | | |
| e.1) | 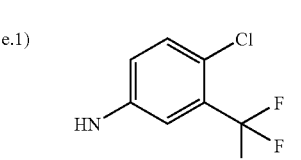 | H | H | 12.7 | 430 | C, H, N, F |

Example 28

6-(6-Amino-pyrimidin-4-yloxy)-3,4-dihydro-2H-quinoline-1-carboxylic acid (4-pyrrolidin-1-ylmethyl-3-trifluoromethyl-phenyl)-amide

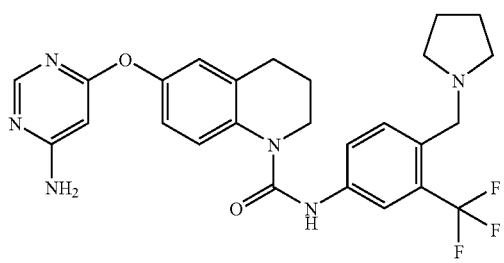

A solution of 85 mg (0.35 mMol) 6-amino-4-(1,2,3,4-tetrahydro-quinolin-6-yloxy)-pyrimidine (Step 1.3) and 0.33 mMol (4-pyrrolidin-1-ylmethyl-3-trifluoromethyl-phenyl)-carbamic acid phenyl ester in 2 ml DMSO is heated to 60° C. Then 65 μl (0.38 mMol) diisopropyl-ethyl-amine are added and stirring at 60° C. continued for 3 h. The resulting solution is poured into water containing 30 mg KOH and EtOAc, the aqueous layer separated off and extracted 2× with EtOAc. The organic phases are washed with water and brine, dried (Na$_2$SO$_4$) and concentrated. Chromatography (Combi Flash; EtOAC→EtOAc/(EtOH+1.5% Et$_3$N) 19:1) gives the title compound: MS: [M+1]$^+$=513; HPLC: $^r$A$_{Ret}$=8.8; Anal.: C,H, N,F.

The starting material is prepared as follows:

Step 28.1: (4-Pyrrolidin-1-ylmethyl-3-trifluoromethyl-phenyl)-carbamic acid phenyl ester A solution of 49 μl (0.39 mMol) phenyl chloroformiate in 1.5 ml THF is cooled to −70° C. Then a solution of 81 mg (0.33 mMol) 4-pyrrolidin-1-ylmethyl-3-trifluoromethyl-phenylamine and 0.3 ml pyridine in 1.5 ml THF is added dropwise. After 1 h, it is poured into a mixture of 20 g ice, 40 ml sat. Na$_2$CO$_3$/water 1:3 and 40 ml EtOAc. The aqueous layer is separated off and extracted 2× with EtOAc. The organic phases are washed with water and brine, dried (Na$_2$SO$_4$) and concentrated to the title compound: MS: [M+1]$^+$=365; HPLC: $^A$t$_{Ret}$=11.1.

Example 29

6-(2-Amino-pyrimidin-4-yloxy)-3,4-dihydro-2H-quinoline-1-carboxylic acid (3-trifluoromethyl-phenyl)-amide

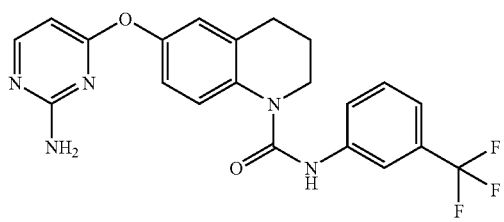

To a solution of 242 mg (1 mmol) 4-(1,2,3,4-tetrahydro-quinolin-6-yloxy)-pyrimidin-2-ylamine (Step 29.2) in 5 mL of dry THF are added 205 mg (1.1 mmol) of 3-trifluoromethyl-phenylisocyanate at RT. The solution is stirred for 2 h at RT and then the THF is evaporated. The residue is purified by flash-chromatography on silica gel using dichloromethane/methanol 95:5 as eluent. Fractions with pure compound are pooled and evaporated to give the title compound as an amorphous material: MS: [M+1]$^+$=430; HPLC: $^C$t$_{Ret}$=2.14; TLC (dichloromethane/methanol 95:5): Rf=0.45.

The starting material is prepared as follows:

Step 29.1: 4-Chloro-6-(quinolin-6-yloxy)-pyrimidin-2-ylamine

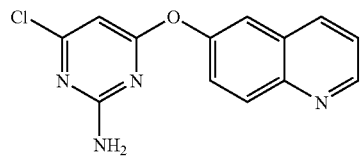

To a mixture containing 7.25 g (0.05 mol) 6-hydroxy-quinoline, 8.25 g (0.05 mol) 2-amino-4,6-dichloropyrimidine in 300 mL of water/acetone 1:1 are added 2.0 g (0.05 mol) sodium hydroxide. On heating a clear solution is first obtained from which a thick precipitate separates. Stirring under reflux is continued for a total of 6 h. The mixture is cooled, filtered and the solid washed with acetone/water 1.1 and dried. The title compound is obtained as a solid: map. 248-250° C.; MS: [M+1]$^+$=273; HPLC: $^C$t$_{Ret}$=1.30; TLC (dichloromethane/methanol 95:5): Rf=0.46.

Step 29.2: 4-(1,2,3,4-Tetrahydro-quinolin-6-yloxy)-pyrimidin-2-ylamine

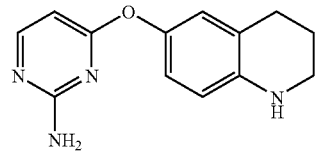

A solution of 5.4 g (0.02 mol) 4-chloro-6-(quinolin-6-yloxy)-pyrimidin-2-ylamine in 600 mL of THF is hydrogenated during 21 h in the presence of 1.2 g Pd/C (10% Engelhard 4505). Then the catalyst is filtered off and the filtrate concentrated in vacuuo. The residue is partitioned between ethyl acetate and conc. sodium bicarbonate solution and the organic layer washed with brine, dried and evaporated. The crude product is purified by flash-chromatography on silica gel using dichloromethane/methanol 95:5 as eluent. Fractions with pure compound are pooled and evaporated. The crystalline material is triturated with ether, filtered and dried to give the title compound: m.p. 180-182° C.; MS: [M+1]$^+$= 243; TLC (dichloromethane/methanol 95:5): Rf=0.4.

Example 30

6-(2-Amino-pyrimidin-4-yloxy)-3,4-dihydro-2H-quinoline-1-carboxylic acid (3,5-bis-trifluoromethyl-phenyl)-amide

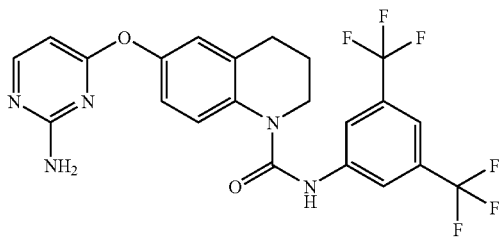

The title compound can be obtained analogously to Example 29: MS: [M+1]$^+$=498; HPLC: $^Ct_{Ret}$=2.15; TLC (dichloromethane/methanol 95:5): Rf=0.45.

Example 31

6-(2-Amino-pyrimidin-4-yloxy)-3,4-dihydro-2H-quinoline-1-carboxylic acid (4-chloro-3-trifluoromethyl-phenyl)-amide

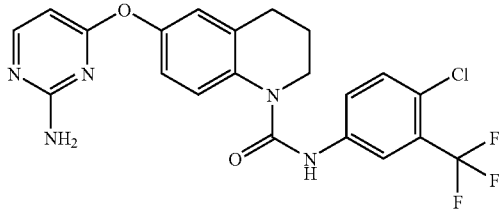

The title compound can be obtained analogously to Example 29: MS: [M+1]$^+$=462 and 464; HPLC: $^Ct_{Ret}$=2.02; TLC (dichloromethane/methanol 95:5): Rf=0.45.

Example 32

6-(2-Amino-pyrimidin-4-yloxy)-3,4-dihydro-2H-quinoline-1-carboxylic acid (4-fluoro-3-trifluoromethyl-phenyl)-amide

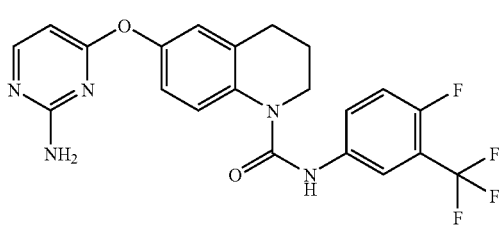

The title compound can be obtained analogously to Example 29: MS: [M+1]$^+$=449; HPLC: $^Ct_{Ret}$=1.94; TLC (dichloromethane/methanol 95:5): Rf=0.45.

Example 33

6-(2-Amino-pyrimidin-4-yloxy)-3,4-dihydro-2H-quinoline-1-carboxylic acid [4-(4-methyl-piperazin-1-ylmethyl)-3-trifluoromethyl-phenyl]-amide

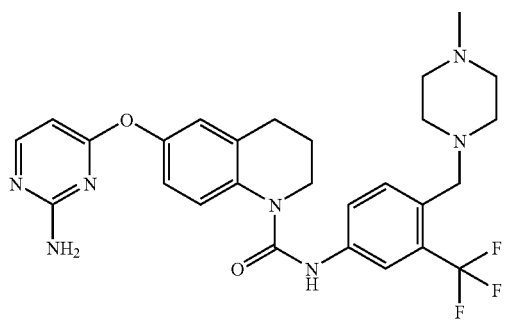

The title compound can be obtained analogously to Example 26, starting with 4-(1,2,3,4-tetrahydro-quinolin-6-yloxy)-pyrimidin-2-ylamine and 4-(4-methyl-piperazin-1-ylmethyl)-3-trifluoromethyl-phenylamine: m.p. 120-123° C.; MS: [M+1]$^+$=542; HPLC: $^Ct_{Ret}$=1.37; TLC (dichloromethane/ethanol 9:1+1% conc. ammonia): Rf=0.25.

Example 34

6-(2-Amino-pyrimidin-4-yloxy)-3,4-dihydro-2H-quinoline-1-carboxylic acid (4-morpholin-4-ylmethyl-3-trifluoromethyl-phenyl)-amide

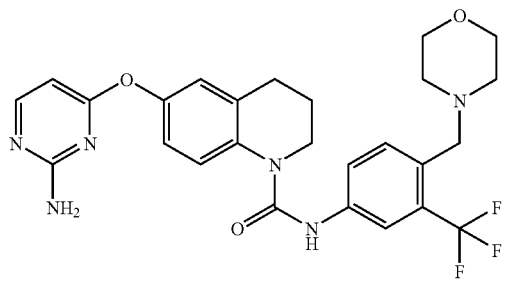

The title compound can be obtained analogously to Example 26, starting with 4-(1,2,3,4-tetrahydro-quinolin-6-yloxy)-pyrimidin-2-ylamine and 4-morpholin-4-ylmethyl-3-trifluoromethyl-phenylamine: MS: [M+1]$^+$=529; HPLC: $^Dt_{Ret}$= 7.71; TLC (dichloromethane/ethanol 96:4): Rf=0.16.

Example 35

[6-[[1-[[4-(4-Morpholinyl)-3-(trifluoromethyl)phenylamino]carbonyl]-1H-indol-5-yl]oxy]-4-pyrimidinyl]acetamide

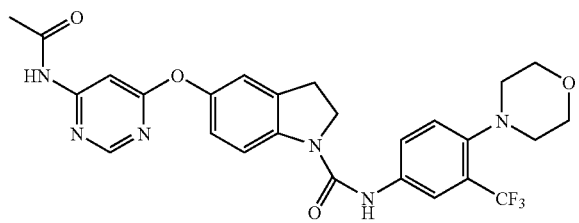

A mixture of 2,3-dihydro-5-(6-chloro-4-pyrimidinyloxy)-N-[4-(4-morpholinyl)-3-(trifluoromethyl)phenyl]-1H-indole-1-carboxamide (Intermediate IIa; 1.30 g, 2.5 mmol), acetamide (0.22 g, 3.75 mmol), (9,9-dimethyl-9H-xanthene-4,5-diyl)bis[diphenylphosphine] (90 mg, 0.15 mmol), tris(dibenzylideneacetone)dipalladium (45 mg, 0.05 mmol), caesium carbonate (1.14 g, 3.5 mmol) in dry dioxan (10 mL) is heated under an argon atmosphere at 70° C. for 15 h. The cooled suspension is filtered and the residue is dissolved in DMF (50 mL). The resulting solution is filtered (hyflo) and the solvent is evaporated off under reduced pressure to afford the crude product which is purified by preparative HPLC (VP Reprosil 100 Å-5 µm; eluent 0.1% TFA/H$_2$O→0.09% TFA/CH$_3$CN) and neutralised with saturated aqueous NaHCO3 to give the title compound as a colourless crystalline solid, m.p. 272-275° C.

The compounds of Examples 36-42 are prepared by a method analogous to that described in Example 35, by utilising the appropriate carboxamide.

Example 36

2-Methyl-[6-[[1-[[4-(4-morpholinyl)-3-(trifluoromethyl)phenylamino]carbonyl]-1H-indol-5-yl]oxy]-4-pyrimidinyl]propanamide m.p. 156-158° C.

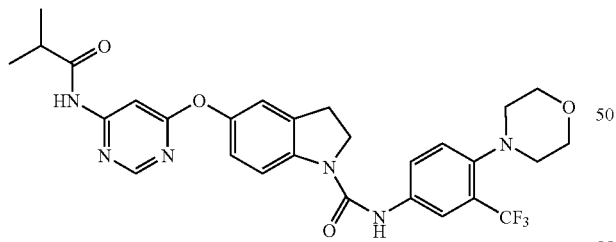

Example 37

3-Hydroxy-[6-[[1-[[4-(4-morpholinyl)-3-(trifluoromethyl)phenylamino]carbonyl]-1H-indol-5-yl]oxy]-4-pyrimidinyl]propanamide

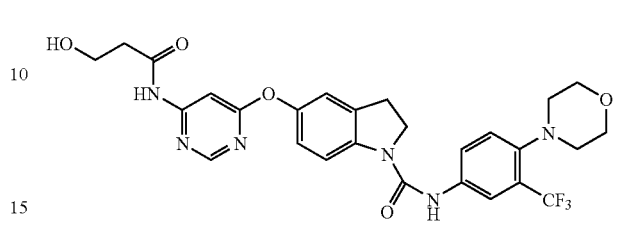

H NMR (400 MHz; DMSO-d6) δ 2.55 (t, J=6.2 Hz, 2H), 2.81 (m, 4H), 3.20 (t, J=8.6 Hz, 2H), 3.67 (m, 6H), 4.17 (t, J=8.5 Hz, 2H), 4.7 (br.s, 1H), 6.93 (dd, J=8.6, 2.3 Hz, 1H), 7.05 (d, J=1.8 Hz, 1H), 7.52 (m, 2H), 7.80-7.90 (m, 2H), 7.92 (d, J=2.3 Hz, 1H), 8.47 (s, 1H), 8.8 (br.s, 1H) and 10.8 (br.s, 1H).

Example 38

4-Methyl-4-nitro-[6-[[1-[[4-(4-morpholinyl)-3-(trifluoromethyl)phenylamino]carbonyl]-1H-indol-5-yl]oxy]-4-pyrimidinyl]pentanamide m.p. 193-197° C.

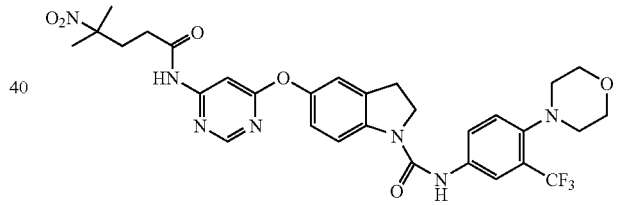

Example 39

4-Amino-4-methyl-[6-[[1-[[4-(4-morpholinyl)-3-(trifluoromethyl)phenylamino]carbonyl]-1H-indol-5-yl]oxy]-4-pyrimidinyl]propanamide m.p. 211-214° C.

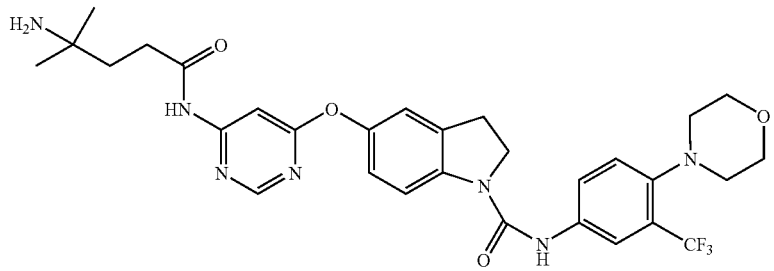

Example 40

[6-[[1-[[4-(4-Morpholinyl)-3-(trifluoromethyl)phenylamino]carbonyl]-1H-indol-5-yl]oxy]-4-pyrimidinyl]-3-pyridinecarboxamide m.p. 253-258° C.

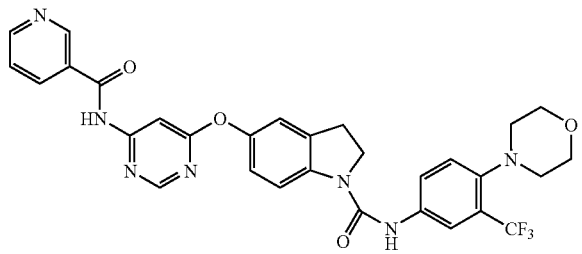

Example 41

[6-[1-[[4-(4-Morpholinyl)-3-(trifluoromethyl)phenylamino]carbonyl]-1H-indol-5-yl]oxy]-4-pyrimidinyl] carbamic acid, methyl ester m.p. 206-209° C.

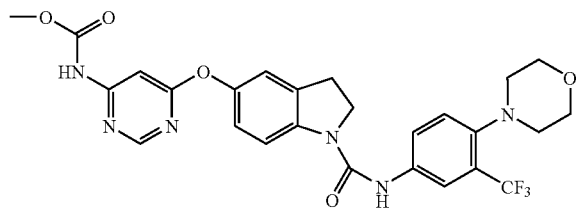

Example 42

4-Methyl-N-[[6-[1-[[4-(4-morpholinyl)-3-(trifluoromethyl)phenylamino]carbonyl]-1H-indol-5-yl]oxy]-4-pyrimidinyl]-1-piperazinecarboxamide m.p. 175-177° C.

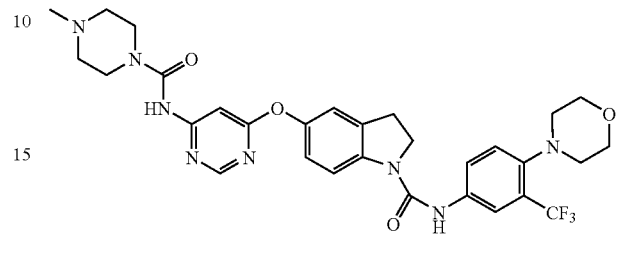

Example 43

[6-[[1-[[4-[(4-Methyl-1-piperazinyl)methyl]-3-(trifluoromethyl)phenylamino]carbonyl]-1H-indol-5-yl]oxy]-4-pyrimidinyl]acetamide

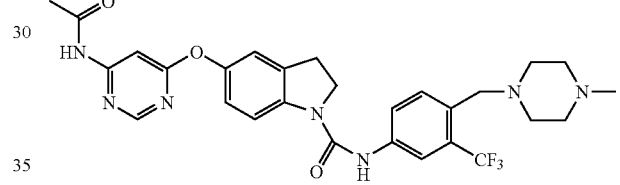

Utilising the procedure described in Example 35, but employing 2,3-dihydro-5-(6-chloro-4-pyrimidinyloxy)-N-[4-[(4-methyl-1-piperazinyl)methyl]-3-(trifluoromethyl)phenyl]-1H-indole-1-carboxamide (Intermediate IIb) in lieu of Intermediate IIa, afforded the title compound as a colourless crystalline solid, m.p. 221-223° C.

Example 44

[6-[[1-[[4-[(4-Methyl-1-piperazinyl)methyl]-3-(trifluoromethyl)phenylamino]carbonyl]-1H-indol-5-yl]oxy]-4-pyrimidinyl]-3-pyridinecarboxamide

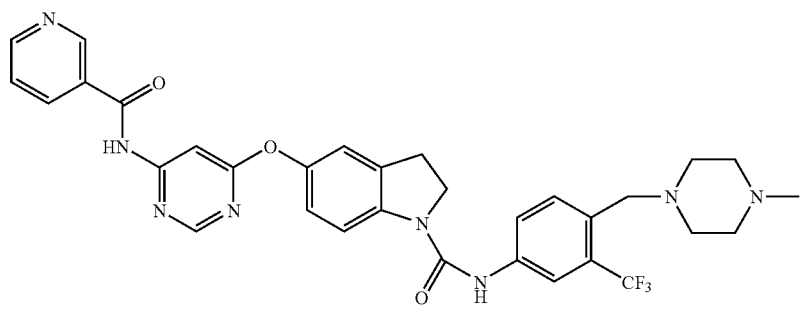

Utilising the procedure described in Example 43, but employing 3-pyridinecarboxamide in lieu of acetamide, afforded the title compound as a colourless crystalline solid, m.p. 194-195° C.

Example 45

[6-[[1-[[4-[(4-Methyl-1-piperazinyl)methyl]-3-(trifluoromethyl)phenylamino]carbonyl]-1H-indol-5-yl]oxy]-4-pyrimidinyl]carbamic acid methyl ester

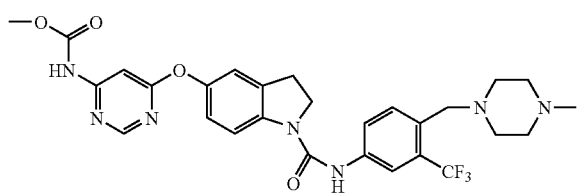

Utilising the procedure described in Example 43, but employing methyl carbamate in lieu of acetamide, afforded the title compound as a cream powder, m.p. 138-140° C.

Example 46

[6-[[1-[[4-Cyano-3-(trifluoromethyl)phenylamino]carbonyl]-1H-indol-5-yl]oxy]-4-pyrimidinyl]acetamide

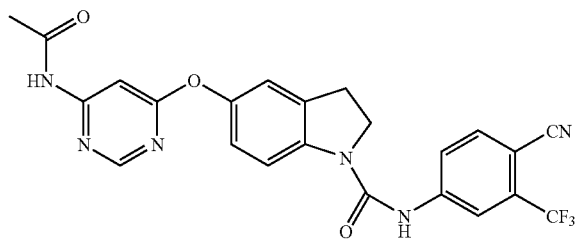

Utilising the procedure described in Example 35, but employing 2,3-dihydro-5-(6-chloro-4-pyrimidinyloxy)-N-[4-cyano-3-(trifluoromethyl)phenyl]-1H-indole-1-carboxamide (Intermediate IIc) in lieu of Intermediate IIa, afforded the title compound as a colourless crystalline solid, m.p. 204-209° C.

Example 47

[6-[[1-[[4-(4-Methyl-1-piperazinyl)-3-(trifluoromethyl)phenylamino]carbonyl]-1H-indol-5-yl]oxy]-4-pyrimidinyl]acetamide

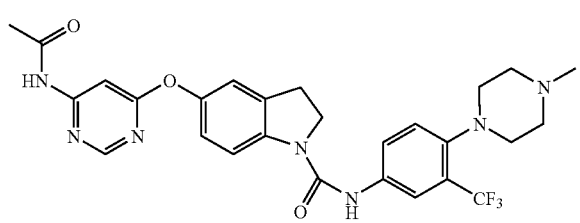

Utilising the procedure described in Example 35 but employing 2,3-dihydro-5-(6-chloro-4-pyrimidinyloxy)-N-[4-(4-methyl-1-piperazinyl)-3-(trifluoromethyl)phenyl]-1H-indole-1-carboxamide (Intermediate IId) in lieu of Intermediate IIa, afforded the title compound as a colourless crystalline solid, m.p. 238-240° C.

Example 48

[6-[[1-[[4-(4-Cyclopropyl-1-piperazinyl)-3-(trifluoromethyl)phenylamino]carbonyl]-1H-indol-5-yl]oxy]-4-pyrimidinyl]acetamide

Utilising the procedure described in Example 35, but employing 2,3-dihydro-5-(6-chloro-4-pyrimidinyloxy)-N-[4-(4-cyclopropyl-1-piperazinyl)-3-(trifluoromethyl)phenyl]-1H-indole-1-carboxamide (Intermediate IIe) in lieu of Intermediate IIa, afforded the title compound as a colourless crystalline solid, m.p. 236-240° C.

Example 49

[6-[[1-[[4-(3-Pyridinyl)-3-(trifluoromethyl)phenylamino]carbonyl]-1H-indol-5-yl]oxy]-4-pyrimidinyl]acetamide

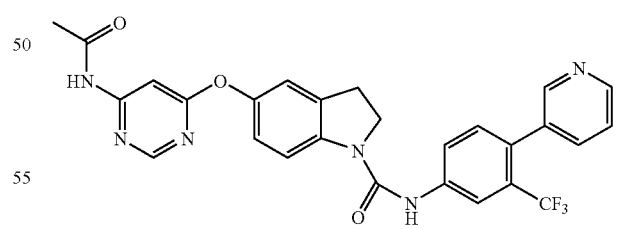

Utilising the procedure described in Example 35, but employing 2,3-dihydro-5-(6-chloro-4-pyrimidinyloxy)-N-[4-(3-pyridinyl)-3-(trifluoromethyl)phenyl]-1H-indole-1-carboxamide (Intermediate IIf) in lieu of Intermediate IIa, afforded the title compound as a colourless crystalline solid, m.p. 171-172° C.

Example 50

[6-[[1-[[4-(4-Methyl-1H-imidazol-1-yl)-3-(trifluoromethyl)phenylamino]carbonyl]-1H-indol-5-yl]oxy]-4-pyrimidinyl]acetamide

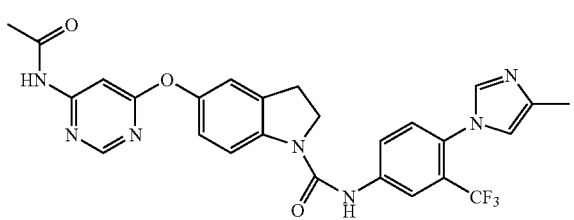

Utilising the procedure described in Example 35, but employing 2,3-dihydro-5-(6-chloro-4-pyrimidinyloxy)-N-[4-(4-methyl-1H-imidazol-1-yl)-3-(trifluoromethyl)phenyl]-1H-indole-1-carboxamide (Intermediate IIg) in lieu of Intermediate IIa, afforded the title compound as a pale-yellow crystalline solid; 1H NMR (400 MHz, DMSO-D6) δ ppm 2.10 (s, 3 H), 2.15 (m, 3 H), 3.22 (t, J=8.6 Hz, 2 H), 4.21 (t, J=8.6 Hz, 2 H), 6.96 (dd, J=8.4, 2.2 Hz, 1 H), 7.03 (s, 1 H), 7.08 (s,1 H), 7.47 (d, J=8.6 Hz, 1 H), 7.51 (s, 1 H), 7.62 (s, 1 H), 7.91 (d, J=8.6 Hz, 1 H), 8.01 (dd, J=8.8, 2.2 Hz, 1 H), 8.18 (d, J=2.3 Hz, 1 H), 8.48 (s, 1 H), 9.08 (s, 1 H) and 10.93 (s, 1H)

Example 51

[6-[[1-[[5-(4-Methyl-1H-imidazol-1-yl)-3-(trifluoromethyl)phenylamino]carbonyl]-1H-indol-5-yl]oxy]-4-pyrimidinyl]acetamide

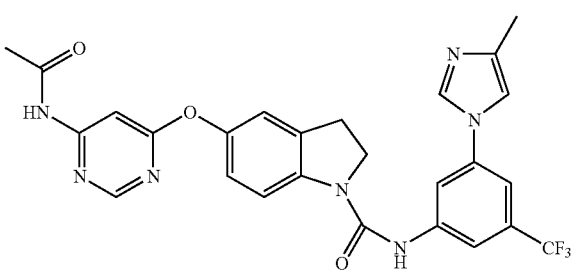

Utilising the procedure described in Example 35, but employing 2,3-dihydro-5-(6-chloro-4-pyrimidinyloxy)-N-[5-(4-methyl-1H-imidazol-1-yl)-3-(trifluoromethyl)phenyl]-1H-indole-1-carboxamide (Intermediate IIh) in lieu of Intermediate IIa, afforded the title compound as a pale-yellow crystalline solid, m.p. 223-229° C.

Example 52

[6-[[1-[[5-(4-Morpholinyl)-3-(trifluoromethyl)phenylamino]carbonyl]-1H-indol-5-yl]oxy]-4-pyrimidinyl]acetamide

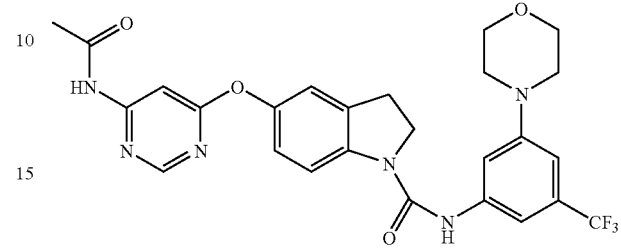

Utilising the procedure described in Example 35, but employing 2,3-dihydro-5-(6-chloro-4-pyrimidinyloxy)-N-[5-(4-morpholinyl)-3-(trifluoromethyl)phenyl]-1H-indole-1-carboxamide (Intermediate IIi) in lieu of Intermediate IIa, afforded the title compound as a cream crystalline solid, m.p. 144-146° C.

Example 53

[6-[[1-[[4-(4-Morpholinylmethyl)-3-(trifluoromethyl)phenylamino]carbonyl]-1H-indol-5-yl]oxy]-4-pyrimidinyl]acetamide

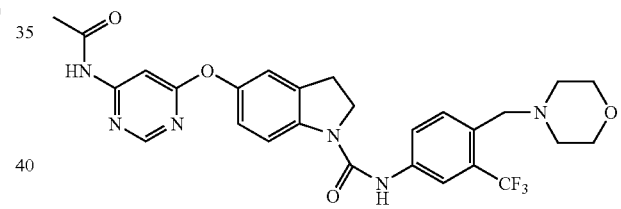

Utilising the procedure described in Example 35, but employing 2,3-dihydro-5-(6-chloro-4-pyrimidinyloxy)-N-[4-(4-morpholinylmethyl)-3-(trifluoromethyl)phenyl]-1H-indole-1-carboxamide (Intermediate IIj) in lieu of Intermediate IIa, afforded the title compound as a cream crystalline solid, m.p. 219-221° C.

Example 54

[6-[[1-[[4-(2-Methyl-1H-imidazol-1-yl)methyl])-3-(trifluoromethyl)phenylamino]carbonyl]-1H-indol-5-yl]oxy]-4-pyrimidinyl]acetamide

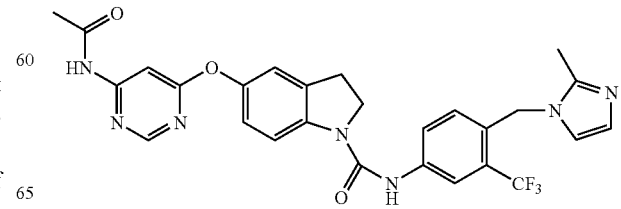

Utilising the procedure described in Example 35, but employing 2,3-dihydro-5-(6-chloro-4-pyrimidinyloxy)-N-[4-(2-methyl-1H-imidazol-1-yl)methyl)-3-(trifluoromethyl)phenyl]-1H-indole-1-carboxamide (Intermediate IIk) in lieu of Intermediate IIa, afforded the title compound as a cream crystalline solid, m.p. 244-246° C.

Example 55

[6-[[1-[[4-[(Diethylamino)methyl])-3-(trifluoromethyl)phenylamino]carbonyl]-1H-indol-5-yl]oxy]-4-pyrimidinyl]acetamide

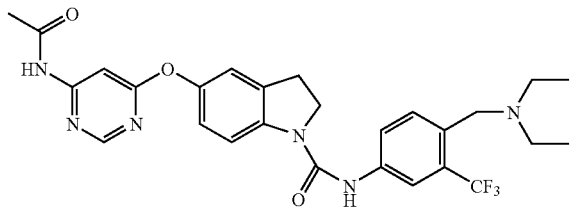

Utilising the procedure described in Example 35, but employing 2,3-dihydro-5-(6-chloro-4-pyrimidinyloxy)-N-[4-(diethylamino)methyl)-3-(trifluoromethyl)phenyl]-1H-indole-1-carboxamide (Intermediate III) in lieu of Intermediate IIa, afforded the title compound as a cream crystalline solid, m.p. 229-231° C.

Example 56

(±)-[6-[[1-[[4-[(2-Hydroxypropyl)amino]-3-(trifluoromethyl)phenylamino]carbonyl]-1H-indol-5-yl]oxy]-4-pyrimidinyl]acetamide

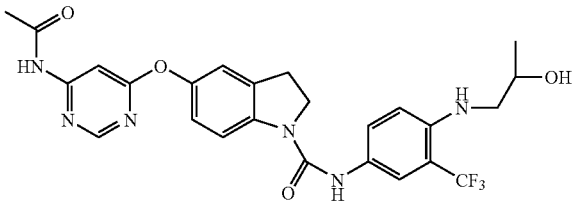

Utilising the procedure described in Example 35, but employing (±)-2,3-dihydro-5-(6-chloro-4-pyrimidinyloxy)-N-[4-[(2-hydroxypropyl)amino]-3-(trifluoromethyl)phenyl]-1H-indole-1-carboxamide (Intermediate IIm) in lieu of Intermediate IIa, afforded the title compound as a cream crystalline solid, m.p. 226-230° C.

Example 57

(±)-[6-[[1-[[4-[3-(Dimethylamino)-1-pyrrolidinyl]-3-(trifluoromethyl) phenylamino]carbonyl]-1H-indol-5-yl]oxy]-4-pyrimidinyl]acetamide

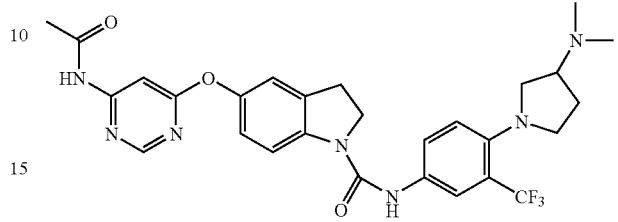

Utilising the procedure described in Example 35, but employing (±)-2,3-dihydro-5-(6-chloro-4-pyrimidinyloxy)-N-[4-[3-(dimethylamino)-1-pyrrolidinyl]-3-(trifluoromethyl)phenyl]-1H-indole-1-carboxamide (Intermediate IIn) in lieu of Intermediate IIa, afforded the title compound as a cream crystalline solid, m.p. 182-184° C.

Example 58

[6-[[1-[[4-[(1-Methyl-4-piperidinyl)oxy]-3-(trifluoromethyl)phenylamino]carbonyl]-1H-indol-5-yl]oxy]-4-pyrimidinyl]acetamide

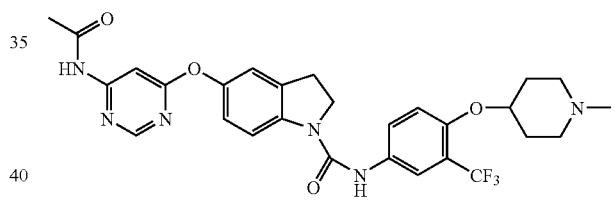

Utilising the procedure described in Example 35, but employing 2,3-dihydro-5-(6-chloro-4-pyrimidinyloxy)-N-[4-[(1-methyl-4-piperidinyl)oxy]-3-(trifluoromethyl)phenyl]-1H-indole-1-carboxamide (intermediate IIo) in lieu of Intermediate IIa, afforded the title compound as a cream crystalline solid, m.p. 200-201° C.

Example 59

[4-[[[2,3-Dihydro-5-(6-acetylamino-4-pyrimidinyloxy)-1H-indol-1-yl]carbonyl]amino]-2-(trifluoromethyl)phenoxy]-2-methylpropanoic acid, 1,1-dimethylethyl ester

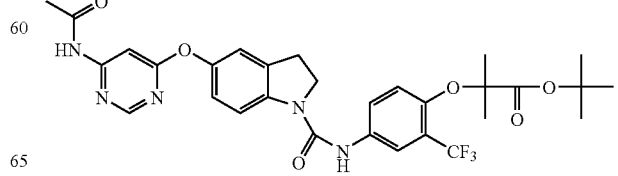

Utilising the procedure described in Example 35, but employing [4-[[[2,3-dihydro-5-(6-chloro-4-pyrimidinyloxy)-1H-indol-1-yl]carbonyl]amino]-2-(trifluoromethyl)phenoxy]-2-methylpropanoic acid, 1,1-dimethylethyl ester (Intermediate IIp) in lieu of Intermediate IIa, afforded the title compound as a yellow foam: NMR (400 MHz; DMSO-d6) δ 1.38 (s, 9H), 1.52 (s, 6H), 2.10 (s, 3H), 3.19 (t, J=8.5 Hz, 2H), 4.17 (t, J=8.6 Hz, 2H), 6.85 (d, J=9.1, 1H), 6.91 (dd, J=8.6, 2.5 Hz, 1H), 7.03 (d, J=2.5 Hz, 1H), 7.49 (s, 1H), 7.72 (dd, J=9.1, 2.5 Hz, 1H), 7.85 (m, 2H), 8.46 (s, 1H), 8.65 (s, 1H) and 10.9 (s, 1H).

Example 60

[4-[[[2,3-Dihydro-5-(6-acetylamino-4-pyrimidinyloxy)-1H-indol-1-yl]carbonyl]amino]-2-(trifluoromethyl)phenoxy]-2-methylpropanoic acid

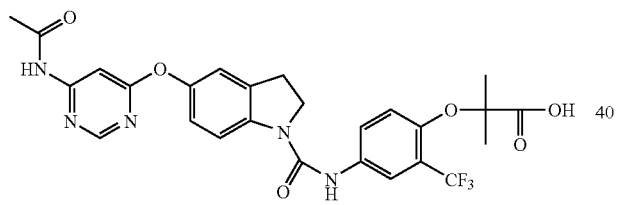

Utilising the procedure described in Example 35, but employing [4-[[(2,3-dihydro-5-(6-chloro-4-pyrimidinyloxy)-1H-indol-1-yl]carbonyl]amino]-2-trifluoromethyl)phenoxy]-2-methylpropanoic acid, 2-propenyl ester (Intermediate IIq) in lieu of Intermediate IIa, afforded the title compound, as a colourless crystalline solid, m.p.=219-220° C.

Example 61

[6-[[1-[[4-[3-(trifluoromethyl)phenylamino]carbonyl]-1H-indol-5-yl]oxy]-4-pyrimidinyl]acetamide

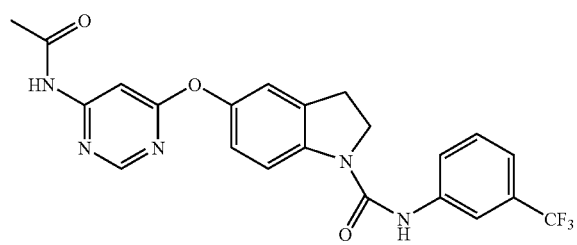

Utilising the procedure described in Example 35, but employing 2,3-dihydro-5-(6-chloro-4-pyrimidinyloxy)-N-[3-(trifluoromethyl)phenyl]-1H-indole-1-carboxamide (Intermediate IIr) in lieu of Intermediate IIa, afforded the title compound as a colourless powder, m.p.=200-201° C.

Example 62

[4-[[[2,3-Dihydro-5-(6-acetylamino-4-pyrimidinyloxy)-1H-indol-1-yl]carbonyl]amino]-2-(trifluoromethyl)phenyl]-1-piperazinecarboxylic acid, 1,1-dimethylethyl ester

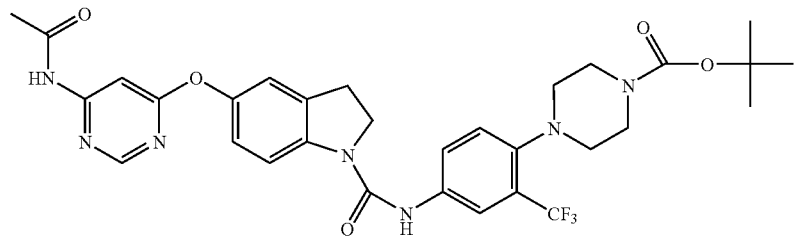

Utilising the procedure described in Example 35, but employing [4-[[(2,3-dihydro-5-(6-chloro-4-pyrimidinyloxy)-1H-indol-1-yl]carbonyl]amino]-2-(trifluoromethyl)phenyl]-1-piperazinecarboxylic acid, 1,1-dimethylethyl ester (Intermediate IIs) in lieu of Intermediate IIa, afforded the title compound as a colourless crystalline solid, m.p.=207-210° C.

Example 63

[6-[[1-[[4-Piperazinyl-3-(trifluoromethyl)phenylamino]carbonyl]-1H-indol-5-yl]oxy]-4-pyrimidinyl]acetamide

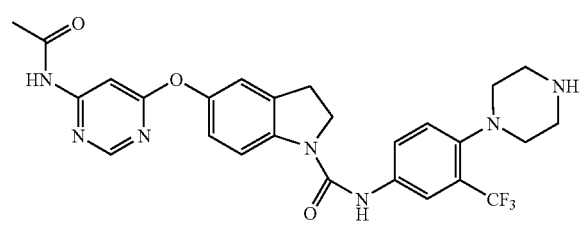

A solution of HCl (10 mL of 4M in dioxane) is added to a stirred solution of [4-[[[2,3-dihydro-5-(6-acetylamino-4-pyrimidinyloxy)-1H-indol-1-yl]carbonyl]amino]-2-(trifluoromethyl)phenyl]-1-piperazinecarboxylic acid, 1,1-dimethylethyl ester (Example 62; 320 mg, 0.5 mmol) in dioxane (10 mL). After 45 minutes, the mixture is neueralised with aqueous NaOH (2M). The precipitated product is filtered, washed with water and dried to afford the title compound as a colourless crystalline solid, m.p. 149-152° C.

Example 64

[6-[[1-[[4-[(4-Cyclopropyl-1-piperazinyl)methyl]-3-(trifluoromethyl)phenylamino]carbonyl]-1H-indol-5-yl]oxy]-4-pyrimidinyl]acetamide

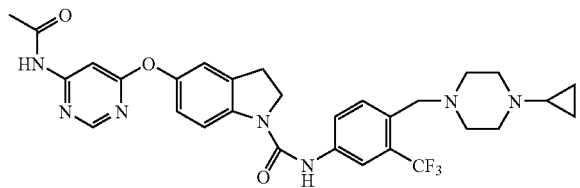

Utilising the procedure described in Example 35, but employing 2,3-dihydro-5-(6-chloro-4-pyrimidinyloxy)-N-[4-[(4-cyclopropyl-1-piperazinyl)methyl]-3-(trifluoromethyl)phenyl]-1H-indole-1-carboxamide (Intermediate IIt) in lieu of Intermediate IIa, afforded the title compound as a colourless powder, m.p. 122-126° C.

Example 65

[4-[[[2,3-Dihydro-5-(6-acetylamino-4-pyrimidinyloxy)-1H-indol-1-yl]carbonyl]amino]-2-(trifluoromethyl)phenylmethyl]-1-piperazinecarboxylic acid, 1,1-dimethylethyl ester

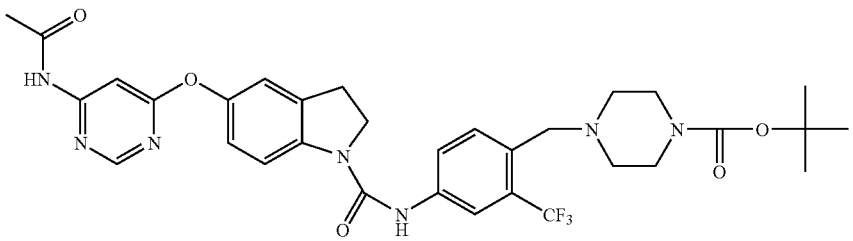

Utilising the procedure described in Example 35, but employing [4-[[(2,3-dihydro-5-(6-chloro-4-pyrimidinyloxy)-1H-indol-1-yl]carbonyl]amino]-2-(trifluoromethyl)phenylmethyl]-1-piperazinecarboxylic acid, 1,1-dimethylethyl ester (Intermediate IIu) in lieu of Intermediate IIa, afforded the title compound, as a pale yellow powder: NMR (400 MHz; DMSO-d6) δ 1.40 (s, 9H), 2.11 (s, 3H), 2.33 (m, 4H), 3.20 (t, J=8.5 Hz, 2H), 3.32 (m, 4H), 3.56 (s, 2H), 4.18 (t, J=8.6 Hz, 2H), 6.93 (dd, J=8.6 Hz, J=2.5 Hz, 1 H), 7.05 (d, J=2.4 Hz, 1H), 7.50 (d, J=1.0 Hz, 1H), 7.64 (d, J=8.5 Hz, 1H), 7.84 (dd, J=8.5 Hz, J=1.9 Hz, 1H), 7.88 (d, J=8.7 Hz, 1H), 7.98 (d, J=2.1 Hz, 1H), 8.46 (d, J=1.0 Hz, 1H), 8.81 (s, 1H) and 10.89 (s, 1H).

Example 66

[6-[[1-[[4-(1,1-Dioxido-4-thiomorpholinyl)-3-(trifluoromethyl)phenylamino]carbonyl]-1H-indol-5-yl]oxy]-4-pyrimidinyl]acetamide

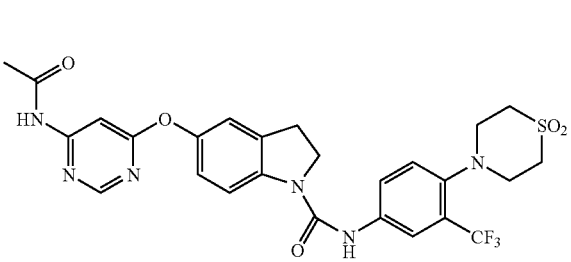

Utilising the procedure described in Example 35, but employing 2,3-dihydro-5-(6-chloro-4-pyrimidinyloxy)-N-[4-(1,1-dioxido-4-thiomorpholinyl)-3-(trifluoromethyl)phenyl]-1H-indole-1-carboxamide (Intermediate IIv) in lieu of Intermediate IIa, afforded the title compound, as a colourles crystalline solid, m.p.=284-285° C.

Example 67

[6-[[1-[[4-(1-Pyrrolidinylmethyl)-3-(trifluoromethyl)phenylamino]carbonyl]-1H-indol-5-yl]oxy]-4-pyrimidinyl]acetamide

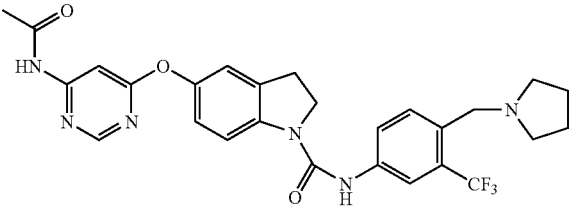

Utilising the procedure described in Example 35, but employing 2,3-dihydro-5-(6-chloro-4-pyrimidinyloxy)-N-[4-(1-pyrrolidinylmethyl)-3-(trifluoromethyl)phenyl]-1H-indole-1-carboxamide (Intermediate IIw) in lieu of Intermediate IIa, afforded the title compound as a white powder, m.p. 123-124° C.

Example 68

[6-[[1-[[4-[(1-Piperazinyl)methyl]-3-(trifluoromethyl)phenylamino]carbonyl]-1H-indol-5-yl]oxy]-4-pyrimidinyl]acetamide

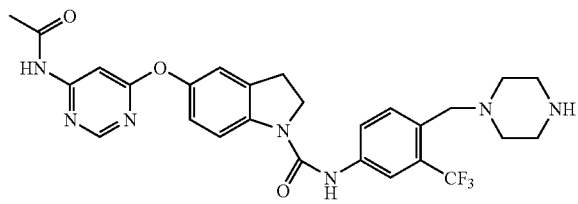

Utilising the procedure described in Example 63, but employing [4-[[[2,3-dihydro-5-(6-acetylamino-4-pyrimidinyloxy)-1H-indol-1-yl]carbonyl]amino]-2-(trifluoromethyl)phenylmethyl]-1-piperazinecarboxylic acid, 1,1-dimethylethyl ester (Example 65) in lieu of Example 62, afforded the title compound, as a colourless crystalline solid, m.p.=173-180° C.

Example 69

[2-[[1-[[4-[(4-Methyl-1-piperazinyl)methyl]-3-(trifluoromethyl)phenylamino]carbonyl]-1H-indol-5-yl]oxy]-4-pyrimidinyl]acetamide Utilising the procedure described in Example 35, but employing 2,3-dihydro-5-(2-chloro-4-pyrimidinyloxy)-N-[4-[(4-methyl-1-piperazinyl)methyl]-3-(trifluoromethyl)phenyl]-1H-indole-1-carboxamide (Intermediate IIx) in lieu of Intermediate IIa, afforded the title compound as a colourless crystalline solid, 1H NMR (400 MHz, DMSO-D6) δ ppm 2.06 (s, 3 H), 2.16 (s, 3H), 2.28-2.43 (m, 8H), 3.20 (t, J=8.2 Hz, 2H), 3.53 (s, 2 H), 4.17 (t, J=8.2 Hz, 2 H), 6.62 (d, J=5.5 Hz, 1H), 6.99 (d, J=9.4 Hz, 1H), 7.13 (s, 1 H) 7.62 (d, J=8.6, 1H), 7.84 (d, J=9.0, 1H), 7.89(d, J=8.6 Hz, 1 H), 7.97 (s, 1 H), 8.45 (d, J=6.3 Hz, 1 H), 8.81 (s, 1 H), 10.4 (s, 1 H)

Example 70

[4-[[[2,3-Dihydro-5-(6-acetylamino-4-pyrimidinyloxy)-1H-indol-1-yl]carbonyl]amino]-2-(trifluoromethyl)phenoxy]-2-methylpropanoic acid

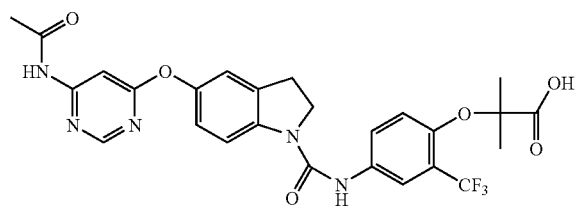

The title compound can be obtained in analogy to the procedures disclosed in the Examples described above.

Example 71

6-[1-[[3-(Trifluoromethyl)phenylamino]carbonyl]-1H-indol-5-yl]oxy]-4-pyrimidinyl]carbamic acid, methyl ester

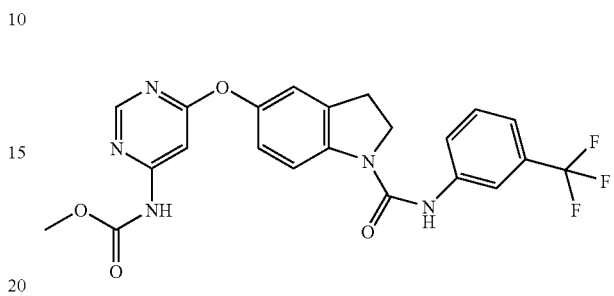

1.10 ml (14 mMol) methyl chloroformate are added dropwise over 60 min to a stirred mixture of 415 mg (1.00 mMol) 5-(6-amino-pyrimidin-4-yloxy)-2,3-dihydro-indole-1-carboxylic acid (3-trifluoromethyl-phenyl)-amide (Step 71.2) in 15 ml CH$_2$Cl$_2$ and 5 ml pyridine. After stirred for 16 h at rt, the suspension is dissolved in EtOAc and H$_2$O. The aqueous layer is separated off and extracted twice with EtOAc. The organic layers are washed with water and brine, dried (Na$_2$SO$_4$) and after addition of 3 g SiO$_2$ concentrated. The resulting powder is put on top of a SiO$_2$ column (CH$_2$Cl$_2$/MeOH 19:1) and the title compound eluted with CH$_2$Cl$_2$/MeOH 19:1: m.p. 240-241° C.

The starting material is prepared as follows:

Step 71.1: 5-(6-Azido-pyrimidin-4-yloxy)-2,3-dihydro-indole-1-carboxylic acid (3-trifluoromethyl-phenyl)-amide To a solution of 4.70 g (10.8 mMol) 5-(6-chloro-pyrimidin-4-yloxy)-2,3-dihydro-indole-1-carboxylic acid (3-trifluoromethyl-phenyl)-amide (WO 03/099771; Ex. 163) in 50 ml DMF, 1.4 g (21.6 mMol) NaN$_3$ are added at rt. Then the mixture is stirred for 3 h at 70° C., cooled to rt and pored into water and extracted tree times with EtOAc. The organic layers are washed with water and brine, dried (Na$_2$SO$_4$) and concentrated, yielding the title compound: m.p.: 167-168° C.

Step 71.2: 5-(6-Amino-pyrimidin-4-yloxy)-2,3-dihydro-indole-1-carboxylic acid (3-trifluoromethyl-phenyl)-amide 4.58 g (10.4 mMol) 5-(6-azido-pyrimidin-4-yloxy)-2,3-dihydro-indole-1-carboxylic acid (3-trifluoromethyl-phenyl)-amide in 150 ml THF are hydrogenated in the presence of 0.8 g Pd/C (10%; Engelhard 4505). The catalyst is filtered off and the filtrate concentrated. The residue is dissolved in EtOAc and H$_2$O and the aqueous layer extracted twice with EtOAc. The organic layers are washed with brine, dried (Na$_2$SO$_4$) and concentrated, yielding the title compound: m.p.: 186-187° C.

Example 72

6-[1-(3-Trifluoromethyl-phenylcarbamoyl)-2,3-dihydro-1H-indol-5-yloxy]-pyrimidine-4-carboxylic acid ethyl ester

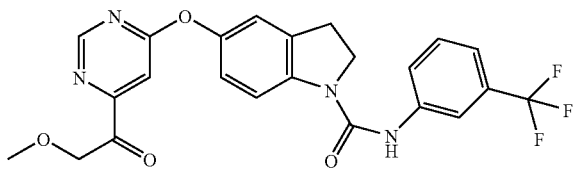

To solution of 21.9 mMol 6-(2,3-dihydro-1H-indol-5-yloxy)-pyrimidine-4-carboxylic acid ethyl ester (Step 72.2) and 3.05 ml (21.9 mMol) Et$_3$N in 30 ml THF, 3.3 ml (24 mMol) of 3-trifluoromethyl-phenyl isocyanate are added slowly. After 1 h at rt, the mixture is concentrated under reduced pressure, the residue re-dissolved in EtOAc and water, the aqueous layer separated off and extracted twice with EtOAc. The organic phases are washed with water and brine, dried (Na$_2$SO$_4$) and after addition of 25 g of SiO$_2$ concentrated. The resulting powder is put on top of a chromatography column (SiO$_2$; EtOAc/hexane 1:4) and the title compound eluated with EtOAc/hexane 1:4→1:3→1:1: m.p.: 121-123° C.; MS: [M+1]$^+$=473.

The starting material is prepared as follows:

Step 72.1:
6-(1H-indol-5-yloxy)-pyrimidine-4-carboxylic acid ethyl ester

Under a CO-atmosphere of 110 bar in an autoclave, a solution of 25 g (0.10 Mol) 5-(6-chloro-pyrimidin-4-yloxy)-indole (WO 03/099771; Stage 163.1), 30 ml (21 mMol) Et$_3$N and 3.6 g (5.1 mMol) PdCl$_2$[P(C$_6$H$_5$)$_3$]$_2$ in 480 ml ethanol is heated for 15 h at 120° C. The mixture is cooled to rt and filtered. After addition of SiO$_2$ to the filtrate, it is concentrated in vacuo. The resulting powder is put on top of a chromatography column (SiO$_2$; EtOAc/CH$_2$Cl$_2$ 1:9). Eluation with EtOAc/CH$_2$Cl$_2$ 1:9 and partial concentration leads to the crystalline title compound: MS: [M+1]$^+$=284; TLC(EtOAc/CH2Cl$_2$ 1:9): Rf=0.30.

Step 72.2: 6-(2,3-Dihydro-1H-indol-5-yloxy)-pyrimidine-4carboxylic acid ethyl ester A solution of 6.21 g (21.9 mMol) 6-(1H-indol-5-yloxy)-pyrimidine-4-carboxylic acid ethyl ester in 70 ml acetic acid is cooled in an ice bath. Then 6.88 g (109 mMol) NaBH$_3$CN are added and stirring is continued for 1 h. After addition of 17 ml water, the mixture is concentrated in vacuo. The resulting brown oil is re-dissolved in EtOAc and a 1:1 mixture of waterand sat. NaHCO$_3$, the aqueous layer separeted off and extracted twice with EtOAc. The organic phases are washed with water and brine, dried (Na$_2$SO$_4$) and concentrated to the crude title compound: MS: [M+1]$^+$=286.

Example 73

6-[1-(3-Trifluoromethyl-phenylcarbamoyl)-2,3-dihydro-1H-indol-5-yloxy]-pyrimidine-4-carboxylic acid

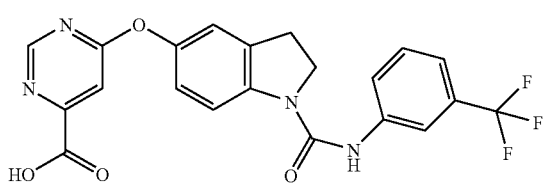

8.9 ml LiOH (1 M in H$_2$O) are added to a solution of 2.80 g (5.9 mMol) 6-[1-(3-trifluoromethyl-phenylcarbamoyl)-2,3-dihydro-1H-indol-5-yloxy]-pyrimidine-4-carboxylic acid ethyl ester in 20 ml THF. After 1 h at rt, the mixture is concentrated under reduced pressure, the residue re-dissolved in EtOAc and 1 M HCl, the aqueous layer separeted off and extracted twice with EtOAc. The organic phases are washed twice with 1 M HCl, water and brine, dried (Na$_2$SO$_4$) and concentrated to the title compound: MS: [M−1]=443; HPLC: $^A$t$_{Ret}$=12.9.

Example 74

5-(6-Phenylcarbamoyl-pyrimidin-4-yloxy)-2,3-dihydro-indole-1-carboxylic acid (3-trifluoromethyl-phenyl)-amide

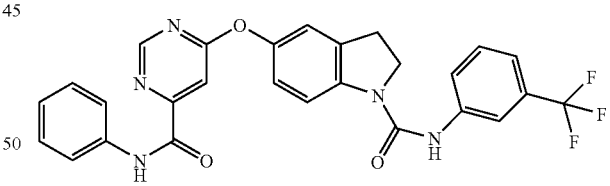

To an ice-cooled solution of 400 mg (0.90 mMol) 6-[1-(3-trifluoromethyl-phenylcarbamoyl)-2,3-dihydro-1H-indol-5-yloxy]-pyrimidine-4-carboxylic acid in 4 ml DMF, 402 µl (2.7 mMol) diethyl-cyanophosphonate and 248 µl (2.7 mMol) aniline are added. After stirring the solution for 3 h at rt, another 402 µl diethyl-cyanophosphonate are added and stirring continued for 16 h. Then the mixture is diluted with EtOAc and sat. NaHCO$_3$, the aqueous layer separeted off and extracted twice with EtOAc. The organic phases are washed with water and brine, dried (Na$_2$SO$_4$) and partially concentrated until crystals are formed. These are filtered and washed with EtOAC/DIPE, yielding the title compound: m.p.: 227-229° C.; MS: [M−1]=518; HPLC: $^A$t$_{Ret}$=17.2.

Example 75

The Following Compounds can be Obtained Analogously to Ex. 74 (Title Compounds Eventually Isolated by Chromatography)

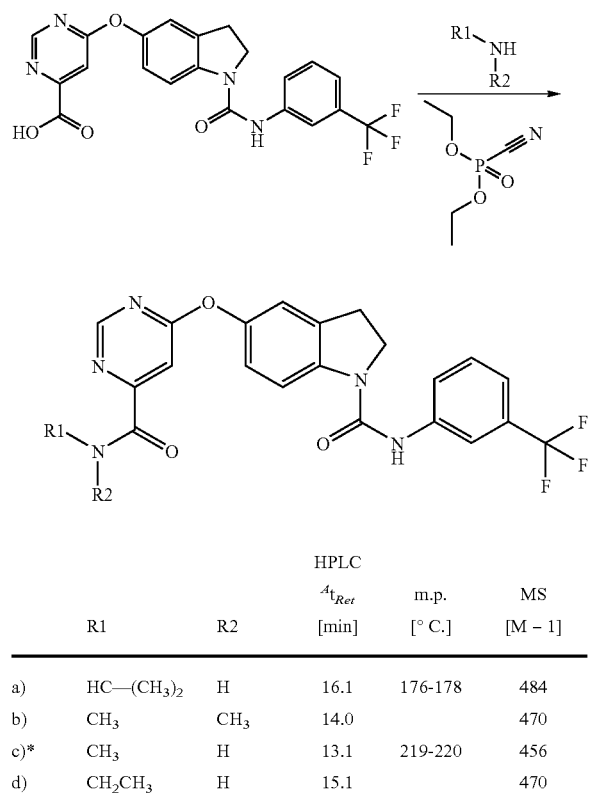

| | R1 | R2 | HPLC $^At_{Ret}$ [min] | m.p. [° C.] | MS [M − 1] |
|---|---|---|---|---|---|
| a) | HC—(CH$_3$)$_2$ | H | 16.1 | 176-178 | 484 |
| b) | CH$_3$ | CH$_3$ | 14.0 | | 470 |
| c)* | CH$_3$ | H | 13.1 | 219-220 | 456 |
| d) | CH$_2$CH$_3$ | H | 15.1 | | 470 |

*addition of catalytic amount of DMAP to reaction mixture

Example 76

5-[6-(4-Methyl-piperazine-1-carbonyl)-pyrimidin-4-yloxy]-2,3-dihydro-indole-1-carboxylic acid (3-trifluoromethyl-phenyl)-amide

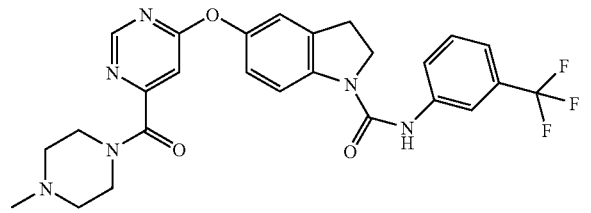

60 μl (0.7 mMol) oxalylchloride are added to a solution of 200 mg (0.45 mMol) 6-[1-(3-trifluoromethyl-phenylcarbamoyl)-2,3-dihydro-1H-indol-5-yloxy]-pyrimidine-4-carboxylic acid in 4 ml CH$_2$Cl$_2$ and 1 drop of DMF. After 1 h at rt, the solution is concentrated in vacuo. The residue is re-dissolved in THF and 108 μl (0.97 mMol) 1-methylpiperazine are added dropwise. After 2 h stirring, the mixture is diluted with EtOAc and sat. Na$_2$CO$_3$, the aqueous layer separeted off and extracted twice with EtOAc. The organic phases are washed with water and brine, dried (Na$_2$SO$_4$) and concentrated. Chromatography (Combi Flash; EtOAc→EtOAc/EtOH+2% Et$_3$N 4:1) and crystallization from EtOAc gives the title compound: m.p.: 203-204° C.; TLC(EtOAc/EtOH/NH$_3^{conc.}$ 90:10:1): Rf=0.21.

Example 77

5-(6-Dihydroxymethyl-pyrimidin-4-yloxy)-2,3-dihydro-indole-1-carboxylic acid (3-trifluoromethyl-phenyl)-amide

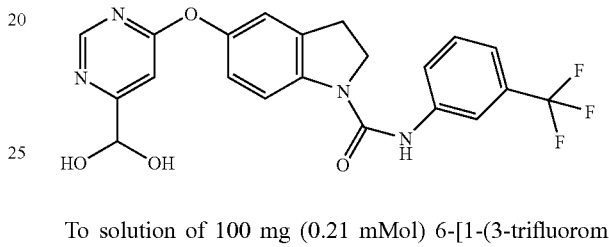

To solution of 100 mg (0.21 mMol) 6-[1-(3-trifluoromethyl-phenylcarbamoyl)-2,3-dihydro-1H-indol-5-yloxy]-pyrimidine-4-carboxylic acid ethyl ester (Expl. 72) in 3 ml THF at −78° C. are added 1.39 ml of a 1 M solution of diisobutylaluminium hydride in THF. After 20 h at −78° C., the mixture is slowly warmed up to 0° C. and stirred at this temperature for 2 h. Then the mixture is diluted with EtOAc and water, the aqueous layer separeted off and extracted twice with EtOAc. The organic phases are washed with water and brine, dried (Na$_2$SO$_4$) and after addition of 0.25 g of SiO$_2$ concentrated. The resulting powder is put on top of a chromatography column (SiO$_2$; EtOAc/hexane 1:4) and the title compound eluated with EtOAc/hexane 1:1: MS: [M+1]$^+$=446; HPLC: $^At_{Ret}$=13.0.

Example 78

5-(6-Hydroxymethyl-pyrimidin-4-yloxy)-2,3-dihydro-indole-1-carboxylic acid (3-trifluoromethyl-phenyl)-amide

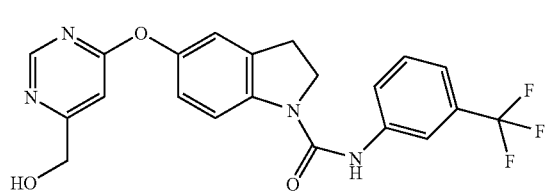

To an ice-cooled solution of 400 mg (0.9 mMol) 6-[1-(3-trifluoromethyl-phenylcarbamoyl)-2,3-dihydro-1H-indol-5-yloxy]-pyrimidine-4-carboxylic acid (Expl. 73) in 12 ml THF are added 137 μl (0.99 mMol) Et$_3$N and 130 μl (0.99 mMol) iso-butyl-chloroformate. After 1 h the resulting suspension is added dropwise to 75 mg (1.98 mMol) NaBH$_4$ in 10 ml of water. After 30 min the mixture is diluted with EtOAc and 1 M HCl, the aqueous layer separeted off and extracted twice with EtOAc. The organic phases are washed with 1 M NaOH, water and brine, dried (Na$_2$SO$_4$) and concentrated. Chromatography (Combi Flash; hexane/EtOAc 1:1→1:9) gives the title compound: MS: [M+1]$^+$=431; HPLC: $^A$t$_{Ret}$=13.6.

Example 79

5-(2-Amino-pyrimidin-4-yloxy)-2,3-dihydro-indole-1-carboxylic acid (4-chloro-3-trifluoromethyl-phenyl)-amide

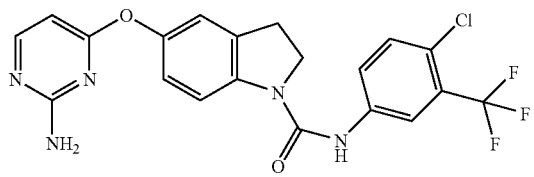

90 mg (0.30 mMol) triphosgene are dissolved in 5 ml ice-cooled CH$_2$Cl$_2$. Then a solution of 148 mg (0.76 mMol) 5-amino-2-chloro-benzotrifluoride and 0.3 ml (1.72 mMol) EtN($^i$Pr)$_2$ in 5 ml CH$_2$Cl$_2$ is added during 15 min. After stirring the reaction mixture for further 15 min, a solution of 200 mg (0.88 mMol) 5-(2-amino-pyrimidin-4-yloxy)-2,3-dihydro-1H-indole (Step 26.2) and 0.3 ml (1.72 mMol) EtN($^i$Pr)$_2$ in 5 ml THF is added. After 16 h at rt, the mixture is diluted with 10% NaHCO$_3$ solution and CH$_2$Cl$_2$, the aqueous phase separated off and extracted twice with CH$_2$Cl$_2$. The organic layers are washed with water and brine, dried (Na$_2$SO$_4$) and concentrated. Column chromatography (SiO$_2$; 1% MeOH in CHCl$_3$) gives the title compound: MS: [M+1]$^+$= 450; HPLC: $^E$t$_{Ret}$=3.7.

Example 80

5-(2-Amino-6-chloro-pyrimidin-4-yloxy)-2,3-dihydro-indole-1-carboxylic acid (4-chloro-3-trifluoromethyl-phenyl)-amide

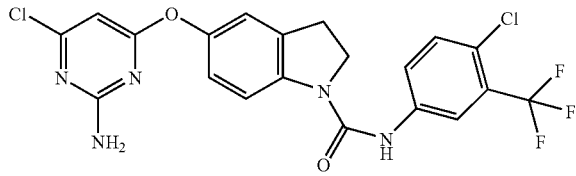

An analogous procedure to Ex. 79 starting from 5-(2-amino-6-chloro-pyrimidin-4-yloxy)-2,3-dihydro-1H-indole (Step 24.1) gives the title compound: MS: [M+1]$^+$=484; HPLC: $^E$t$_{Ret}$=4.6.

Example 81

5-(2-Amino-pyrimidin-4-yloxy)-2,3-dihydro-indole-1-carboxylic acid adamantan-2-ylamide

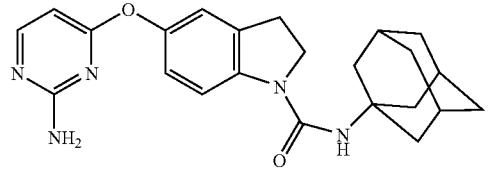

130 mg (0.44 mMol) triphosgene are dissolved in 5 ml ice-cooled CH$_2$Cl$_2$. Then a solution of 170 mg (1.12 mMol) adamantan-1-ylamine and 0.5 ml (2.87 mMol) EtN($^i$Pr)$_2$ in 5 ml CH$_2$Cl$_2$ is added during 15 min. After stirring the reaction mixture for further 15 min, a solution of 300 mg (1.33 mMol) 5-(2-amino-pyrimidin-4-yloxy)-2,3-dihydro-1H-indole (Step 26.2) and 0.5 ml (2.87 mMol) EtN($^i$Pr)$_2$ in 5 ml THF is added. After 16 h at rt, the mixture is diluted with 10% NaHCO$_3$ solution and CH$_2$Cl$_2$, the aqueous phase separated off and extracted with CH$_2$Cl$_2$. The organic layers are washed with water and brine, dried (Na$_2$SO$_4$) and concentrated. Column chromatography (SiO$_2$; hexane/EtOAc 19:1→3:1) gives the title compound: MS: [M+1]$^+$=406; HPLC: $^E$t$_{Ret}$=3.7.

Example 82
The Following Compounds can be Obtained Analogously
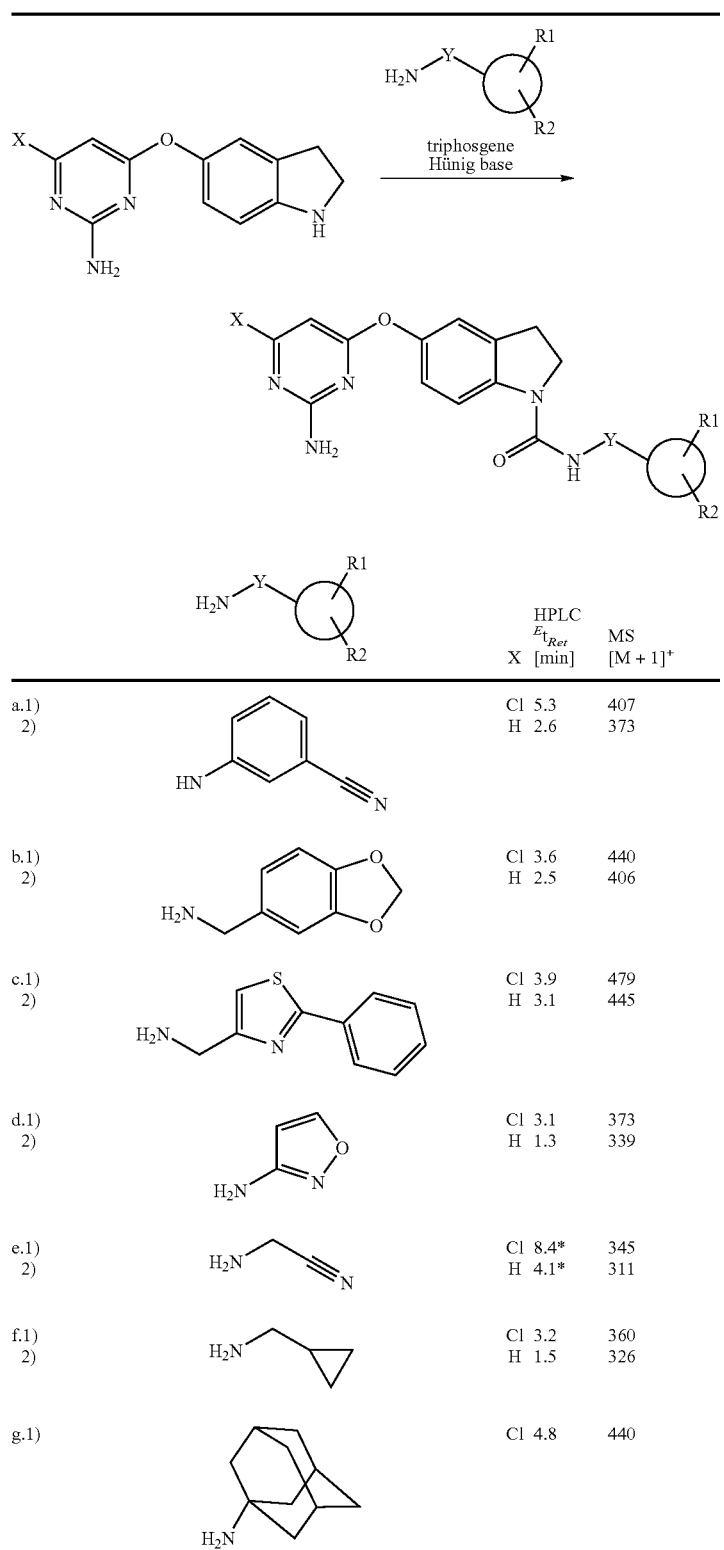
| | H₂N-Y-(R1,R2) | X | HPLC $E_{t_{Ret}}$ [min] | MS $[M+1]^+$ |
|---|---|---|---|---|
| a.1) 2) | 3-cyanoaniline (HN-C₆H₄-CN) | Cl H | 5.3 2.6 | 407 373 |
| b.1) 2) | benzodioxole-CH₂-NH₂ | Cl H | 3.6 2.5 | 440 406 |
| c.1) 2) | 2-phenylthiazol-4-yl-CH₂-NH₂ | Cl H | 3.9 3.1 | 479 445 |
| d.1) 2) | isoxazol-3-yl-NH₂ | Cl H | 3.1 1.3 | 373 339 |
| e.1) 2) | H₂N-CH₂-CN | Cl H | 8.4* 4.1* | 345 311 |
| f.1) 2) | cyclopropyl-CH₂-NH₂ | Cl H | 3.2 1.5 | 360 326 |
| g.1) | 1-adamantyl-NH₂ | Cl | 4.8 | 440 |

-continued
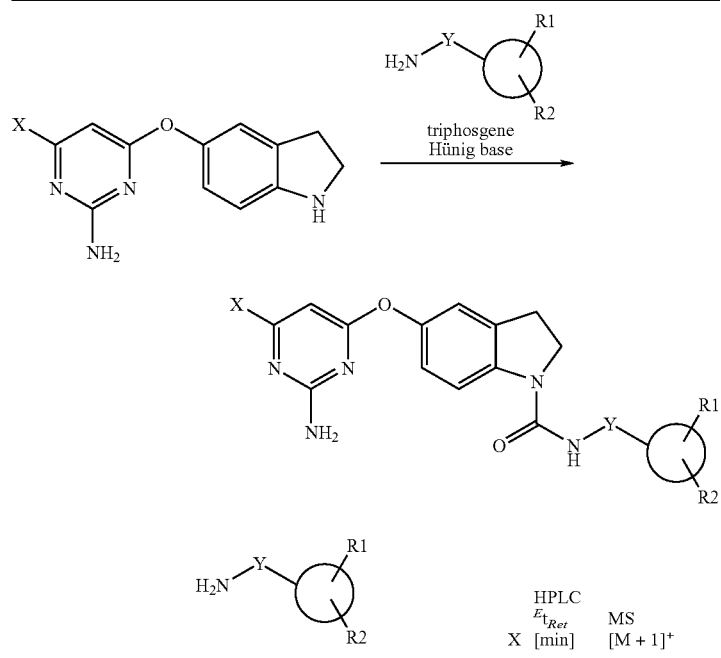
| | H₂N-Y-(R1/R2) | X | HPLC $^Et_{Ret}$ [min] | MS $[M+1]^+$ |
|---|---|---|---|---|
| h.1) 2) | (2,3-dimethylcyclohexyl)amine | Cl H | 4.3 3.2 | 416 382 |
| i.1) 2) | 2-methylbenzothiazol-6-amine | Cl H | 3.5 2.0 | 453 419 |
| j.1) 2) | 2-methylbenzoxazol-6-amine | Cl H | 3.5 1.6 | 437 401 [M − 1] |
| k.1) 2) | 5-amino-2-methyl-1-Boc-indole | Cl H | 4.9 4.1 | 535 501 |
| l.1) 2) | bornylamine | Cl H | 4.7 3.9 | 442 408 |
| m.1) 2) | 2-(1H-benzimidazol-2-yl)aniline | Cl H | 3.3 2.1 | 498 462 [M − 1] |

-continued
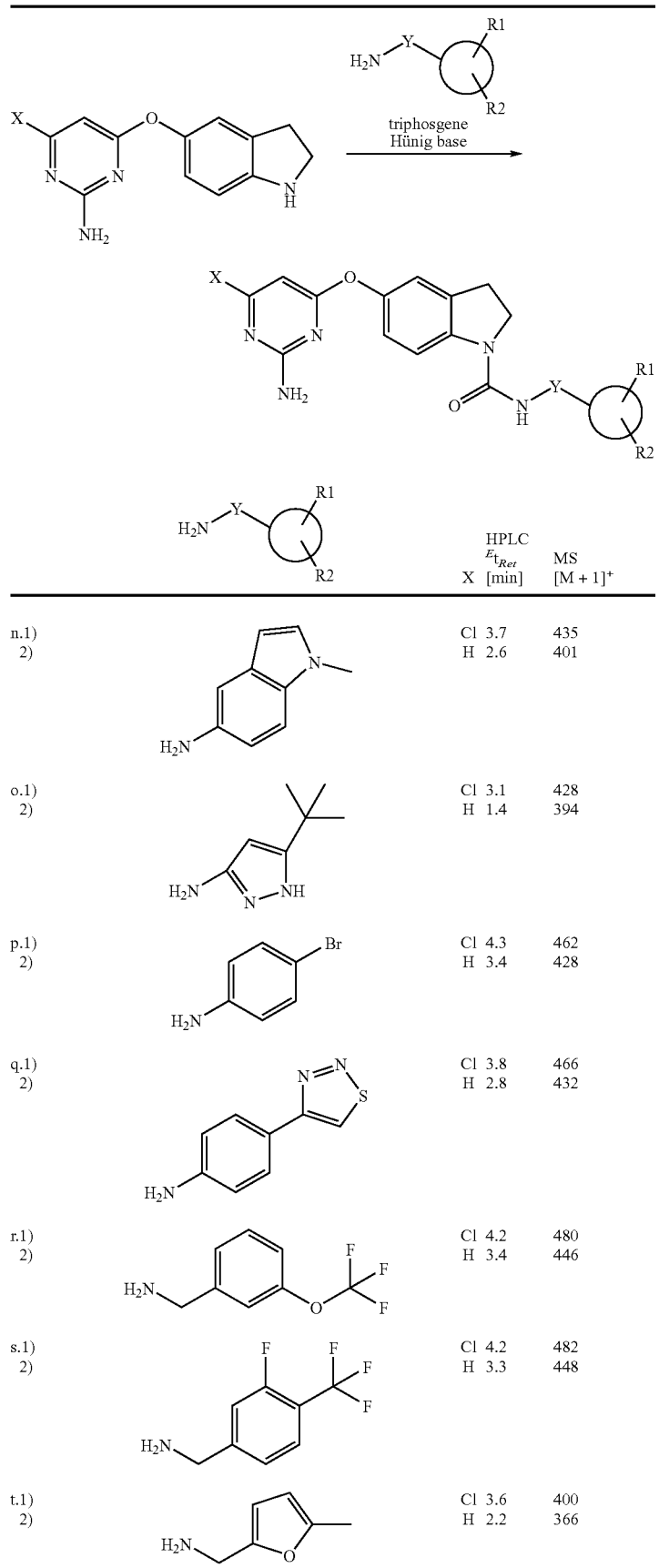
| | X | HPLC $t_{Ret}$ [min] | MS [M + 1]⁺ |
|---|---|---|---|
| n.1) 2) | | Cl 3.7 H 2.6 | 435 401 |
| o.1) 2) | | Cl 3.1 H 1.4 | 428 394 |
| p.1) 2) | | Cl 4.3 H 3.4 | 462 428 |
| q.1) 2) | | Cl 3.8 H 2.8 | 466 432 |
| r.1) 2) | | Cl 4.2 H 3.4 | 480 446 |
| s.1) 2) | | Cl 4.2 H 3.3 | 482 448 |
| t.1) 2) | | Cl 3.6 H 2.2 | 400 366 |

-continued
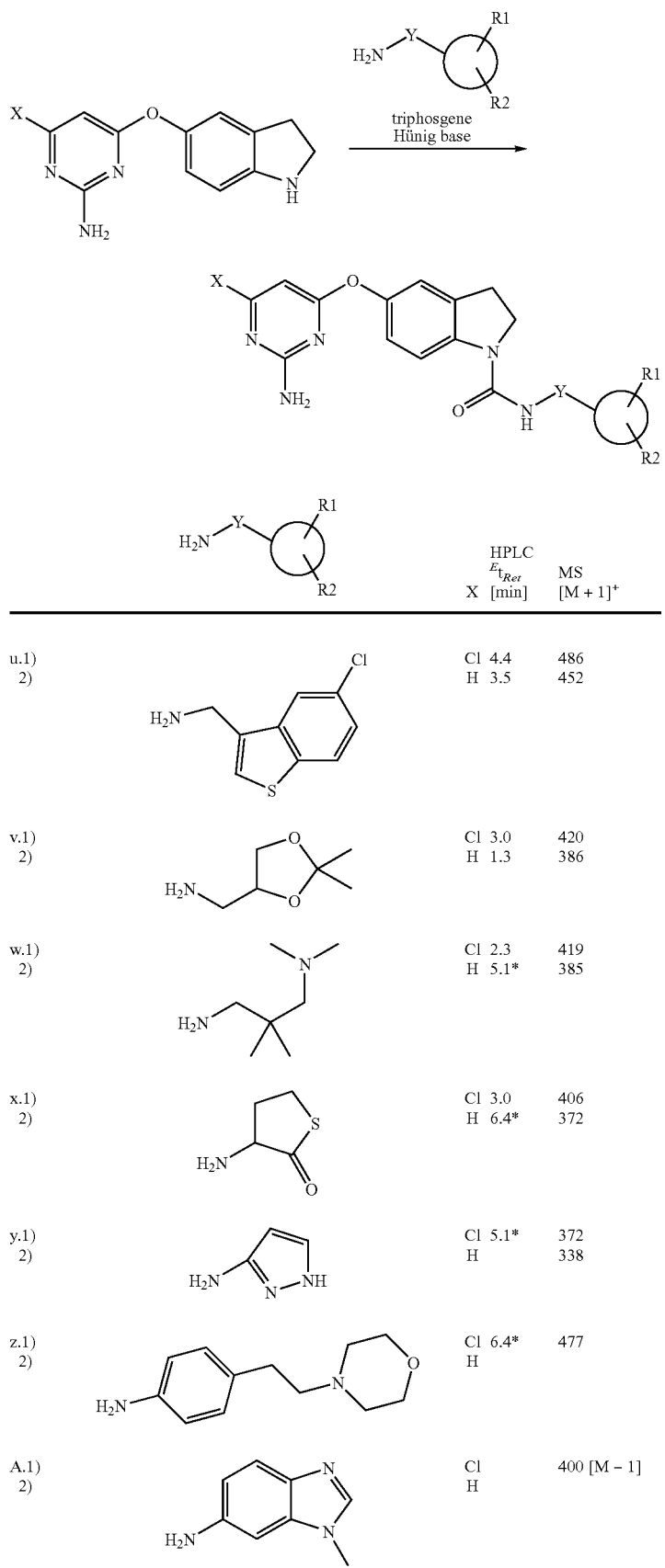
| | H₂N-Y-(R1,R2) | X | HPLC E t_Ret [min] | MS [M + 1]⁺ |
|---|---|---|---|---|
| u.1) 2) | 5-chloro-benzothiophene-3-methanamine | Cl H | 4.4 3.5 | 486 452 |
| v.1) 2) | (2,2-dimethyl-1,3-dioxolan-4-yl)methanamine | Cl H | 3.0 1.3 | 420 386 |
| w.1) 2) | N,N,2,2-tetramethyl-1,3-propanediamine | Cl H | 2.3 5.1* | 419 385 |
| x.1) 2) | 3-amino-tetrahydrothiophen-2-one | Cl H | 3.0 6.4* | 406 372 |
| y.1) 2) | 3-amino-1H-pyrazole | Cl H | 5.1* | 372 338 |
| z.1) 2) | 4-(2-morpholinoethyl)aniline | Cl H | 6.4* | 477 |
| A.1) 2) | 1-methyl-1H-benzimidazol-6-amine | Cl H | | 400 [M − 1] |

-continued
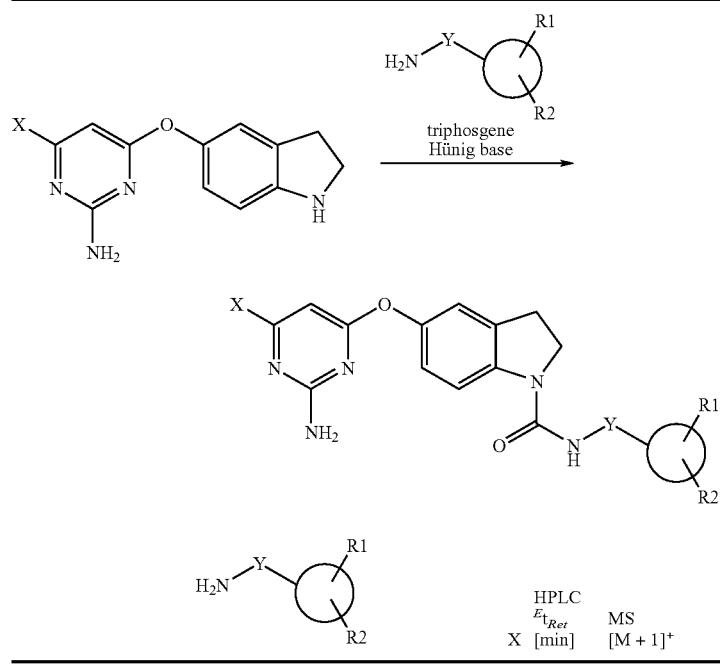
| | H₂N−Y−(R1/R2) | X | HPLC $E_{t_{Ret}}$ [min] | MS $[M+1]^+$ |
|---|---|---|---|---|
| B.1) 2) | 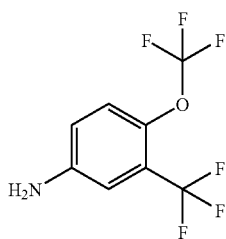 | Cl H | 14.1* 13.3 | 534 500 |
| C.1) 2) | 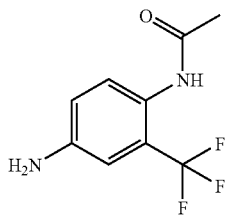 | Cl H | 11.1* 6.8* | 507 473 |
| D.1) 2) | 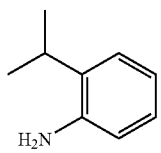 | Cl H | 4.2 3.3 | 424 390 |
| E.1) 2) | 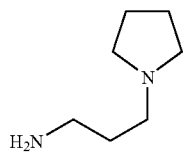 | Cl H | 1.8 | 417 383 |
| F.1) 2) | 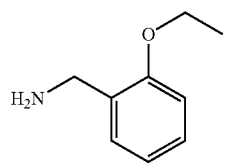 | Cl H | 4.1 3.2 | 440 406 |

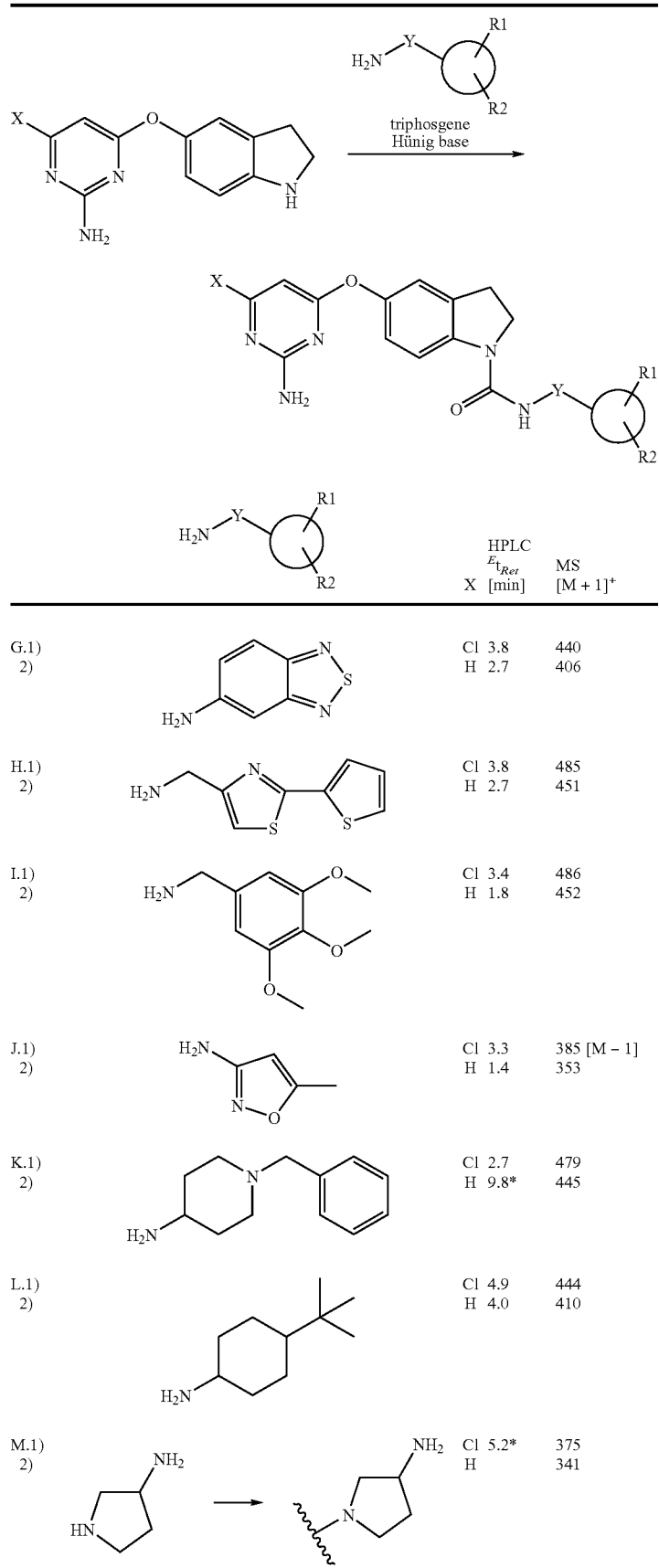

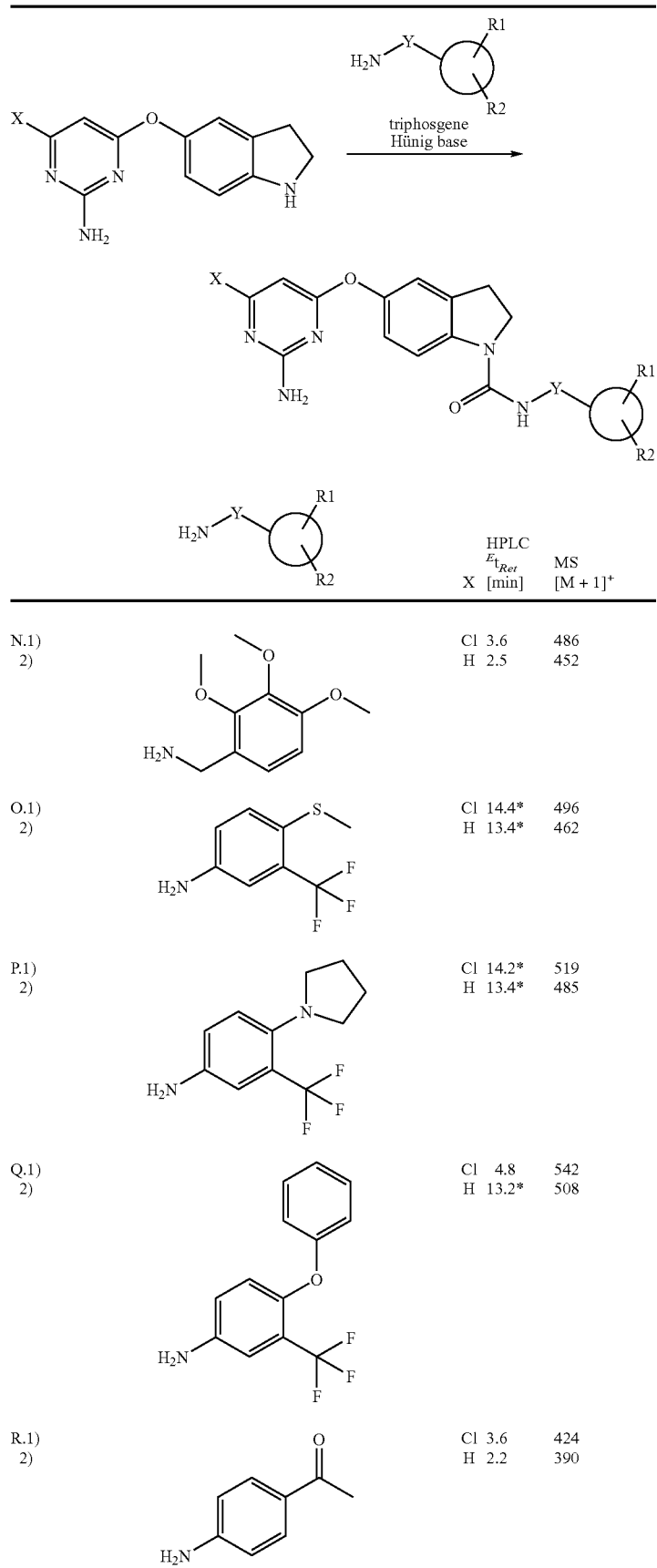
| | | X | HPLC $E_{t_{Ret}}$ [min] | MS [M + 1]+ |
|---|---|---|---|---|
| N.1) 2) | | Cl H | 3.6 2.5 | 486 452 |
| O.1) 2) | | Cl H | 14.4* 13.4* | 496 462 |
| P.1) 2) | | Cl H | 14.2* 13.4* | 519 485 |
| Q.1) 2) | | Cl H | 4.8 13.2* | 542 508 |
| R.1) 2) | | Cl H | 3.6 2.2 | 424 390 |

-continued
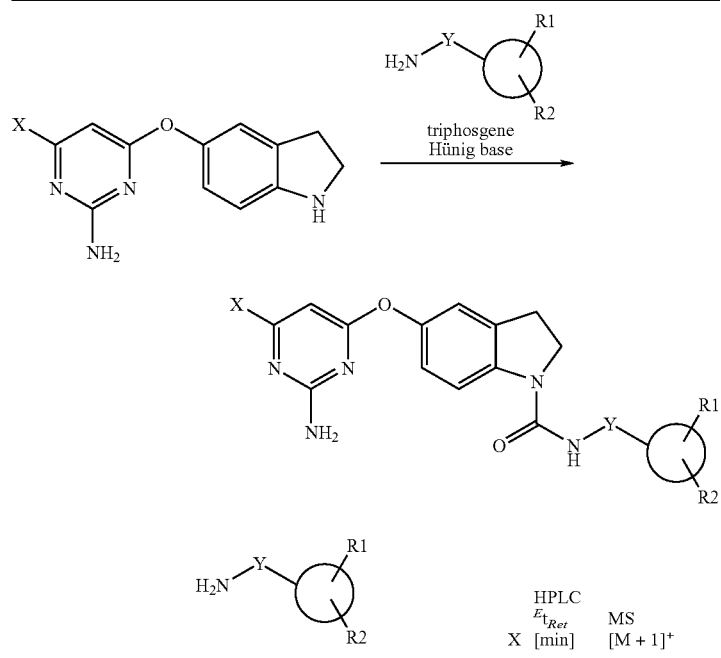
| | H₂N-Y-(R1,R2) | X | HPLC Et_Ret [min] | MS [M + 1]⁺ |
|---|---|---|---|---|
| S.1) 2) | 4-(hexyloxy)aniline | Cl H | 5.1 4.7 | 482 448 |
| T.1) 2) | (pyridin-3-yl)methanamine | Cl H | 1.9 4.0* | 397 363 |
| U.1) 2) | (3-chlorophenyl)methanamine | Cl H | 3.9 3.1 | 428 [M − 1] 396 |
| V.1) 2) | cyclopentylamine | Cl H | 3.6 2.2 | 374 340 |
| W.1) 2) | furan-2-ylmethanamine | Cl H | 3.3 1.6 | 386 352 |
| X.1) 2) | (2-(trifluoromethoxy)phenyl)methanamine | Cl H | 4.3 3.4 | 480 446 |
| Y.1) 2) | 4-amino-2-(trifluoromethyl)benzonitrile | Cl H | 4.3 3.4 | 475 441 |

-continued
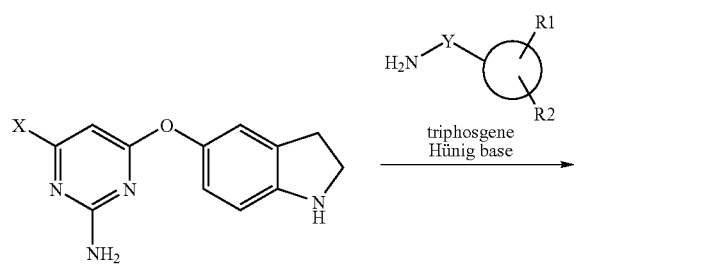
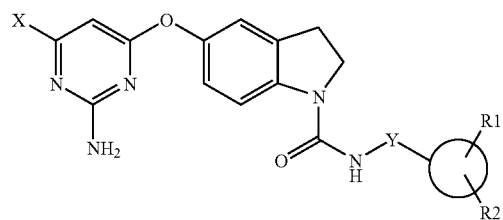
| | 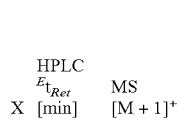 | HPLC $E_{t_{Ret}}$ | MS |
|---|---|---|---|
| | | X [min] | [M + 1]+ |
| Z.1) 2) | 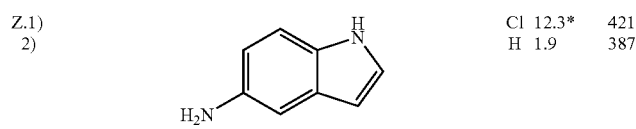 | Cl 12.3* H 1.9 | 421 387 |
| aa.1) 2) | 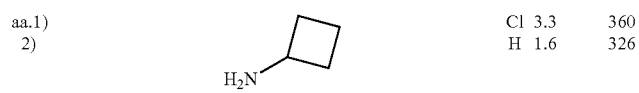 | Cl 3.3 H 1.6 | 360 326 |
| ab.1) 2) | 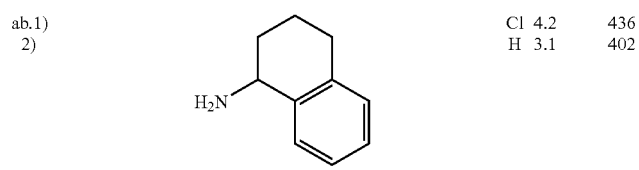 | Cl 4.2 H 3.1 | 436 402 |
| ac.1) 2) | 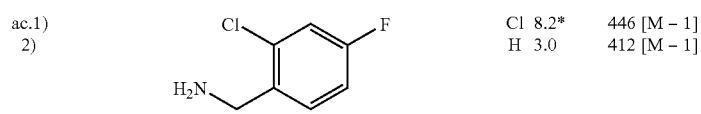 | Cl 8.2* H 3.0 | 446 [M − 1] 412 [M − 1] |
| ad.1) 2) | 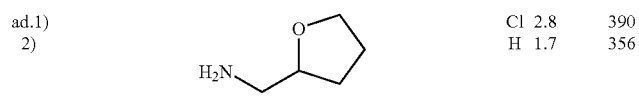 | Cl 2.8 H 1.7 | 390 356 |

-continued
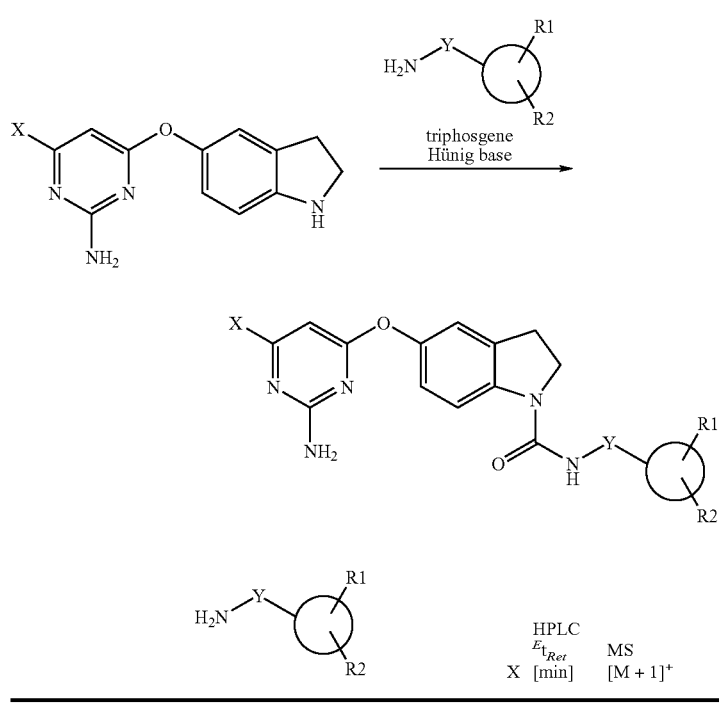
| | 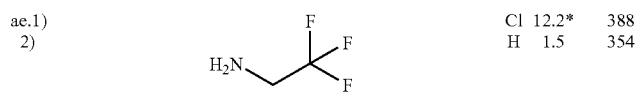 | HPLC $t_{Ret}$ | MS |
|---|---|---|---|
| | | X [min] | [M + 1]⁺ |
| ae.1) 2) | 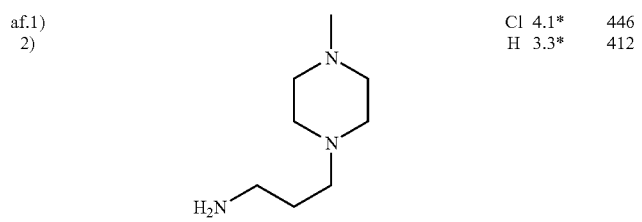 | Cl 12.2* H 1.5 | 388 354 |
| af.1) 2) | | Cl 4.1* H 3.3* | 446 412 |
| ag.1) 2) | 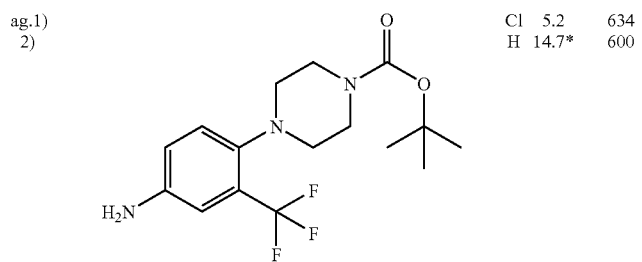 | Cl 5.2 H 14.7* | 634 600 |
| ah.1) 2) |  | Cl 4.2 H 3.3 | 480 446 |

-continued
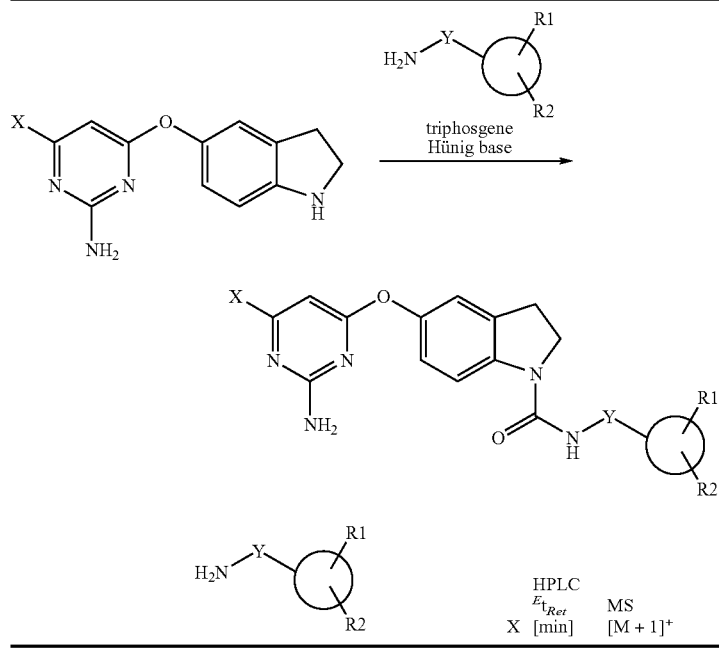
| | H₂N-Y-(R1,R2) | X | HPLC $t_{Ret}$ [min] | MS [M+1]⁺ |
|---|---|---|---|---|
| ai.1) 2) | 4-Br, 3-CF₃ aniline | Cl H | 14.7* 13.1* | 528/530 494/496 |
| aj.1) 2) | 4-(4-chlorophenoxy)-3-CF₃ aniline | Cl H | 13.9* | 576 542 |
| Ak.1) 2) | 1-acetyl-5-aminoindole | Cl H | 11.9* | 463 429 |
| al.1) 2) | 4-amino-1,2,2,6,6-pentamethylpiperidine | Cl H | | 459 425 |

-continued

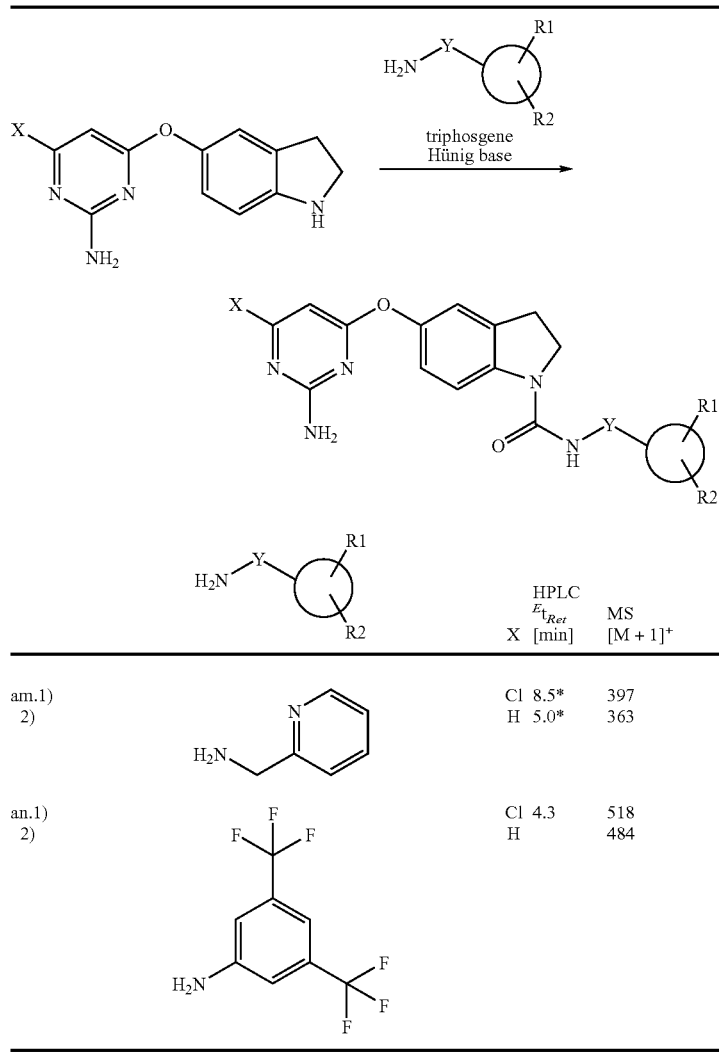

| | | X | HPLC $^F t_{Ret}$ [min] | MS $[M + 1]^+$ |
|---|---|---|---|---|
| am.1) 2) | [H₂N-CH₂-pyridin-2-yl] | Cl H | 8.5* 5.0* | 397 363 |
| an.1) 2) | [3,5-bis(trifluoromethyl)aniline] | Cl H | 4.3 | 518 484 |

*Grad $^F t_{Ret}$

Example 83

In accordance with the methods described in the Examples above, the following compounds, wherein p is 1, n is 0, A is oxygen, Y is nitrogen, and Ra and Rb are both hydrogen, can be prepared:

| Ex. | X | Z | Ar | R¹ | R² | R³ | mp (° C.) |
|---|---|---|---|---|---|---|---|
| (a) | CR³ | N | 3-(4-methyl-1H-imidazol-1-yl)-5-trifluoromethyl-phenyl | MeC(O)NH | H | H | 223-229 |
| (b) | CR³ | N | 4-(morpholin-4-yl)-5-trifluoromethyl-phenyl | trans-4-hydroxy-cyclohexyl-amino | H | H | |
| (c) | N | CR³ | 3-tert-butyl-1-p-tolyl-1H-pyrazol-5-yl | H | N₃ | H | |
| (d) | CR³ | N | 4-(4-methyl-1H-imidazol-1-yl)-5- | MeC(O)NH | H | H | |

-continued

| Ex. | X | Z | Ar | R¹ | R² | R³ | mp (° C.) |
|---|---|---|---|---|---|---|---|
| (e) | $CR^3$ | N | trifluoromethyl-phenyl 4-(1-piperazinyl)-5-trifluoromethyl-phenyl | MeC(O)NH | H | H | |
| (f) | $CR^3$ | N | 4-(4-methyl-piperazin-1-yl-methyl)-5-trifluoromethyl-phenyl | 3-pyridyl-carbonyl-amino | H | H | |
| (g) | $CR^3$ | N | 4-(4-methyl-piperazin-1-yl-methyl)-5-trifluoromethyl-phenyl | MeC(O)NH | H | H | |
| (h) | $CR^3$ | N | 4-(4-methyl-piperazin-1-yl-methyl)-5-trifluoromethyl-phenyl | $NH_2$ | H | H | |
| (i) | $CR^3$ | N | 4-(1-tert-butoxy-carbonyl-1-methyl-ethyl-1-oxy)-5-trifluoromethyl-phenyl | MeC(O)NH | H | H | |
| (j) | $CR^3$ | N | 4-(morpholin-4-yl)-5-trifluoromethyl-phenyl | $H_2NCH(CH_3)_2$—$CH_2$—$CH_2C(O)$—NH | H | H | |
| (k) | $CR^3$ | N | 4-(morpholin-4-yl)-5-trifluoromethyl-phenyl | 4-methyl-piperazinyl-carbonylamino | H | H | |
| (l) | $CR^3$ | N | 4-(4-methyl-piperazin-1-yl-methyl)-5-trifluoromethyl-phenyl | H | Me—C(O)—NH | H | |
| (m) | $CR^3$ | N | 4-(1-methyl-piperidin-4-yl-oxy)-5-trifluoromethyl-phenyl | MeC(O)NH | H | H | |
| (n) | $CR^3$ | N | 4-(4-cyclopropyl-piperazin-1-yl)-5-trifluoromethyl-phenyl | MeC(O)NH | H | H | |
| (o) | $CR^3$ | N | 4-(4-methyl-piperazin-1-yl-methyl)-5-trifluoromethyl-phenyl | 1 | H | 1 | |
| (p) | $CR^3$ | N | 4-cyano-5-trifluoromethyl-phenyl | MeC(O)NH | H | H | |
| (q) | $CR^3$ | N | 4-(morpholin-4-yl)-5-trifluoromethyl-phenyl | $O_2NC(CH_3)_2CH_2$—$CH_2C(O)NH$ | H | H | |
| (r) | $CR^3$ | N | 3-trifluoromethyl-phenyl | MeC(O)NH | H | H | |
| (s) | $CR^3$ | N | 4-(1,1-dioxo-thiomorpholin-4-yl)-5-trifluoromethyl-phenyl | MeC(O)NH | H | H | |
| (t) | $CR^3$ | N | 4-(4-tert-butoxy-carbonyl-piperazin-1-yl-methyl)-5-trifluoromethyl-phenyl | MeC(O)NH | H | H | |
| (u) | $CR^3$ | N | 4-(piperazin-1-yl-methyl)-5-trifluoromethyl-phenyl | MeC(O)NH | H | H | |
| (v) | $CR^3$ | N | 4-(4-tert-butoxy-carbonyl-piperazin-1-yl)-5-trifluoromethyl-phenyl | MeC(O)NH | H | H | |
| (w) | $CR^3$ | N | 4-(1-carboxy-1-methyl-ethyl-1-oxy)- | MeC(O)NH | H | H | |

| Ex. | X | Z | Ar | $R^1$ | $R^2$ | $R^3$ | mp (° C.) |
|---|---|---|---|---|---|---|---|
| (x) | $CR^3$ | N | 5-trifluoromethyl-phenyl 4-(4-methyl-piperazin-1-yl-methyl)-5-trifluoromethyl-phenyl | EtOC(O)NH | H | H | |
| (y) | $CR^3$ | N | 4-(4-methyl-piperazin-1-yl-methyl)-5-trifluoromethyl-phenyl | 2-thiazolyl-NH | H | H | |
| (z) | $CR^3$ | N | 4-(4-methyl-piperazin-1-yl-methyl)-5-trifluoromethyl-phenyl | $MeSO_2NH$ | H | H | |

[1] $R^3$ and $R^1$ together represent a chain —NH—CH=CH—

Example 84

Soft Capsules 5000 soft gelatin capsules, each comprising as active ingredient 0.05 g of one of the compounds of Formula I mentioned in the preceding Examples, are prepared as follows:

250 g pulverized active ingredient is suspended in 2 L Lauroglykol® (propylene glycol laurate, Gattefossé S. A., Saint Priest, France) and ground in a wet pulverizer to produce a particle size of about 1 to 3 µm. 0.419 g portions of the mixture are then introduced into soft gelatin capsules using a capsule-filling machine.

The invention claimed is:
1. A compound of Formula I:

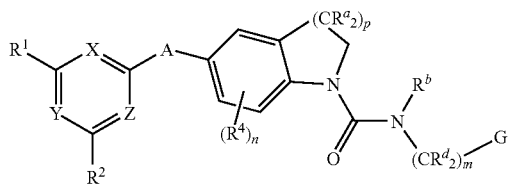

(I)

wherein
p is 1, 2 or 3;
m is 0, 1, 2 or 3;
n is 0, 1, 2 or 3;
A is $CR^c$, S, $NR^C$ or O, where $R^C$ is H or lower alkyl;
X, and Y are N, and Z is C-R3;
each $R^a$ and $R^d$ are independently selected from hydrogen and lower-alkyl;
each $R^b$ is hydrogen or lower-alkyl;
$R^1$, $R^2$ and $R^3$ are each independently selected from hydrogen; $C_1$-$C_7$ alkyl, amino; $C_1$-$C_4$-alkanoylamino, halo, and azo;
$R^4$ is selected from halo-$C_1$-$C_7$ alkyl, carboxy, $C_1$-$C_7$ alkoxycarbonyl, hydroxy, etherified or esterified hydroxy, $C_1$-$C_7$ alkoxy, phenyl, phenyl- $C_1$-$C_7$alkoxy, $C_1$-$C_7$alkanoyloxy, $C_1$-$C_7$alkanoyl, amino, mono- or di-substituted amino, amidino, ureido, mercapto, N-hydroxy-amidino, guanidino, amidino-$C_1$-$C_7$alkyl, sulfo, sulfamoyl, carbamoyl, cyano, cyano-$C_1$-$C_7$alkyl and nitro;

G is a group Ar or represents CN;
Ar is selected from:

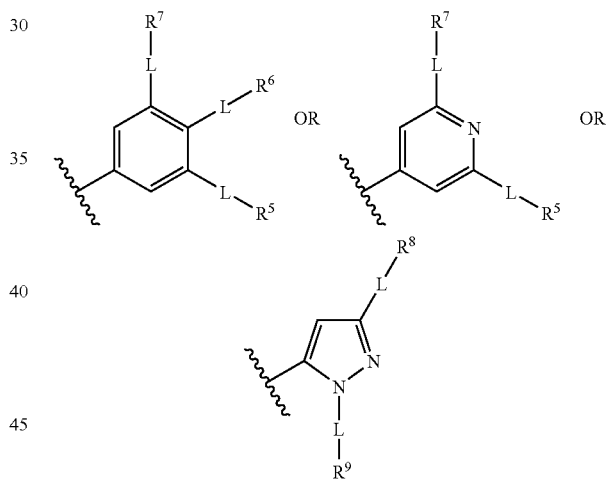

where $R^5$, $R^6$, $R^7$, $R^8$ and $R^9$ are each independently selected from hydrogen, halo, hydroxyl, etherified or esterified hydroxy, cyano, azo, nitro;

substituted or unsubstituted lower alkyl, lower alkenyl, lower alkynyl, lower alkoxy, amino, a carbocyclic group, a heterocyclic group or mono- or di-substituted amino, being substituted by a substituted or unsubstituted hydrocarbyl moiety, the hydrocarbyl moiety selected from lower alkyl, cycloalkyl, lower alkanoyl;

or any two of -L-$R^5$, -L-$R^6$ or -L-$R^7$ together form a lower alkylene-dioxy bridge bound via the oxygen atoms;

or any two of -L-$R^5$, -L-$R^6$ or -L-$R^7$ together form a five, six or seven membered heterocyclic ring, which may be substituted or unsubstituted, especially a substituted indazole ring;

wherein the carb comprises $C_3$ to $C_6$ in chain carbon atoms and is substituted or unsubstituted; and wherein the heterocyclic group especially comprises five, six or seven in-chain atoms of which at least one is a heteroatom selected from N, O or S and is substituted or unsubstituted and wherein L is a covalent bond or a moiety which comprises 1, 2, 3 or 4 in-chain atoms selected from carbon, oxygen, sulphur and nitrogen or salts, esters, or N-oxides thereof.

2. A compound according to claim 1, wherein p is 1.

3. A compound according to claim or claim 1, wherein A is oxygen.

4. A compound according to claim 1, wherein $R^4$ is selected from hydroxy, or halo.

5. A compound according to any preceding claim, wherein n is 0.

6. A compound according to claim 1, wherein at least one $R^a$ is hydrogen.

7. A compound according to claim 1, wherein $R^2$ is selected from hydrogen, $C_1$-$C_7$alkyl, amino, $C_1$-$C_4$alkanoylamino, halo and azo.

8. A compound according to claim 1, wherein $R^2$ is hydrogen.

9. A compound according to claim 1, wherein $R^b$ is hydrogen.

10. A compound according to claim 1, wherein the carbocyclic group is selected from phenyl, cyclohexyl and cyclopentyl.

11. A compound according to claim 1, wherein $R^5$, $R^6$, $R^7$, $R^6$ and $R^9$ are each independently selected from:
lower alkyl, halo, halo-lower alkyl, lower alkoxy, halo-lower alkoxy, acylamino, substituted acylamino, phenyl, substituted phenyl, cyano; amino, hydroxyl, azo, nitro, carbamate, or
mono- or di-substituted amino, being substituted by lower alkyl, haloalkyl, cycloalkyl, lower alkanoyl, phenyl; or heterocyclic group.

12. A compound according to claim 11, wherein the heterocyclic group is selected from furan, thiophene, pyrrole, imidazole, pyrazole, isoxazole, oxazole, thiazole, pyran, pyridazine, indole, isoindole, indazole, purine, indolizidine, quinoline, isoquinoline, quinazoline, pteridine, quinolizidine, pyrimidine, pyrazine, pyridyl, alkyl-pyridyl, piperidyl, piperazinyl, alkyl-piperazinyl, pyrollidine, morpholinyl, thiomorpholinyl.

13. A compound according to claim 12, wherein the heterocyclic group is selected from pyridine, pyrrolidine, pyrazole, thiazole, imidazole, piperazine, piperidine, morpholine and 1,1-dioxo-thiomorpholine.

14. A compound according to claim 13, wherein at least one of $R^5$, $R^6$, $R^7$ or $R^8$ is a heterocyclic group selected from piperazine group or a pyrrolidine group.

15. A compound according to claim 14, wherein the piperazine or pyrrolidine group is substituted by an alkyl group.

16. A compound according to claim 15, wherein -L- is selected from methyl or ethyl, oxygen, sulphur or nitrogen or is a covalent bond.

17. A compound according to claim 16, wherein $R^5$, if present, is selected from $CF_3$, Me, Cl, OMe.

18. A compound according to claim 17, wherein $R^5$ is $CF_3$.

19. A compound according to claim 18, wherein only one of $R^6$ and $R^7$ is present.

* * * * *